US006933142B1

(12) United States Patent
Bistrup et al.

(10) Patent No.: US 6,933,142 B1
(45) Date of Patent: Aug. 23, 2005

(54) HEC-G1CNAC6ST

(75) Inventors: Annette Bistrup, San Francisco, CA (US); Steven D. Rosen, San Francisco, CA (US); Stefan Hemmerich, San Francisco, CA (US)

(73) Assignees: The Regents of the University of California, Oakland, CA (US); Syntex (USA), LLC, Palo Alto, CA (US)

( * ) Notice: Subject to any disclaimer, the term of this patent is extended or adjusted under 35 U.S.C. 154(b) by 421 days.

(21) Appl. No.: 09/645,078

(22) Filed: Aug. 23, 2000

Related U.S. Application Data

(63) Continuation-in-part of application No. PCT/US99/04316, filed on Feb. 26, 1999, which is a continuation-in-part of application No. 09/190,911, filed on Nov. 12, 1998, now Pat. No. 6,365,365, which is a continuation-in-part of application No. 09/045,284, filed on Mar. 20, 1998, now Pat. No. 6,265,192.

(51) Int. Cl.$^7$ .......................... C12N 9/10; C07K 14/435
(52) U.S. Cl. ...................................... 435/193; 530/395
(58) Field of Search ........................ 435/193; 530/395; 536/23.2

(56) References Cited

U.S. PATENT DOCUMENTS

| | | | |
|---|---|---|---|
| 5,185,326 A | 2/1993 | Muller et al. | |
| 5,227,369 A | 7/1993 | Rosen et al. | |
| 5,318,890 A | 6/1994 | Rosen et al. | |
| 5,580,862 A | 12/1996 | Rosen et al. | |
| 5,695,752 A | 12/1997 | Rosen et al. | |
| 5,827,817 A | 10/1998 | Larsen et al. | |
| 5,955,325 A | 9/1999 | Habuchi | |
| 6,265,192 B1 | 7/2001 | Bistrup et al. | |
| 6,365,365 B1 | 4/2002 | Bistrup et al. | |

FOREIGN PATENT DOCUMENTS

| | | | |
|---|---|---|---|
| EP | 0 821 066 A1 | 1/1998 | |
| EP | 1130094 | 9/2001 | |
| WO | WO 00/14251 | * 3/2000 | ........... C12N/15/54 |
| WO | WO 00/58473 | 10/2000 | |
| WO | WO 01/85177 | 11/2001 | |

OTHER PUBLICATIONS

Bistrup et al. Sulfotransferases of two specificities function in the reconstitution of high endotherlial cell ligands for L–selectin. Journal of Cell Biology. May 17, 1999, vol. 145, No. 4, pp. 899–910.*
Hiroaka et al. A novel, high endothelial venule–specific sulfotransferase expresses 6–sulfo sialyl Lewis(X), an L–seelctin ligand displayed by CD34. Immunity. Jul. 1999. vol. 11. No. 1, pp. 79–89.*
Lifeseq clone#2620445.
Lifeseq clone#2617407.

Baumhueter, Susanne, et al., (1993) "Binding of L–Selectin to the Vascular Sialomucin CD34," *Science*, vol. 262:436–438.
Bertozzi, Carolyn, et al., (1995) "Sulfated Dissacharide Inhibitors of L–Selectin: Deriving Structural Leads from a Physiological Selectin Ligand," *Biochemistry*, vol. 34(44):14271–14278.
Boukerche, Habib, et al., (1996) "A Monoclonal Antibody Directed Against A Granule Membrane Glycoprotein (GMP–140/PADGEM, P–Selectin, CD62P) Inhibits Ristocetin–Induced Platelet Aggregation," *British Journal of Haemathology*, vol. 92:442–451.
Carter et al. (1988) "Enzymatic Sulfation of mucus glycoprotein in gastric mucosa." *J. Biol. Chem.*, vol. 263(24):11977–11984.
Celi, Alessandro, et al., (1997) "Platelet–Leukocyte–Endothelial Cell Interaction On The Blood Vessel Wall," *Seminars in Hematology*, vol. 34(4):327–335.
Crommie, Deidre, et al., (1995) "Biosynthesis of GlyCAM–1, a Mucin–Like Ligand for L–Selectin," *The Journal of Biological Chemistry*, vol. 270(38) :22614–22624.
Frenette, Paul S., et al., (1995) "Platelets Roll on Stimulated Endothelium in Vivo: An Interaction Mediated By Endothelial P–Selection," *Proc. Natl. Acad. Sci.*, vol. 92:7450–7454.
Fukuta et al. (1997) "Molecular Cloning and Characterization of Human Keratan Sulfate Gal–6–Sulfotransferase." *J. Biol. Chem.*, vol. 272(51):32321–32328.
Fukuta, Masakazu, et al., (1965) "Molecular Cloning and Expression of Chick Chondrocyte Chondroitin 6–Sulfotransferase," *The Journal of Biological Chemistry*, vol. 270(31):18575–18580.
Fukuta, Masakazu et al., (1997) "Molecular Cloning and Characterization of Human Keratan Sulfate Gal–6–Sulfotransferase," *The Journal of Biological Chemistry*, vol. 272 (51):32321–32328.
Girard, Jean–Philippe, et al., (1995) "High Endothelial Venules (HEV$_s$): Specialized Endothelium For Lymphocyte Migration," *Immunology Today*, vol. 16(9):449–457.
Habuchi, Osami, et al., (1997) "Sulfation of Sialyl Lactosamine Oligosaccharides By Chondroitin 6–Sulfotransferase," *Gycobiology*, vol. 7(3):405–412.

(Continued)

*Primary Examiner*—Marjorie Moran
(74) *Attorney, Agent, or Firm*—Paula A. Borden; Bozicevic, Field & Francis, LLP

(57) ABSTRACT

Mammalian glycosylsulfotransferases expressed in high endothelial cells (HEC-GLCNAC6ST) and polypeptides related thereto, as well as nucleic acid compositions encoding the same, are provided. The subject polypeptides and nucleic acid compositions find use in a variety of applications, including diagnostic, and therapeutic agent screening applications. Also provided are methods of inhibiting selectin mediated binding events and methods of treating disease conditions associated therewith, particularly by administering an inhibitor of at least one of HEC-GLCNAC6ST or KSGal6ST, or homologues thereof.

13 Claims, 11 Drawing Sheets

Habuchi, Osami, et al., (1996) "Enzymatic Sulfation of Galactose Residue of Keratan Sulfate By Chrondroitin 6–Sulfotransferase," *Glycobiology*, vol. 6(1):51–57.

Habuchi, Osami, et al., (1993) "Purification of Chondroitin 6–Sulfotransferase Secreted from Cultured Chick Embryo Chrondrocytes," *The Journal of Biological Chemistry*, vol. 268(29):21968–21974.

Habuchi, Hiroko, et al., (1998) A Molecular Characterization and Expression of Heparan–Sulfate 6–Sulfotransferase *The Journal of Biological Chemistry*, vol. 273(15):9208–9213.

Hemmerich, Stefan, et al., (1995) "Structure of the O–Glycans in GlyCAM–1, An Endothelial–Derived Ligand for L–Selectin," *The Journal of Biological Chemistry*, vol. 270(20):12035–12047.

Hemmerich, Stefan, et al., (1994) "Sulfation–Dependent Recognition of High Endothelial Venules (HEV)–Ligands by L–Selectin and MECA 79, An Adhesion–Blocking Monoclonal Antibody," *The Journal of Experimental Medicine*, vol. 180:2219–2226.

Hemmerich, Stefan, et al., (1994) "6'–Sulfated Sialyl Lewis x Is a Major capping Group of GlyCAM–1," *Biochemistry*, vol. 33(16):4830–4835.

Hemmerich, Stefan, et al., (1994) "Identification of the Sulfated monosaccharides, of GlyCAM–1, an Endothelial–Derived Ligand for L–Selectin," *Biochemistry*, vol. 33(16):4820–4829.

Hillier, Marra M., et al., "The WashU–HHMI Mouse EST Project," *Nucleotide Query* (1996) Accession No. AA522184.

Hooper, Lora V., et al., (1996) "From Legumes to Leukocytes:Biological Roles For Sulfated Carbohydrates," *The FASEB Journal*, vol. 10:1137–1146.

Koenig, Andrea, et al., (1997) "Selectin Inhibition: Synthesis and Evaluation of Novel Sialylated, Sulfated and Fucosylated Oligosccharides, Including The Major Capping Group of GlyCAM–1," *Glycobiology*, vol. 7(1):79–93.

Lasky, Laurence A., et al., (1992) "An Endothelial Ligand for L–Selectin Is a Novel Mucin–Like Molecule," *Cell*, vol. 69:927–938.

Mitsuoka, Chikako, et al., (1998) An Identification of a Major Carbohydrate Capping Group of the L–Selectin Ligand on High Endothial Venules in Human Lymph Nodes as 6–Sulfo Sialyl Lewis X, *The Journal of Biological Chemistry*, vol. 273(18):11225–11233.

Rosen, Steven D., et al., (1994) "The Selectins and their Ligands," *Current Opinion in Cell Biology*, vol. 6:663–673.

Sawada, Mikiko, et al., (1993) "Specific Expression of a Complex Sialyl Lewis X Antigen on High Endothelial Venules of Human Lymph Nodes: Possible Candidate for L–Selectin Ligand," *Biochemistry and Biophysical Communications*, vol. 193(1):337–347.

Spiro et al. (1996) "Characterization of a rat liver Golgi sulphotransferase responsible for the 6–O–sulphation of N–acetylglucosamine residues in B–linkage to mannose: role in assembly of sialyl–galactosyl–N–acetylglucosamine 6–sulphate sequence of N–linked oligosaccharides." *Biochem. J.*, vol. 319(1):209–216.

Spiro, Robert G., et al., (1998) Characterization of a Spleen Sulphortransferase Responsible for the 6–O–Sulphation of the Galactose Residue in Sialyl–N–Acetyl–Lactosamine Sequences, *Biochem J.*, vol. 331:265–271.

Tsuboi, Shigeru, et al., (1996) "6'–Sulfo Sialyl Le$^x$ but Not 6–Sulfo Sialyl Le$^x$ Expressed on the Cell Surface Supports L–Selectin–Mediated Adhesion," *The Journal of Biological Chemistry* vol. 271(44):27213–27216.

Yoshino, Kochichiro, et al., (1997) "Studies on Selectin Blockers. 4. Structure–Function Relationship of Sulfated Sialyl Lewis X Hexasaccharide Ceramides Towards E–, P–, and L–Selectin Binding," *J. Med. Chem.*, vol. 40:455–462.

Arbonés et al. (1994) "Lymphocyte homing and leukocyte rolling and migration are impaired in L–selectin–deficient mice." *Immunity*, vol. 1(4):247–60.

Aruffo et al. (1987) "Molecular cloning of a CD28 cDNA by a high–efficiency COS cell expression system." *Proc Natl Acad Sci U S A.*, vol. 84(23):8573–7.

Bierhuizen et al. (1992) "Expression cloning of a cDNA encoding UDP–GlcNAc:Gal beta 1–3 GalNAc–R (GlcNAc to GalNAc) beta 1–6GlcNAc transferase by gene transfer into CHO cells expressing polyoma large tumor antigen." *Proc Natl Acad Sci U S A.*, vol. 89(19):9326–330.

Fukuta et al. (1998) "Molecular cloning and expression of human chondroitin 6–sulfotransferase." *Biochem Biophys Acta.*, vol. 1399(1):57–61.

Girard et al. (1995) "Cloning from purified high endothelial venule cells of hevin, a close relative of the antiadhesiv extracellular matrix protein SPARC." *Immunity*, vol. 2(1):113–23.

Imai et al. (1993) "Sulphation requirement for GlyCAM–1, an endothelial ligand for L–selectin." *Nature*, vol. 361(6412):555–7.

Imai et al. (1993) "Direct demonstration of heterogeneous, sulfated O–linked carbohydrate chains on an endothelial ligand for L–selectin." *Glycoconj J.*, vol. 10(1):34–9.

Kakuta et al. (1998) "Conserved structural motifs in the sulfotransferase family." *Trends Biochem Sci.*, vol. 23(4):129–30.

Li et al. (1996) "Post–translational modifications of recombinant P–selectin–glycoprotein ligand–1 required for binding to P–and E–selectin." *J Biol Chem.*, vol. 271(6):3255–64.

Maly et al. (1996) "The alpha(1,3)fucosyltransferase Fuc–TVII controls leukocyte trafficking through an essential role in L–, E–, and P–selectin ligand biosynthesis." *Cell*, vol. 86(4):643–53.

Schall (1997) "Fractalkine–a strange attractor in the chemokine landscape." *Immunol Today*, vol. 18(4):147.

Schworak et al. (1997) "Molecular cloning and expression of mouse and human cDNAs encoding heparan sulfate D–glucosaminyl 3–O–sulfotransferase." *J Biol Chem*, vol. 272(44):28008–19.

Uchimura et al. (1998) "Human N–acetylglucosamine–6–O–sulfotransferase involved in the biosynthesis of 6–silfo sialyl Lewis X: molecular cloning, chromosomal mapping, and expression in various organs and tumor cells." *J Biochem (Tokyo)*, vol. 124(3):670–8.

\* cited by examiner

FIG. 1

>huGST-3 (from LifeSeq EST #2617407, ORF is highlighted in capitals)
gaattccattgtgttgggtacggaagacgacagaagggtagaggagaaaagcgcatgg
cccggctagcagtgagcctctcaaaagcagcagggaagcccaagccacaaggtcttcc
acttcagcacaatgctactgcctaaaaaaATGAAGCTCCTGCTGTTTCTGGTTTCCCA
GATGGCCATCTTGGCTCTATTCTTCCACATGTACAGCCACAACATCAGCTCCCTGTCT
ATGAAGGCACAGCCCGAGCGCATGCACGTGCTGGTTCTGTCTTCCTGGCGCTCTGGCT
CTTCTTTTGTGGGGCAGCTTTTTGGGCAGCACCCAGATGTTTTCTACCTGATGGAGCC
CGCCTGGCACGTGTGGATGACCTTCAAGCAGAGCACCGCCTGGATGCTGCACATGGCT
GTGCGGGATCTGATACGGGCCGTCTTCTTGTGCGACATGAGCGTCTTTGATGCCTACA
TGGAACCTGGTCCCCGGAGACAGTCCAGCCTCTTTCAGTGGGAGAACAGCCGGGCCCT
GTGTTCTGCACCTGCCTGTGACATCATCCCACAAGATGAAATCATCCCCCGGGCTCAC
TGCAGGCTCCTGTGCAGTCAACAGCCCTTTGAGGTGGTGGAGAAGGCCTGCCGCTCCT
ACAGCCACGTGGTGCTCAAGGAGGTGCGCTTCTTCAACCTGCAGTCCCTCTACCCGCT
GCTGAAAGACCCCTCCCTCAACCTGCATATCGTGCACCTGGTCCGGGACCCCCGGGCC
GTGTTCCGTTCCCGAGAACGCACAAAGGGAGATCTCATGATTGACAGTCGCATTGTGA
TGGGGCAGCATGAGCAAAAACTCAAGAAGGAGGACCAACCCTACTATGTGATGCAGGT
CATCTGCCAAAGCCAGCTGGAGATCTACAAGACCATCCAGTCCTTGCCCAAGGCCCTG
CAGGAACGCTACCTGCTTGTGCGCTATGAGGACCTGGCTCGAGCCCCTGTGGCCCAGA
CTTCCCGAATGTATGAATTCGTGGGATTGGAATTCTTGCCCCATCTTCAGACCTGGGT
GCATAACATCACCCGAGGCAAGGGCATGGGTGACCACGCTTTCCACACAAATGCCAGG
GATGCCCTTAATGTCTCCCAGGCTTGGCGCTGGTCTTTGCCCTATGAAAAGGTTTCTC
GACTTCAGAAAGCCTGTGGCGATGCCATGAATTTGCTGGGCTACCGCCACGTCAGATC
TGAACAAGAACAGAGAAACCTGTTGCTGGATCTTCTGTCTACCTGGACTGTCCCTGAG
CAAATCCACTAAgagggttgagaaggctttgctgccacctggtgtcagcctcagtcac
tttctctgaatgcttctgagccttgcctacatctctgagccttaactacatgtctgtg
ggtatcacactgagtgtgagttgtgtccacacgtgctcaagcagaaggacttttgtgt
ccatgcttgtgtctagaaaacagactggggaaccttatgtgagcagcacatcccacca
gtgaaacagggtattgctcttcttctttttcttgatcttcctgtctgggcagacttcag
agactttgtggcctggaggcctattaagcacgacacagtatcagtggaattgatccat
aaacctccctgtccacatcttgcccaatggggaatggatctttcaccaaagagctcac
cagcattttccacagagatgcgaattctgagcccttggagttcccaatgggattcaag
gaaggaagtgggaacaaggttggatgcctacttatgagcttgaccatacagctatcgg
taatcagaaatatgaaacaaaatctctgacaaaagagcaagctcttaagttcacaagg
tgcctgggcttgatttgaatatcatttccctttgcattttcccattacatagaaaact
ttgacctgtgaaacttgccatctgttaatactaaaattcccaaataaggttctgttta
gaatgtcccttttatgcttcttaattattagcagtaaatgttcatttttatgggatc
ctaaaaaaaaaaa

FIG. 2

>huGST-3 (Full length EST Lifeseq #2617407)
MLLPKKMKLLLFLVSQMAILALFFHMYSHNISSLSMKAQPERMHVLVLSSWRSGSSFV
GQLFGQHPDVFYLMEPAWHVWMTFKQSTAWMLHMAVRDLIRAVFLCDMSVFDAYMEPG
PRRQSSLFQWENSRALCSAPACDIIPQDEIIPRAHCRLLCSHNPLRWWKRPCRSYSHV
VLKEVRFFNLQVPIPAAERPLLNLHIVHLVLDPRSVFRSRERTKGDLMIDSRIVMGQH
EQKLKKEDQPYYVMQVICQSQLEIYKTIQSLPKALQERYLLVRYEDLARAPVAQTSRM
YEFVGLEFLPHLQTWVHNITRGKGMGDHAFHTNARDALNVSQAWRWSLPYEKVSRLQK
ACGDAMNLLGYRHVRSEQEQRNLLLDLLSTWTVPEQIH

FIG. 3

>msGST-3 from mouse C57Bl/6 BAC clone #87(b15)   (ORF is highlighted as capitals)

gggcatctaacttacacttggtcagacaagacaagcttttgcctacaaaggccacact
ctgtcaggggtgtagaaaggtgtggggtgtggcagaactccctatagtgattaaatgt
gctgggtaggatattctcggtggtttgatggatgagaaagcccagagggtgagtttta
aagacttgtaacatagaatgcagtgatccaattaagagccagaattactttgcagagg
gatctggacaaatacttgcaggaatgttttggttttgtttgtttgtttgttt
tacattgctccttggatgggaatccagagaagcccgaaggtagatgctgtaacaacct
aactcagccccatccctctgcttgctctttcaaggtcttctccttcttccgcaggAT
GATGCTGTTGAAGAAAGGGAGGCTGCTGATGTTCCTGGGTTCCCAGGTCATCGTTGTA
GCTCTCTTCATCCATATGTCCGTCCACAGACACCTTTCCCAGAGGGAGGAGTCCAGGA
GGCCCGTGCATGTGCTGGTGCTGTCTTCCTGGCGGTCAGGATCCTCTTTTGTGGGACA
GCTTTTCGGGCAGCACCCGGATGTGTTCTACCTGATGGAGCCTGCCTGGCATGTGTGG
ATGACTTTCACCAGCAGCACAGCCTGGAAGCTGCACATGGCTGTGCGGGATCTTCTGC
GTTCCGTCTTCCTGTGTGACATGAGCGTCTTTGATGCCTACATGAACCCAGGCCCCG
GAAACAGTCCAGCCTCTTCCAGTGGGAGCAAAGCCGGGCCCTGTGCTCAGCGCCTGTG
TGTGACTTCTTCCCTGCCCACGAGATCAGCTCACCCAAGCACTGCAAGCTGCTCTGCG
GTCAGCAGCCCTTTGATATGGTGGAGAAGGCCTGCCGCTCTCACGGCTTCGTGGTACT
CAAGGAGGTGCGTTTTCTCAGCCTGCAGGCCCTCTATCCACTACTCACGGACCCTTCC
CTCAACCTGCACGTCGTGCACCTGGTCCGAGACCCCCGGGCCGTGTTCCGATCCCGGG
AGCACACCACCATAGAACTCATGGTTGACAGTCATATTGTGCTAGGGCAGCATTTGGA
AACGATCAAGGAGGAAGACCAGCCCTATTATGCCATGAAGATCATCTGCAAAAGCCAG
GTGGACATAGTCAAGGCCATCCAAACCCTCCCTGAAGCTCTGCAGCAGCGCTACCTGT
TCCTGAGGTATGAGGACCTGGTTCGGGCACCCCTGGCCCAGACGACCAGACTATATAA
ATTTGTGGGGTTGGATTTTTTGCCCCACCTCCAAACATGGGTTTACAATGTCACCCGC
GGCAAGGGCATGGGTCAGCATGCCTTCCATACTAACGCCAGGAACGCCCTCAACGTCT
CTCAGGCGTGGCGTTGGTCCTTACCTTACGAAAAGGTTTCCCAGCTTCAAGATGCCTG
CGGTGAGGCTATGGATTTGCTGGGATACCTCCAGGTCAGATCTCAACAAGAACAAGGC
AACCTGTCCCTGGATCTTCTGTCCTCCTCCCATATCTTGGGGCAGGTCTTCCGAGAAG
GTTAAggaggtctgtctgcacccettggttccagccttagtcaccattaaacgcacag
aagccttaaggtataaccaaactgagtgccccttctcctcagcccaagcagagggg
tctttgtgtctatactcatgtctaccctacaactgagcctaaaaagccaagaaacagt
atctttctgtcttgaaaatacttaggaaccttaagcagccctttgacctgtcaagca
agactttcttgtaaccttggccttcttacctgtgcataccttggagactcggtctgga
ggcatactggacacagcaaacagcatctgtggagtgtgtctgtaaacctccctgtcac
atcttttctaag

FIG. 4

>msGST-3 translation of ORF from mouse C57Bl/6 BAC clone #87(b15)
MMLLKKGRLLMFLGSQVIVVALFIHMSVHRHLSQREESRRPVHVLVLSSWRSGSSFVG
QLFGQHPDVFYLMEPAWHVWMTFTSSTAWKLHMAVRDLLRSVFLCDMSVFDAYMNPGP
RKQSSLFQWEQSRALCSAPVCDFFPAHEISSPKHCKLLCGQQPFDMVEKACRSHGFVV
LKEVRFLSLQALYPLLTDPSLNLHVVHLVRDPRAVFRSREHTTIELMVDSHIVLGQHL
ETIKEEDQPYYAMKIICKSQVDIVKAIQTLPEALQQRYLFLRYEDLVRAPLAQTTRLY
KFVGLDFLPHLQTWVYNVTRGKGMGQHAFHTNARNALNVSQAWRWSLPYEKVSQLQDA
CGEAMDLLGYLQVRSQQEQGNLSLDLLSSSHILGQVFREG

```
                    106                              134
HEC-GlcNAc6ST   SWRSGSSFVGQLFGQHPDVFYLMEPAWHV
GlcNAc6ST       TWRSGSSFFGELFNQNPEVFFLYEPVWHV
KSGal6ST        TTRSGSSFVGQLFNQHLDVFYLFEPLYHV
C6ST            TTRTGSSFVGEFFNQQGNIFYLFEPLWHI 249                    270
HEC-GlcNAc6ST   DPSLNLHIVHLVRDPRAVFRSR
GlcNAc6ST       DPALDLKVIHLVRDPRAVASSR
KSGal6ST        DPRLNLKVLQLVRDPRGILASR
C6ST            DPRLDLRMIQLVRDPRAVLASR 320              339
HEC-GlcNAc6ST   PKALQERVLLVRYEDLARAP  (SEQ ID NO: 16)
GlcNAc6ST       PDWLQGHYLVVRYEDLVGDP  (SEQ ID NO: 17)
KSGal6ST        PFWLKGKYMLVRYEDLARNP  (SEQ ID NO: 18)
C6ST            PAWLRGRYMLVRYEDMARGP  (SEQ ID NO: 19)
```

FIG. 6

SEQUENCE LISTING

<160> NUMBER OF SEQ ID NOS: 35

<210> SEQ ID NO 1
<211> LENGTH: 2043
<212> TYPE: DNA
<213> ORGANISM: HOMO SAPIENS

<400> SEQUENCE: 1

```
gaattccatt gtgttgggta cggaagacga cagaagggta gaggagaaaa gcgcatggcc      60
cggctagcag tgagcctctc aaaagcagca gggaagccca agccacaagg tcttccactt     120
cagcacaatg ctactgccta aaaaaatgaa gctcctgctg tttctggttt cccagatggc     180
catcttggct ctattcttcc acatgtacag ccacaacatc agctccctgt ctatgaaggc     240
acagcccgag cgcatgcacg tgctggttct gtcttcctgg cgctctggct cttcttttgt     300
ggggcagctt tttgggcagc acccagatgt tttctacctg atggagcccg cctggcacgt     360
gtggatgacc ttcaagcaga gcaccgcctg gatgctgcac atggctgtgc gggatctgat     420
acgggccgtc ttcttgtgcg acatgagcgt ctttgatgcc tacatggaac tggtccccg     480
gagacagtcc agcctctttc agtgggagaa cagccgggcc ctgtgttctg cacctgcctg     540
tgacatcatc ccacaagatg aaatcatccc ccgggctcac tgcaggctcc tgtgcagtca     600
acagcccttt gaggtggtgg agaaggcctg ccgctcctac agccacgtgg tgctcaagga     660
ggtgcgcttc ttcaacctgc agtccctcta cccgctgctg aaagacccct ccctcaacct     720
gcatatcgtg cacctggtcc gggacccccg ggccgtgttc cgttcccgag aacgcacaaa     780
gggagatctc atgattgaca gtcgcattgt gatggggcag catgagcaaa aactcaagaa     840
ggaggaccaa ccctactatg tgatgcaggt catctgccaa agccagctgg agatctacaa     900
gaccatccag tccttgccca aggccctgca ggaacgctac ctgcttgtgc gctatgagga     960
cctggctcga gcccctgtgg cccagacttc ccgaatgtat gaattcgtgg gattggaatt    1020
cttgccccat cttcagacct gggtgcataa catcacccga ggcaagggca tgggtgacca    1080
cgctttccac acaaatgcca gggatgccct taatgtctcc caggcttggc gctggtcttt    1140
gccctatgaa aagtttctc gacttcagaa agcctgtggc gatgccatga atttgctggg    1200
ctaccgccac gtcagatctg aacaagaaca gagaaacctg ttgctggatc ttctgtctac    1260
ctggactgtc cctgagcaaa tccactaaga gggttgagaa ggctttgctg ccacctggtg    1320
tcagcctcag tcactttctc tgaatgcttc tgagccttgc ctacatctct gagccttaac    1380
tacatgtctg tgggtatcac actgagtgtg agttgtgtcc acacgtgctc aagcagaagg    1440
acttttgtgt ccatgcttgt gtctagaaaa cagactgggg aaccttatgt gagcagcaca    1500
tcccaccagt gaaacagggt attgctcttc ttcttttctt gatcttcctg tctgggcaga    1560
cttcagagac tttgtggcct ggaggcctat aagcacgac acagtatcag tggaattgat    1620
ccataaacct ccctgtccac atcttgccca atggggaatg gatctttcac caaagagctc    1680
accagcattt tccacagaga tgcgaattct gagcccttgg agttcccaat gggattcaag    1740
gaaggaagtg ggaacaaggt tggatgccta cttatgagct tgaccataca gctatcggta    1800
atcagaaata tgaaacaaaa tctctgacaa aagagcaagc tcttaagttc acaaggtgcc    1860
tgggcttgat ttgaatatca tttcccttttg catttttccca ttacatagaa aactttgacc    1920
tgtgaaactt gccatctgtt aatactaaaa ttcccaaata aggttctgtt tagaatgtcc    1980
cttttttatgc ttcttaatta ttagcagtaa atgttcattt ttatgggatc ctaaaaaaaa    2040
``` aaa                                                                      2043

<210> SEQ ID NO 2
<211> LENGTH: 386
<212> TYPE: PRT
<213> ORGANISM: HOMO SAPIENS

<400> SEQUENCE: 2

```
Met Leu Leu Pro Lys Met Lys Leu Leu Phe Leu Val Ser Gln
 1               5                  10                  15

Met Ala Ile Leu Ala Leu Phe Phe His Met Tyr Ser His Asn Ile Ser
                20                  25                  30

Ser Leu Ser Met Lys Ala Gln Pro Glu Arg Met His Val Leu Val Leu
            35                  40                  45

Ser Ser Trp Arg Ser Gly Ser Ser Phe Val Gly Gln Leu Phe Gly Gln
        50                  55                  60

His Pro Asp Val Phe Tyr Leu Met Glu Pro Ala Trp His Val Trp Met
65                  70                  75                  80

Thr Phe Lys Gln Ser Thr Ala Trp Met Leu His Met Ala Val Arg Asp
                85                  90                  95

Leu Ile Arg Ala Val Phe Leu Cys Asp Met Ser Val Phe Asp Ala Tyr
            100                 105                 110

Met Glu Pro Gly Pro Arg Arg Gln Ser Ser Leu Phe Gln Trp Glu Asn
        115                 120                 125

Ser Arg Ala Leu Cys Ser Ala Pro Ala Cys Asp Ile Ile Pro Gln Asp
    130                 135                 140

Glu Ile Ile Pro Arg Ala His Cys Arg Leu Leu Cys Ser Gln Gln Pro
145                 150                 155                 160

Phe Glu Val Val Glu Lys Ala Cys Arg Ser Tyr Ser His Val Val Leu
                165                 170                 175

Lys Glu Val Arg Phe Phe Asn Leu Gln Ser Leu Tyr Pro Leu Leu Lys
            180                 185                 190

Asp Pro Ser Leu Asn Leu His Ile Val His Leu Val Arg Asp Pro Arg
        195                 200                 205

Ala Val Phe Arg Ser Arg Glu Arg Thr Lys Gly Asp Leu Met Ile Asp
    210                 215                 220

Ser Arg Ile Val Met Gly Gln His Glu Gln Lys Leu Lys Lys Glu Asp
225                 230                 235                 240

Gln Pro Tyr Tyr Val Met Gln Val Ile Cys Gln Ser Gln Leu Glu Ile
                245                 250                 255

Tyr Lys Thr Ile Gln Ser Leu Pro Lys Ala Leu Gln Glu Arg Tyr Leu
            260                 265                 270

Leu Val Arg Tyr Glu Asp Leu Ala Arg Ala Pro Val Ala Gln Thr Ser
        275                 280                 285

Arg Met Tyr Glu Phe Val Gly Leu Glu Phe Leu Pro His Leu Gln Thr
    290                 295                 300

Trp Val His Asn Ile Thr Arg Gly Lys Gly Met Gly Asp His Ala Phe
305                 310                 315                 320

His Thr Asn Ala Arg Asp Ala Leu Asn Val Ser Gln Ala Trp Arg Trp
                325                 330                 335

Ser Leu Pro Tyr Glu Lys Val Ser Arg Leu Gln Lys Ala Cys Gly Asp
            340                 345                 350

Ala Met Asn Leu Leu Gly Tyr Arg His Val Arg Ser Glu Gln Glu Gln
        355                 360                 365
```

-continued

Arg Asn Leu Leu Leu Asp Leu Leu Ser Thr Trp Thr Val Pro Glu Gln
    370                 375                 380

Ile His
385

<210> SEQ ID NO 3
<211> LENGTH: 1926
<212> TYPE: DNA
<213> ORGANISM: MOUSE

<400> SEQUENCE: 3

| | | | | | |
|---|---|---|---|---|---|
| gggcatctaa | cttacacttg | gtcagacaag | acaagctttt | gcctacaaag | gccacactct | 60 |
| gtcaggggtg | tagaaaggtg | tggggtgtgg | cagaactccc | tatagtgatt | aaatgtgctg | 120 |
| ggtaggatat | tctcggtggt | ttgatggatg | agaaagccca | gagggtgagt | tttaaagact | 180 |
| tgtaacatag | aatgcagtga | tccaattaag | agccagaatt | actttgcaga | gggatctgga | 240 |
| caaatacttg | caggaatgtt | tttggttttt | gtttgtttgt | ttgtttgttt | tacattgctc | 300 |
| cttggatggg | aatccagaga | agcccgaagg | tagatgctgt | aacaacctaa | ctcagcccca | 360 |
| tcccctctgc | ttgctctttc | aaggtcttct | ccttcttccg | caggatgatg | ctgttgaaga | 420 |
| aagggaggct | gctgatgttc | ctgggttccc | aggtcatcgt | tgtagctctc | ttcatcccata | 480 |
| tgtccgtcca | cagacacctt | tcccagaggg | aggagtccag | gaggcccgtg | catgtgctgg | 540 |
| tgctgtcttc | ctggcggtca | ggatcctctt | ttgtgggaca | gcttttcggg | cagcacccgg | 600 |
| atgtgttcta | cctgatggag | cctgcctggc | atgtgtggat | gactttcacc | agcagcacag | 660 |
| cctggaagct | gcacatggct | gtgcgggatc | ttctgcgttc | cgtcttcctg | tgtgacatga | 720 |
| gcgtctttga | tgcctacatg | aacccaggcc | cccggaaaca | gtccagcctc | ttccagtggg | 780 |
| agcaaagccg | ggccctgtgc | tcagcgcctg | tgtgtgactt | cttccctgcc | cacgagatca | 840 |
| gctcacccaa | gcactgcaag | ctgctctgcg | gtcagcagcc | ctttgatatg | gtggagaagg | 900 |
| cctgccgctc | tcacggcttc | gtggtactca | aggaggtgcg | ttttctcagc | ctgcaggccc | 960 |
| tctatccact | actcacggac | ccttccctca | acctgcacgt | cgtgcacctg | gtccgagacc | 1020 |
| cccgggccgt | gttccgatcc | cgggagcaca | ccaccataga | actcatggtt | gacagtcata | 1080 |
| ttgtgctagg | gcagcatttg | gaaacgatca | aggaggaaga | ccagccctat | tatgccatga | 1140 |
| agatcatctg | caaaagccag | gtggacatag | tcaaggccat | ccaaaccctc | cctgaagctc | 1200 |
| tgcagcagcg | ctacctgttc | ctgaggtatg | aggacctggt | tcgggcaccc | ctggcccaga | 1260 |
| cgaccagact | atataaattt | gtggggttgg | attttttgcc | ccacctccaa | acatgggttt | 1320 |
| acaatgtcac | ccgcggcaag | ggcatgggtc | agcatgcctt | ccatactaac | gccaggaacg | 1380 |
| ccctcaacgt | ctctcaggcg | tggcgttggt | ccttacctta | cgaaaaggtt | tcccagcttc | 1440 |
| aagatgcctg | cggtgaggct | atggatttgc | tgggatacct | ccaggtcaga | tctcaacaag | 1500 |
| aacaaggcaa | cctgtccctg | gatcttctgt | cctcctccca | tatcttgggg | caggtcttcc | 1560 |
| gagaaggtta | aggaggtctg | tctgcacccc | ttggttccag | ccttagtcac | cattaaacgc | 1620 |
| acagaagcct | taaggtataa | ccaaactgag | tgcccctttc | tcctcagccc | caagcagagg | 1680 |
| ggtctttgtg | tctatactca | tgtctaccct | acaactgagc | ctaaaaagcc | aagaaacagt | 1740 |
| atctttctgt | cttgaaaata | cttaggaacc | ttaagcagcc | cctttgacct | gtcaagcaag | 1800 |
| actttcttgt | aaccttggcc | ttcttacctg | tgcatacctt | ggagactcgg | tctggaggca | 1860 |
| tactggacac | agcaaacagc | atctgtggag | tgtgtctgta | aacctccctg | tcacatcttt | 1920 |

-continued tctaag                                                                                                      1926

<210> SEQ ID NO 4
<211> LENGTH: 388
<212> TYPE: PRT
<213> ORGANISM: MOUSE

<400> SEQUENCE: 4

Met Met Leu Leu Lys Lys Gly Arg Leu Leu Met Phe Leu Gly Ser Gln
1               5                   10                  15

Val Ile Val Val Ala Leu Phe Ile His Met Ser Val His Arg His Leu
            20                  25                  30

Ser Gln Arg Glu Glu Ser Arg Arg Pro Val His Val Leu Val Leu Ser
        35                  40                  45

Ser Trp Arg Ser Gly Ser Ser Phe Val Gly Gln Leu Phe Gly Gln His
    50                  55                  60

Pro Asp Val Phe Tyr Leu Met Glu Pro Ala Trp His Val Trp Met Thr
65                  70                  75                  80

Phe Thr Ser Ser Thr Ala Trp Lys Leu His Met Ala Val Arg Asp Leu
                85                  90                  95

Leu Arg Ser Val Phe Leu Cys Asp Met Ser Val Phe Asp Ala Tyr Met
            100                 105                 110

Asn Pro Gly Pro Arg Lys Gln Ser Ser Leu Phe Gln Trp Glu Gln Ser
        115                 120                 125

Arg Ala Leu Cys Ser Ala Pro Val Cys Asp Phe Phe Pro Ala His Glu
    130                 135                 140

Ile Ser Ser Pro Lys His Cys Lys Leu Leu Cys Gly Gln Gln Pro Phe
145                 150                 155                 160

Asp Met Val Glu Lys Ala Cys Arg Ser His Gly Phe Val Val Leu Lys
                165                 170                 175

Glu Val Arg Phe Leu Ser Leu Gln Ala Leu Tyr Pro Leu Leu Thr Asp
            180                 185                 190

Pro Ser Leu Asn Leu His Val Val His Leu Val Arg Asp Pro Arg Ala
        195                 200                 205

Val Phe Arg Ser Arg Glu His Thr Thr Ile Glu Leu Met Val Asp Ser
    210                 215                 220

His Ile Val Leu Gly Gln His Leu Glu Thr Ile Lys Glu Glu Asp Gln
225                 230                 235                 240

Pro Tyr Tyr Ala Met Lys Ile Ile Cys Lys Ser Gln Val Asp Ile Val
                245                 250                 255

Lys Ala Ile Gln Thr Leu Pro Glu Ala Leu Gln Gln Arg Tyr Leu Phe
            260                 265                 270

Leu Arg Tyr Glu Asp Leu Val Arg Ala Pro Leu Ala Gln Thr Thr Arg
        275                 280                 285

Leu Tyr Lys Phe Val Gly Leu Asp Phe Leu Pro His Leu Gln Thr Trp
    290                 295                 300

Val Tyr Asn Val Thr Arg Gly Lys Gly Met Gly Gln His Ala Phe His
305                 310                 315                 320

Thr Asn Ala Arg Asn Ala Leu Asn Val Ser Gln Ala Trp Arg Trp Ser
                325                 330                 335

Leu Pro Tyr Glu Lys Val Ser Gln Leu Gln Asp Ala Cys Gly Glu Ala
            340                 345                 350

Met Asp Leu Leu Gly Tyr Leu Gln Val Arg Ser Gln Gln Glu Gln Gly
        355                 360                 365

-continued

Asn Leu Ser Leu Asp Leu Leu Ser Ser Ser His Ile Leu Gly Gln Val
    370                 375                 380

Phe Arg Glu Gly
385

<210> SEQ ID NO 5
<211> LENGTH: 37
<212> TYPE: DNA
<213> ORGANISM: Artificial Sequence
<220> FEATURE:
<223> OTHER INFORMATION: synthetic primer

<400> SEQUENCE: 5
aaactcaaga aggaggacca accctactat gtgatgc                              37

<210> SEQ ID NO 6
<211> LENGTH: 47
<212> TYPE: DNA
<213> ORGANISM: Artificial Sequence
<220> FEATURE:
<223> OTHER INFORMATION: synthetic primer

<400> SEQUENCE: 6
ataaagcttg tggatttgtt cagggacatt ccaggtagac agaagat                   47

<210> SEQ ID NO 7
<211> LENGTH: 29
<212> TYPE: PRT
<213> ORGANISM: Artificial Sequence
<220> FEATURE:
<223> OTHER INFORMATION: synthetic primer

<400> SEQUENCE: 7

Thr Trp Tyr Thr Trp Tyr Cys Thr Ile Thr Trp Tyr Gly Ala Arg Cys
  1               5                  10                  15

Cys Ile Cys Thr Ile Thr Gly Gly Cys Ala Tyr Ser Thr
              20                  25

<210> SEQ ID NO 8
<211> LENGTH: 59
<212> TYPE: DNA
<213> ORGANISM: Artificial Sequence
<220> FEATURE:
<223> OTHER INFORMATION: synthetic primer

<400> SEQUENCE: 8
caagagtgtt ttctaaatac agtattgtag aaagtaattg ccaatagcat gagtctgga      59

<210> SEQ ID NO 9
<211> LENGTH: 59
<212> TYPE: DNA
<213> ORGANISM: Artificial Sequence
<220> FEATURE:
<223> OTHER INFORMATION: synthetic primer

<400> SEQUENCE: 9
taaacctatg gaatgaataa aggcatgctt gacaaaaagt catatccaga ctcatgcta     59

<210> SEQ ID NO 10
<211> LENGTH: 30
<212> TYPE: DNA
<213> ORGANISM: Artificial Sequence
<220> FEATURE:
<223> OTHER INFORMATION: synthetic primer

<400> SEQUENCE: 10

-continued agtcatgtgg ccatcaagac tgtgcgggtg                30

<210> SEQ ID NO 11
<211> LENGTH: 30
<212> TYPE: DNA
<213> ORGANISM: Artificial Sequence
<220> FEATURE:
<223> OTHER INFORMATION: synthetic primer

<400> SEQUENCE: 11
gggagataag gcaacagtta aagacggccc                30

<210> SEQ ID NO 12
<211> LENGTH: 32
<212> TYPE: DNA
<213> ORGANISM: Artificial Sequence
<220> FEATURE:
<223> OTHER INFORMATION: synthetic primer

<400> SEQUENCE: 12
catgggtcag catgccttcc atactaacgc ca              32

<210> SEQ ID NO 13
<211> LENGTH: 32
<212> TYPE: DNA
<213> ORGANISM: Artificial Sequence
<220> FEATURE:
<223> OTHER INFORMATION: synthetic primer

<400> SEQUENCE: 13
ctctgcttgg ggctgaggag aaagggcac tc              32

<210> SEQ ID NO 14
<211> LENGTH: 33
<212> TYPE: DNA
<213> ORGANISM: Artificial Sequence
<220> FEATURE:
<223> OTHER INFORMATION: synthetic primer

<400> SEQUENCE: 14
gcctaccgca aggaggtcgt cggactggtg gac            33

<210> SEQ ID NO 15
<211> LENGTH: 33
<212> TYPE: DNA
<213> ORGANISM: Artificial Sequence
<220> FEATURE:
<223> OTHER INFORMATION: synthetic primer

<400> SEQUENCE: 15
actgttaacc cgctcatagc ccagcacggc cat            33

<210> SEQ ID NO 16
<211> LENGTH: 25
<212> TYPE: DNA
<213> ORGANISM: Artificial Sequence
<220> FEATURE:
<223> OTHER INFORMATION: synthetic primer

<400> SEQUENCE: 16
cctgctggat tacatcaaag cactg                     25

<210> SEQ ID NO 17
<211> LENGTH: 21
<212> TYPE: DNA

```
<213> ORGANISM: Artificial Sequence
<220> FEATURE:
<223> OTHER INFORMATION: synthetic primer

<400> SEQUENCE: 17
tccaacactt cgtggggtcc t                                              21

<210> SEQ ID NO 18
<211> LENGTH: 28
<212> TYPE: PRT
<213> ORGANISM: Homo Sapiens

<400> SEQUENCE: 18

Trp Arg Ser Gly Ser Ser Phe Val Gly Gln Leu Phe Gly Gln His Pro
 1               5                  10                  15

Asp Val Phe Tyr Leu Met Glu Pro Ala Trp His Val
            20                  25

<210> SEQ ID NO 19
<211> LENGTH: 29
<212> TYPE: PRT
<213> ORGANISM: Homo Sapiens

<400> SEQUENCE: 19

Thr Trp Arg Ser Gly Ser Ser Phe Phe Gly Glu Leu Phe Asn Gln Asn
 1               5                  10                  15

Pro Glu Val Phe Phe Leu Tyr Glu Pro Val Trp His Val
            20                  25

<210> SEQ ID NO 20
<211> LENGTH: 29
<212> TYPE: PRT
<213> ORGANISM: Homo Sapiens

<400> SEQUENCE: 20

Thr Thr Arg Ser Gly Ser Ser Phe Val Gly Gln Leu Phe Asn Gln His
 1               5                  10                  15

Leu Asp Val Phe Tyr Leu Phe Glu Pro Leu Tyr His Val
            20                  25

<210> SEQ ID NO 21
<211> LENGTH: 29
<212> TYPE: PRT
<213> ORGANISM: Homo Sapiens

<400> SEQUENCE: 21

Thr Thr Arg Thr Gly Ser Ser Phe Val Gly Glu Phe Phe Asn Gln Gln
 1               5                  10                  15

Gly Asn Ile Phe Tyr Leu Phe Glu Pro Leu Trp His Ile
            20                  25

<210> SEQ ID NO 22
<211> LENGTH: 22
<212> TYPE: PRT
<213> ORGANISM: Homo Sapiens

<400> SEQUENCE: 22

Asp Pro Ser Leu Asn Leu His Ile Val His Leu Val Arg Asp Pro Arg
 1               5                  10                  15

Ala Val Phe Arg Ser Arg
            20
```

<210> SEQ ID NO 23
<211> LENGTH: 22
<212> TYPE: PRT
<213> ORGANISM: Homo Sapiens

<400> SEQUENCE: 23

Asp Pro Ala Leu Asp Leu Lys Val Ile His Leu Val Arg Asp Pro Arg
1               5                   10                  15

Ala Val Ala Ser Ser Arg
            20

<210> SEQ ID NO 24
<211> LENGTH: 22
<212> TYPE: PRT
<213> ORGANISM: Homo Sapiens

<400> SEQUENCE: 24

Asp Pro Arg Leu Asn Leu Lys Val Leu Gln Leu Val Arg Asp Pro Arg
1               5                   10                  15

Gly Ile Leu Ala Ser Arg
            20

<210> SEQ ID NO 25
<211> LENGTH: 22
<212> TYPE: PRT
<213> ORGANISM: Homo Sapiens

<400> SEQUENCE: 25

Asp Pro Arg Leu Asp Leu Arg Val Ile Gln Leu Val Arg Asp Pro Arg
1               5                   10                  15

Ala Val Leu Ala Ser Arg
            20

<210> SEQ ID NO 26
<211> LENGTH: 20
<212> TYPE: PRT
<213> ORGANISM: Homo Sapiens

<400> SEQUENCE: 26

Pro Lys Ala Leu Gln Glu Arg Tyr Leu Leu Val Arg Tyr Glu Asp Leu
1               5                   10                  15

Ala Arg Ala Pro
            20

<210> SEQ ID NO 27
<211> LENGTH: 20
<212> TYPE: PRT
<213> ORGANISM: Homo Sapiens

<400> SEQUENCE: 27

Pro Asp Trp Leu Gln Gly His Tyr Leu Val Val Arg Tyr Glu Asp Leu
1               5                   10                  15

Val Gly Asp Pro
            20

<210> SEQ ID NO 28
<211> LENGTH: 20
<212> TYPE: PRT
<213> ORGANISM: Homo Sapiens

<400> SEQUENCE: 28

Pro Pro Trp Leu Lys Gly Lys Tyr Met Leu Val Arg Tyr Glu Asp Leu
1               5                   10                  15

```
Ala Arg Asn Pro
        20

<210> SEQ ID NO 29
<211> LENGTH: 20
<212> TYPE: PRT
<213> ORGANISM: Homo Sapiens

<400> SEQUENCE: 29

Pro Ala Trp Leu Arg Gly Arg Tyr Met Leu Val Arg Tyr Glu Asp Val
1               5                  10                  15

Ala Arg Gly Pro
        20

<210> SEQ ID NO 30
<211> LENGTH: 29
<212> TYPE: PRT
<213> ORGANISM: Artificial Sequence
<220> FEATURE:
<223> OTHER INFORMATION: synthetic primer

<400> SEQUENCE: 30

Cys Thr Ile Ala Ala Ile Cys Thr Ile Ser Thr Ile Cys Trp Arg Cys
1               5                  10                  15

Thr Ile Ser Thr Ile Met Gly Ile Arg Ala Tyr Cys Cys
            20                  25

<210> SEQ ID NO 31
<211> LENGTH: 29
<212> TYPE: PRT
<213> ORGANISM: Artificial Sequence
<220> FEATURE:
<223> OTHER INFORMATION: synthetic primer

<400> SEQUENCE: 31

Gly Gly Arg Thr Tyr Ile Cys Lys Ile Ala Ser Ile Ala Gly Tyr Trp
1               5                  10                  15

Gly Ile Ala Ser Ile Ala Gly Ile Thr Thr Ile Ala Gly
            20                  25

<210> SEQ ID NO 32
<211> LENGTH: 26
<212> TYPE: PRT
<213> ORGANISM: Artificial Sequence
<220> FEATURE:
<223> OTHER INFORMATION: synthetic primer

<400> SEQUENCE: 32

Ala Gly Arg Thr Cys Tyr Thr Cys Arg Thr Ala Ile Cys Lys Ile Ala
1               5                  10                  15

Gly Ile Ala Gly Ile Ala Lys Arg Thr Ala
            20                  25

<210> SEQ ID NO 33
<211> LENGTH: 29
<212> TYPE: PRT
<213> ORGANISM: Homo Sapiens
<220> FEATURE:
<221> NAME/KEY: PEPTIDE
<222> LOCATION: 1
<223> OTHER INFORMATION: Xaa = Thr or Ser
<220> FEATURE:
<221> NAME/KEY: PEPTIDE
<222> LOCATION: 2
<223> OTHER INFORMATION: Xaa = any amino acid
```

```
<220> FEATURE:
<221> NAME/KEY: PEPTIDE
<222> LOCATION: 9
<223> OTHER INFORMATION: Xaa = Val or Phe
<220> FEATURE:
<221> NAME/KEY: PEPTIDE
<222> LOCATION: 11
<223> OTHER INFORMATION: Xaa = Gln or Glu
<220> FEATURE:
<221> NAME/KEY: PEPTIDE
<222> LOCATION: 14
<223> OTHER INFORMATION: Xaa = any amino acid
<220> FEATURE:
<221> NAME/KEY: PEPTIDE
<222> LOCATION: 16
<223> OTHER INFORMATION: Xaa = any amino acid
<220> FEATURE:
<221> NAME/KEY: PEPTIDE
<222> LOCATION: (17)...(17)
<223> OTHER INFORMATION: Xaa = Pro or Leu
<220> FEATURE:
<221> NAME/KEY: PEPTIDE
<222> LOCATION: (18)...(18)
<223> OTHER INFORMATION: Xaa = Asp or Glu
<220> FEATURE:
<221> NAME/KEY: PEPTIDE
<222> LOCATION: (21)...(21)
<223> OTHER INFORMATION: Xaa = Phe or Tyr
<220> FEATURE:
<221> NAME/KEY: PEPTIDE
<222> LOCATION: (23)...(23)
<223> OTHER INFORMATION: Xaa = Phe, Tyr or Met
<220> FEATURE:
<221> NAME/KEY: PEPTIDE
<222> LOCATION: (26)...(26)
<223> OTHER INFORMATION: Xaa = Leu, Val or Ala
<220> FEATURE:
<221> NAME/KEY: PEPTIDE
<222> LOCATION: (27)...(27)
<223> OTHER INFORMATION: Xaa = Trp or Tyr

<400> SEQUENCE: 33

Xaa Xaa Arg Ser Gly Ser Ser Phe Xaa Gly Xaa Leu Phe Xaa Gln Xaa
 1               5                  10                  15
Xaa Xaa Val Phe Xaa Leu Xaa Glu Pro Xaa Xaa His Val
            20                  25

<210> SEQ ID NO 34
<211> LENGTH: 16
<212> TYPE: PRT
<213> ORGANISM: Homo Sapiens
<220> FEATURE:
<221> NAME/KEY: PEPTIDE
<222> LOCATION: 2
<223> OTHER INFORMATION: Xaa = Asn or Asp
<220> FEATURE:
<221> NAME/KEY: PEPTIDE
<222> LOCATION: 4
<223> OTHER INFORMATION: Xaa = Lys or His
<220> FEATURE:
<221> NAME/KEY: PEPTIDE
<222> LOCATION: 5
<223> OTHER INFORMATION: Xaa = Val or Ile
<220> FEATURE:
<221> NAME/KEY: PEPTIDE
<222> LOCATION: 6
<223> OTHER INFORMATION: Xaa = Ile or Val
<220> FEATURE:
<221> NAME/KEY: PEPTIDE
<222> LOCATION: 7
<223> OTHER INFORMATION: Xaa = any amino acid
<220> FEATURE:
<221> NAME/KEY: PEPTIDE
<222> LOCATION: 14
<223> OTHER INFORMATION: Xaa = Ala or Gly
<220> FEATURE:
```

-continued

```
<221> NAME/KEY: PEPTIDE
<222> LOCATION: (15)...(15)
<223> OTHER INFORMATION: Xaa = Val or Ile
<220> FEATURE:
<221> NAME/KEY: PEPTIDE
<222> LOCATION: (16)...(16)
<223> OTHER INFORMATION: Xaa = Leu or Ala or Phe

<400> SEQUENCE: 34

Leu Xaa Leu Xaa Xaa Xaa Xaa Leu Val Arg Asp Pro Arg Xaa Xaa Xaa
 1               5                  10                  15

<210> SEQ ID NO 35
<211> LENGTH: 20
<212> TYPE: PRT
<213> ORGANISM: Homo Sapiens
<220> FEATURE:
<221> NAME/KEY: PEPTIDE
<222> LOCATION: 2
<223> OTHER INFORMATION: Xaa = Any Amino Acid
<220> FEATURE:
<221> NAME/KEY: PEPTIDE
<222> LOCATION: 3
<223> OTHER INFORMATION: Xaa = Any Amino Acid
<220> FEATURE:
<221> NAME/KEY: PEPTIDE
<222> LOCATION: 5
<223> OTHER INFORMATION: Xaa = Gln or Lys
<220> FEATURE:
<221> NAME/KEY: PEPTIDE
<222> LOCATION: 6
<223> OTHER INFORMATION: Xaa = Any Amino Acid
<220> FEATURE:
<221> NAME/KEY: PEPTIDE
<222> LOCATION: 7
<223> OTHER INFORMATION: Xaa = Any Amino Acid
<220> FEATURE:
<221> NAME/KEY: PEPTIDE
<222> LOCATION: 9
<223> OTHER INFORMATION: Xaa = Leu or Met
<220> FEATURE:
<221> NAME/KEY: PEPTIDE
<222> LOCATION: (10)...(10)
<223> OTHER INFORMATION: Xaa = Leu or Val
<220> FEATURE:
<221> NAME/KEY: PEPTIDE
<222> LOCATION: (17)...(17)
<223> OTHER INFORMATION: Xaa = Ala or Val
<220> FEATURE:
<221> NAME/KEY: PEPTIDE
<222> LOCATION: (18)...(18)
<223> OTHER INFORMATION: Xaa = Any Amino Acid
<220> FEATURE:
<221> NAME/KEY: PEPTIDE
<222> LOCATION: (19)...(19)
<223> OTHER INFORMATION: Xaa = Any Amino Acid

<400> SEQUENCE: 35

Pro Xaa Xaa Leu Xaa Xaa Xaa Tyr Xaa Xaa Val Arg Tyr Glu Asp Leu
 1               5                  10                  15

Xaa Xaa Xaa Pro
            20
```

HEC-G1CNAC6ST

CROSS-REFERENCE TO RELATED APPLICATIONS

This application is a continuation-in-part of application Ser. No. PCT/US99/04316 filed Feb. 26, 1999; which application is a continuation-in-part of application Ser. No. 09/190,911 filed Nov. 12, 1998, now U.S. Pat. No. 6,365,365 which application is a continuation-in-part of application Ser. No. 09/045,284 filed on Mar. 20, 1998, now U.S. Pat. No. 6,265,192 the disclosures of which are herein incorporated by reference.

INTRODUCTION

1. Field of the Invention

The field of the invention is cell adhesion, particularly selectin mediated cell adhesion, as well as the treatment of disease conditions related thereto.

2. Background of the Invention

Sulfotransferases are enzymes that catalyze the transfer of a sulfate from a donor compound to an acceptor compound, usually placing the sulfate moiety at a specific location on the acceptor compound. There are a variety of different sulfotransferases which vary in activity, i.e. with respect to the donor and/or acceptor compounds with which they work. Known sulfotransferases include those acting on carbohydrate: heparin/heparan sulfate N-sulfotransferase (NST); chondroitin 6/keratan 6 sulfate sulfotransferase (C6ST/KSST); galactosylceramide 3'-sulfotransferase; heparan sulfate 2-sulfotransferase (Iduronic acid); HNK-1 sulfotransferase (3-glucuronic acid); heparan sulfate D-glucosamino 3-O-sulfotransferase (3-OST);etc., as well as those acting on phenols, steroids and xenobiotics: aryl sulfotransferase I & II, hydroxy-steroid sulfotransferases I, II & III, dehydroepiandrosterone (DHEA); etc. Sulfotransferases play a central role in a variety of different biochemical mechanisms, as the presence of a sulfate moiety on a particular ligand is often required for a particular activity, e.g. binding.

The presence of a sulfate moiety on selectin ligands has been shown to be important for selectin binding to occur. See Imai et al., Nature (1993) 361:555–557 and Imai et al., Glycoconjugate J. (1993) 10:34–39, as well as U.S. Pat. No. 5,695,752. Several selectin ligands have, to date, been identified. The L-selectin endothelial ligands in mouse that have been identified arc: CD34, GlyCAM-1, MAdCAM-1 and sgp200. In addition, PSGL-1 has been identified as a leukocyte ligand for P-, E-, and L-selectin. Endothelial ligands for L-selectin in humans are still poorly defined, but include CD34 and podocalyxin.

Selectin mediated binding plays an important and prominent role in a variety of biological processes. Selectins are lectin like cell adhesion molecules that mediate leukocyte-endothelial, leukocyte-leukocyte, leukocyte-platelet, platelet-endothelial and platelet-platelet interactions. One critical biological process in which selectin mediated binding plays a role is the maintenance of immune surveillance.

Maintenance of immune surveillance depends on the constant recirculation of lymphocytes from the blood through the vascular wall into the tissues and eventually back into the blood. Lymphocyte recruitment from the blood into all secondary lymphoid organs (except the spleen) as well as into many sites of chronic inflammation is mediated by a specialized postcapillary venule called a high endothelial venule. These vessels are defined by the distinct, cuboidal morphology of their endothelial cells and their luminal presentation of ligands for the leukocyte adhesion molecule, L-selectin. This lectin-like adhesion molecule is expressed on all classes of leukocytes in the blood and is responsible for the initial tethering and rolling of a leukocyte on the endothelium prior to subsequent integrin mediated firm arrest and transmigration.

Although selectin mediated binding events play a critical role in normal physiological processes, disease conditions do exist for which it is desired to regulate or modulate, e.g. limit or prevent, the amount of selectin mediated binding that occurs. Such conditions include: acute or chronic inflammation; autoimmune and related disorders, tissue rejection during transplantation, and the like.

As the above conditions all result from selectin mediated binding events, there is great interest in the elucidation of the mechanisms underlying such binding events. There is also great interest in the identification of treatment methodologies for these and related disease conditions, as well the identification of active agents for use therein.

As such, there is continued interest in the identification of participants in the selectin binding mechanism, including enzymatic agents, and the elucidation of their role(s) in selectin mediated binding events, as well as the development of therapies for disease conditions arising from such binding events.

Relevant Literature

Chondroitin-6-sulfotransferase is disclosed in EP 821 066, as well as in Fukuta et al., "Molecular Cloning and Characterization of Human Keratan Sulfate Gal-6-Sulfotransferase," J. Biol. Chem. (Dec. 19, 1997) 272: 32321–32328; Habuchi et al., "Enzymatic Sulfation of Galactose Residue of Keratan Sulfate by Chondroitin 6-Sulfotransferase," Glycobiology (January 1996) 6:51–57; Habuchi et al., "Enzymatic Sulfation of Galactose Residue of Keratan Sulfate by Chondroitin 6-Sulfate by Chondroitin 6-Sulfotransferase," Glycobiology (January 1996) 6:51–57; Fukuta et al., "Molecular Cloning and Expression of Chick Chondrocyte Chondroitin 6-Sulfotuansferase," J. Biol. Chem. (1995) 270: 18575–18580; and Habuchi et al., "Purification of Chondroitin 6-Sulfotransferase Secreted from Cultured Chick Embryo Chondrocytes," J. Biol. Chem. (1993) 268: 21968–21974.

References providing background information on selectin mediated binding include: Baumhueter et al., "Binding of L-Selectin to the Vascular Sialomucin CD34," Science (Oct. 15, 1993): 436–438; Boukerche et al., "A Monoclonal Antibody Directed Against a Granule Membrane Glycoprotein (GMP-140/PADGEM, P-selectin, CD62P) Inhibits Ristocetin-Induced Platelet Aggregation," Br. J. Haematology (1996) 92: 442–451; Celi et al., "Platelet-Leukocyte-Endothelial Cell Interaction on the Blood Vessel Wall," Seminars in Hematology (1997) 34: 327–335; Frenette et al., "Platelets Roll on Stimulated Endothelium In Vivo: An Interaction Mediated by Endothelial P-selectin," Proc. Natl. Acad. Sci. USA (August 1995) 52:7450–7454; Girard & Springer, "High Endothelial Venules (HEVs): Specialized Endothelium for Lymphocyte Migration," Immun. Today (1995) 16: 449–457; Hemmerich et al., "Sulfation Dependent Recognition of High Endothelial Venules (HEV)-Ligands by L-Selectin and Meca79, an Adhesion-Blocking Monoclonal Antibody," J. Exp. Medicine (December 1994) 180: 2219–2226; 262 Lasky et al., "-Endothelial Ligand for L-Selectin Is a Mucin-Like Molecule," Cell (Jun. 12, 1992) 69:927–938; Rosen & Bertozzi, "The Selectins and Their Ligands," Current Opinion in Cell Biology (1994) 6: 663–673; and Sawada et al., "Specific Expression of a Complex Sialyl Lewis X Antigen On High Endothelial Venules of Human Lymph Nodes: Possible Candidate for L-selectin Ligand," Biochem. Biophys. Res. Comm. (May 28, 1993) 193: 337–347; as well as U.S. Pat. No. 5,580,862.

U.S. Pat. No. 5,695,752 describes methods of treating inflammation through administration of sulfation inhibitors.

SUMMARY OF THE INVENTION

A mammalian glycosyl sulfotransferase HEC-GLCNAC6ST or GST-3) and polypeptides related thereto, as well as nucleic acid compositions encoding the same, are provided. The subject polypeptide and nucleic acid compositions find use in a variety of applications, including diagnostic and therapeutic agent screening applications, as well as in treatment therapies. Also provided are methods of inhibiting selectin mediated binding events and methods of treating disease conditions associated therewith, particularly by administering inhibitors of HEC-GLCNAC6ST and/or KSGal6ST (or an HEC specific homologue thereof).

BRIEF DESCRIPTION OF THE FIGURES

FIG. 1 provides the sequence of a cDNA containing an open reading frame encoding hu HEC-GLCNAC6ST. The cDNA sequence is SEQ ID NO:01.

FIG. 2 provides the amino acid sequence of hu HEC-GLCNAC6ST. (SEQ ID NO:02).

FIG. 3 provides the sequence of a cDNA containing an open reading frame encoding mouse HEC-GlcNAc6ST. The cDNA sequence is SEQ ID NO:03.

FIG. 4 provides the amino acid sequence of murine HEC-GlcNAc6ST. (SEQ ID NO:04).

FIG. 6 provides the alignment of regions of high conservation among human carbohydrate 6-sulfotransferases (Gal-6, GlcNAc-6 and GalNAc-6). Protein sequences were aligned using the ClustalW algorithm (Thompson et al., 1994, supra). Black shading indicates identity at that residue among at least three of the sequences, grey shading indicates similarity.

DETAILED DESCRIPTION OF THE INVENTION

Figure 5:
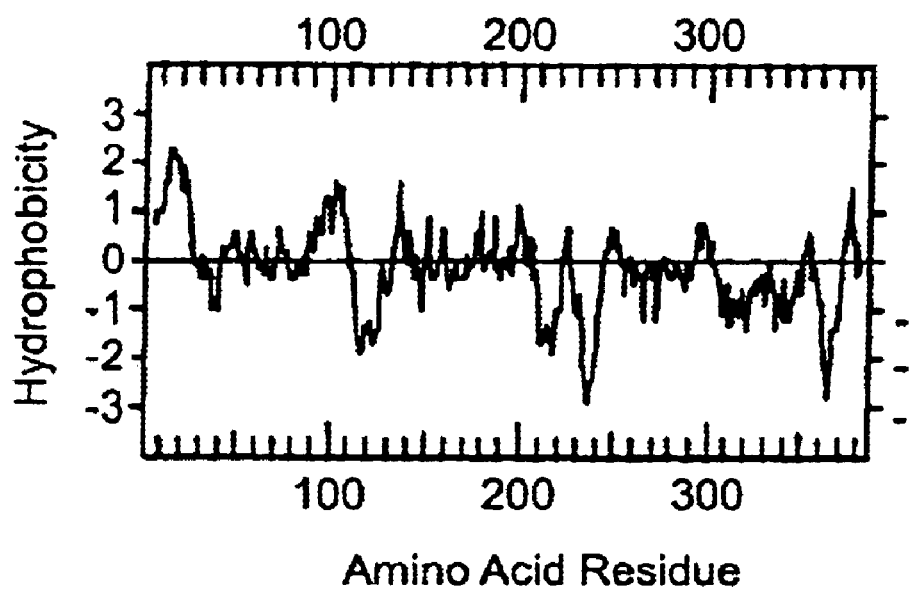
FIG. 5 provides the hydropathy plot for HEC-GlcNAc6ST. The hydrophobicity was calculated by the method of Kyte and Doolittle J. Mol. Biol. (1982) 157, 105–32; using a window of 11 amino acids.

A mammalian glycosyl transferase expressed in high endothelial cells (HEC) (i.e. GST-3 or HEC-GlcNAc6ST) and polypeptides related thereto, as well as nucleic acid compositions encoding the same, are provided. The subject polypeptide and/or nucleic acid compositions find use in a variety of different applications, including diagnostic and therapeutic agent screening/discovery/preparation applications. Also provided are methods of inhibiting selectin mediated binding events and methods of treating disease conditions associated therewith, particularly by administering an inhibitor of HEC-GLCNAC6ST and/or KSGal6ST, or an HEC specific homologue thereof.

Before the subject invention is further described, it is to be understood that the invention is not limited to the particular embodiments of the invention described below, as variations of the particular embodiments may be made and still fall within the scope of the appended claims. It is also to be understood that the terminology employed is for the purpose of describing particular embodiments, and is not intended to be limiting. Instead, the scope of the present invention will be established by the appended claims.

In this specification and the appended claims, the singular forms "a," "an," and "the" include plural reference unless the context clearly dictates otherwise. Unless defined otherwise, all technical and scientific terms used herein have the same meaning as commonly understood to one of ordinary skill in the art to which this invention belongs.

Polypeptide Compositions

Mammalian glycosylsulfotransferases expressed in high endothelial cells (HEC), as well as polypeptide compositions related thereto, are provided. The term polyeptide composition as used herein refers to both the full length human protein as well as portions or fragments thereof. Also included in this term are variations of the naturally occurring human protein, where such variations are homologous or substantially similar to the naturally occurring protein, as described in greater detail below, as well as corresponding homologs from non-human species, such as other mammalian species, e.g. mouse. In the following description of the subject invention, the terms HEC-GlcNAc6ST are used to refer not only to the human form of this sulfotransferase, but also to homologs thereof expressed in non-human species, e.g. mouse HEC-GlcNAc6ST.

The mammalian glycosylsulfotransferase enzyme of the subject invention has been named HEC-GlcNAc6ST (as well as glycosyl sulfotransferase-3 (GST-3)). The mammalian enzyme is a type 2 membrane protein having a relatively short transmembrane domain and a short amino-terminal cytoplasmic tail. huHEC-GLCNAC6ST (the human form of this enzyme) has a 31% amino acid sequence identity with CS6T/KSST (Habuchi et al., J. Biol. Chem. (1995) 240:4172–4179) as measured by using the "GAP" program (part of the Wisconsin Sequence Analysis Package available through the Genetics Computer Group, Inc. (Madison Wis.)), where the parameters are: Gap weight:12; length weight:4.

HEC-GLCNAC6ST is capable of sulfating selectin ligands, particularly L-selectin ligands, e.g. GlyCAM-1. By sulfating selectin ligands is meant that HEC-GLCNAC6ST is capable of catalyzing the transfer of a sulfate group from a donor compound to a position on a selectin ligand precursor as acceptor compound. Donor compounds from which HEC-GLCNAC6ST obtains sulfate groups for transfer to acceptor ligand compounds include 3'-phosphoadenosine 5'-phosphosulfate (PAPS) and the like. Selectin ligands capable of being sulfated through HEC-GLCNAC6ST action include E-, P- and L-selectin ligands, particularly L-selectin ligands, such as GlyCAM-1, CD34, MAdCAM-1, Sgp200, podocalyxin, and the like. HEC-GLCNAC6ST is strongly predicted to have GlcNAc6-0-sulfotransferase (N-actylglucosamine-6-O-sulfotransferase) activity.

Human HEC-GLCNAC6ST is a 386 amino acid protein having an amino acid sequence as shown in FIG. 2 and identified as SEQ ID NO:02. huHEC-GLCNAC6ST has a molecular weight based on its amino acid of about 45 kDa to 46 kDa, and more specifically from about 45100 to 45200 dalton, and specifically 45104 dalton (using DNA Strider 1.2 software). Since HEC-GLCNAC6ST is glycosylated, its true molecular weight is greater, and is likely to be in the range from about 45 to 85 kDa, and more likely from about 50 kDa to 65 kDa. Expression of HEC-GLCNAC6ST in humans is highly restricted. For example, huHEC-GLCNAC6ST is expressed in HEC but not tonsillar lymphocytes, or primary cultured human umbilical vein endothelial cells (HUVEC). Mouse HEC-GlcNAc6ST is a 388 amino acid protein having an amino acid sequence as shown in FIG. 4 and identified as SEQ ID NO:04.

In addition to the subject HEC-GLCNAC6ST proteins, also provided are HEC-GLCNAC6ST proteins that have the same expression pattern in humans as huHEC-GLCNAC6ST, i.e. are highly restricted and expressed in HEC but not HUVEC or lymphocytes. HEC-GLCNAC6ST homologs or proteins (or fragments thereof) from nonhuman species are also provided, including mammals, such as: rodents, e.g. mice, rats; domestic animals, e.g. horse, cow, dog, cat; and humans, as well as non-mammalian species, e.g. avian, and the like. By homolog is meant a protein having at least about 35%, usually at least about 40% and more usually at least about 60% amino acid sequence identity to the human or mouse HEC-GLCNAC6ST proteins of the subject invention.

Also provided are HEC-GLCNAC6ST proteins that are substantially identical to the human or mouse HEC-GLCNAC6ST proteins of the subject invention, where by substantially identical is meant that the protein has an amino acid sequence identity to the sequence of human or mouse HEC-GLCNAC6ST of at least about 35%, usually at least about 40% and more usually at least about 60%.

Also provided are KSGal6ST homologues that are selectively expressed in HEC. The nucleotide and amino acid sequence for KSGal6ST is reported in Fukuta et al., J. Biol. Chem. (Dec. 19, 1997) 272:32321–32328. The subject HEC specific KSGal6ST homologues have a sequence that is substantially identical to KSGal6ST, where by substantially identical is meant that the protein has an amino acid sequence identity to the sequence of KSGal6ST of at least about 35%, usually at least about 40% and more usually at least about 60%.

The proteins of the subject invention (e.g. huHEC-GLCNAC6ST or a homolog thereof; mouse HEC-GLCNAC6ST or a homolog thereof; an HEC specific KSGal6ST homologue) are present in a non-naturally occurring environment, e.g. are separated from their naturally occurring environment. In certain embodiments, the subject proteins are present in a composition that is enriched for subject protein as compared to its naturally occurring environment. For example, purified HEC-GLCNAC6ST is provided, where by purified is meant that HEC-GLCNAC6ST is present in a composition that is substantially free of non-HEC-GLCNAC6ST proteins, where by substantially free is meant that less than 90%, usually less than 60% and more usually less than 50% of the composition is made up of non-HEC-GLCNAC6ST proteins. The proteins of the subject invention may also be present as an isolate, by which is meant that the protein is substantially free of other proteins and other naturally occurring biologic molecules, such as oligosaccharides, polynucleotides and fragments thereof, and the like, where substantially free in this instance means that less than 70%, usually less than 60% and more usually less than 50% of the composition containing the isolated protein is some other naturally occurring biological molecule. In certain embodiments, the proteins are present in substantially pure form, where by substantially pure form is meant at least 95%, usually at least 97% and more usually at least 99% pure.

In addition to the naturally occurring proteins, polypeptides which vary from the naturally occurring proteins are also provided, e.g. HEC-GLCNAC6ST polypeptides. By HEC-GLCNAC6ST polypeptide is meant an amino acid sequence encoded by an open reading frame (ORF) of the HEC-GLCNAC6ST gene, described in greater detail below, including the full length HEC-GLCNAC6ST protein and fragments thereof, particularly biologically active fragments and/or fragments corresponding to functional domains, e.g. acceptor binding site (postulated to be the most 5' consensus region A (see experimental section infra), the donor binding site, e.g. VRYEDL, and the like; and including fusions of the subject polypeptides to other proteins or parts thereof. Fragments of interest will typically be at least about 10 aa in length, usually at least about 50 aa in length, and may be as long as 300 aa in length or longer, but will usually not exceed about 1000 aa in length, where the fragment will have a stretch of amino acids that is identical to the subject protein of at least about 10 aa, and usually at least about 15 aa, and in many embodiments at least about 50 aa in length.

The subject proteins and polypeptides may be obtained from naturally occurring sources or synthetically produced. Where obtained from naturally occurring sources, the source chosen will generally depend on the species from which the protein is to be derived. For example, huHEC-GLCNAC6ST is generally derived from endothelial cells of high endothelial venules (HEV) of human secondary lymphoid organs, such as tonsils. The subject proteins may also be derived from synthetic means, e.g. by expressing a recombinant gene encoding protein of interest in a suitable host, as described in greater detail below. Any convenient protein purification procedures may be employed, where suitable protein purification methodologies are described in Guide to Protein Purification, (Deuthser ed.) (Academic Press, 1990). For example, a lysate may be prepared from the original source, e.g. HEC or the expression host, and purified using HPLC, exclusion chromatography, gel electrophoresis, affinity chromatography, and the like.

Nucleic Acid Compositions

Also provided are nucleic acid compositions encoding HEC-GLCNAC6ST proteins or fragments thereof, as well as the HEC-specific KSGal6ST homologues of the present invention. By HEC-GLCNAC6ST nucleic acid composition is meant a composition comprising a sequence of DNA having an open reading frame that encodes HEC-GLCNAC6ST, i.e. a HEC-GLCNAC6ST gene, and is capable, under appropriate conditions, of being expressed as HEC-GLCNAC6ST. Also encompassed in this term are nucleic acids that are homologous or substantially similar or identical to the nucleic acids encoding HEC-GLCNAC6ST proteins. Thus, the subject invention provides genes encoding huHEC-GLCNAC6ST and homologs thereof. The human HEC-GLCNAC6ST open reading frame/coding sequence is present in the cDNA sequence shown in FIG. 1 and identified as SEQ ID NO:01, infra. The subject invention also provides nucleic acids having a sequence encoding mouse HEC-GLCNAC6ST and homologs thereof. The mouse HEC-GlcNAc6ST coding sequence/open reading frame is present in the cDNA sequence shown in FIG. 3 and identified as SEQ ID NO:03, infra.

The source of homologous genes may be any species, e.g., primate species, particularly human; rodents, such as rats and mice, canines, felines, bovines, ovines, equines, yeast, nematodes, etc. Between mammalian species, e.g., human and mouse, homologs have substantial sequence similarity, e.g. at least 75% sequence identity, usually at least 90%, more usually at least 95% between nucleotide sequences. Sequence similarity is calculated based on a reference sequence, which may be a subset of a larger sequence, such as a conserved motif, coding region, flanking region, etc. A reference sequence will usually be at least about 18 nt long, more usually at least about 30 nt long, and may extend to the complete sequence that is being compared. Algorithms for sequence analysis are known in the art, such as BLAST, described in Altschul et al. (1990), *J. Mol. Biol.* 215:403–10 (using default settings). The sequences provided herein are essential for recognizing HEC-GLCNAC6ST-related and homologous proteins in database searches.

Nucleic acids encoding the HEC-GLCNAC6ST protein and HEC-GLCNAC6ST polypeptides of the subject invention may be cDNA or genomic DNA or a fragment thereof. The term "HEC-GLCNAC6ST gene" shall be intended to mean the open reading frame encoding specific HEC-GLCNAC6ST proteins and polypeptides, and HEC-GLCNAC6ST introns, as well as adjacent 5' and 3' non-coding nucleotide sequences involved in the regulation of expression, up to about 20 kb beyond the coding region, but possibly further in either direction. The gene may be introduced into an appropriate vector for extrachromosomal maintenance or for integration into a host genome.

The term "cDNA" as used herein is intended to include all nucleic acids that share the arrangement of sequence elements found in native mature mRNA species, where sequence elements are exons and 3' and 5' non-coding regions. Normally mRNA species have contiguous exons, with the intervening introns, when present, being removed by nuclear RNA splicing, to create a continuous open reading frame encoding a HEC-GLCNAC6ST protein.

A genomic sequence of interest comprises the nucleic acid present between the initiation codon and the stop codon, as defined in the listed sequences, including all of the introns that are normally present in a native chromosome. It may further include the 3' and 5' untranslated regions found in the mature mRNA. It may further include specific transcriptional and translational regulatory sequences, such as promoters, enhancers, etc., including about 1 kb, but possibly more, of flanking genomic DNA at either the 5' or 3' end of the transcribed region. The genomic DNA may be isolated as a fragment of 100 kbp or smaller; and substantially free of flanking chromosomal sequence. The genomic DNA flanking the coding region, either 3' or 5', or internal regulatory sequences as sometimes found in introns, contains sequences required for proper tissue and stage specific expression.

The nucleic acid compositions of the subject invention may encode all or a part of the subject HEC-GLCNAC6ST protein. Double or single stranded fragments may be obtained from the DNA sequence by chemically synthesizing oligonucleotides in accordance with conventional methods, by restriction enzyme digestion, by PCR amplification, etc. For the most part, DNA fragments will be of at least 15 nt, usually at least 18 nt or 25 nt, and may be at least about 50 nt.

The HEC-GLCNAC6ST genes are isolated and obtained in substantial purity, generally as other than an intact chromosome. Usually, the DNA will be obtained substantially free of other nucleic acid sequences that do not include a HEC-GLCNAC6ST sequence or fragment thereof, generally being at least about 50%, usually at least about 90% pure and are typically "recombinant", i.e. flanked by one or more nucleotides with which it is not normally associated on a naturally occurring chromosome.

Preparation of HEC-GLCNAC6ST Polypeptides

In addition to the plurality of uses described in greater detail in following sections, the subject nucleic acid compositions find use in the preparation of all or a portion of the HEC-GLCNAC6ST polypeptides, as described above. For expression, an expression cassette may be employed. The expression vector will provide a transcriptional and translational initiation region, which may be inducible or constitutive, where the coding region is operably linked under the transcriptional control of the transcriptional initiation region, and a transcriptional and translational termination region. These control regions may be native to a HEC-GLCNAC6ST gene, or may be derived from exogenous sources.

Expression vectors generally have convenient restriction sites located near the promoter sequence to provide for the insertion of nucleic acid sequences encoding heterologous proteins. A selectable marker operative in the expression host may be present. Expression vectors may be used for the production of fusion proteins, where the exogenous fusion peptide provides additional functionality, i.e. increased protein synthesis, stability, reactivity with defined antisera, an enzyme marker, e.g. β-galactosidase, etc.

Expression cassettes may be prepared comprising a transcription initiation region, the gene or fragment thereof, and a transcriptional termination region. Of particular interest is the use of sequences that allow for the expression of functional epitopes or domains, usually at least about 8 amino acids in length, more usually at least about 15 amino acids in length, to about 25 amino acids, and up to the complete open reading frame of the gene. After introduction of the DNA, the cells containing the construct may be selected by means of a selectable marker, the cells expanded and then used for expression.

HEC-GLCNAC6ST proteins and polypeptides may be expressed in prokaryotes or eukaryotes in accordance with conventional ways, depending upon the purpose for expression. For large scale production of the protein, a unicellular organism, such as E. coli, B. subtilis, S. cerevisiae, insect cells in combination with baculovirus vectors, or cells of a higher organism such as vertebrates, particularly mammals, e.g. COS 7 cells, may be used as the expression host cells. In some situations, it is desirable to express the HEC-GLCNAC6ST gene in eukaryotic cells, where the HEC-GLCNAC6ST protein will benefit from native folding and post-translational modifications. Small peptides can also be synthesized in the laboratory. Polypeptides that are subsets of the complete HEC-GLCNAC6ST sequence may be used to identify and investigate parts of the protein important for function.

Specific expression systems of interest include bacterial, yeast, insect cell and mammalian cell derived expression systems. Representative systems from each of these categories is are provided below:

Bacteria. Expression systems in bacteria include those described in Chang et al., *Nature* (1978) 275:615; Goeddel et al., *Nature* (1979) 281:544; Goeddel et al., *Nucleic Acids Res.* (1980) 8:4057; EP 0 036,776; U.S. Pat. No. 4,551,433; DeBoer et al., *Proc. Natl. Acad. Sci.* (*USA*) (1983) 80:21–25; and Siebenlist et al., *Cell* (1980) 20:269.

Yeast. Expression systems in yeast include those described in Hinnen et al., *Proc. Natl. Acad. Sci.* (*USA*) (1978) 75:1929; Ito et al., *J. Bacteriol.* (1983) 153:163; Kurtz et al., *Mol. Cell. Biol.* (1986) 6:142; Kunze et al., *J. Basic Microbiol.* (1985) 25:141; Gleeson et al., *J. Gen. Microbiol.* (1986) 132:3459; Roggenkamp et al., *Mol. Gen. Genet.* (1986) 202:302; Das et al., *J. Bacteriol.* (1984) 158:1165; De Louvencourt et al., *J. Bacteriol.* (1983) 154:737; Van den Berg et al., *Bio/Technology* (1990) 8:135; Kunze et al., *J. Basic Microbiol.* (1985) 25:141; Cregg et al., *Mol. Cell. Biol.* (1985) 5:3376; U.S. Pat. Nos. 4,837,140 and 4,929,555; Beach and Nurse, *Nature* (1981) 300:706; Davidow et al., *Curr. Genet.* (1985) 10:380; Gaillardin et al., *Curr. Genet.* (1985) 10:49; Ballance et al., *Biochem. Biophys. Res. Commun.* (1983) 112:284–289; Tilburn et al., *Gene* (1983) 26:205–221; Yelton et al., *Proc. Natl. Acad. Sci.* (*USA*) (1984) 81:1470–1474; Kelly and Hynes, *EMBO J.* (1985) 4:475479; EP 0 244,234; and WO 91/00357.

Insect Cells. Expression of heterologous genes in insects is accomplished as described in U.S. Pat. No. 4,745,051; Friesen et al., "The Regulation of Baculovirus Gene Expression", in: *The Molecular Biology Of Baculoviruses* (1986) (W. Doerfler, ed.); EP 0 127,839; EP 0 155,476; and Vlak et al., *J. Gen. Virol.* (1988) 69:765–776; Miller et al., *Ann. Rev. Microbiol.* (1988) 42:177; Carbonell et al., *Gene* (1988) 73:409; Maeda et al., *Nature* (1985) 315:592–594; Lebacq-Verheyden et al., *Mol. Cell. Biol.* (1988) 8:3129; Smith et al., *Proc. Natl. Acad. Sci.* (*USA*) (1985) 82:8844; Miyajima et al., *Gene* (1987) 58:273; and Martin et al., *DNA* (1988) 7:99. Numerous baculoviral strains and variants and corresponding permissive insect host cells from hosts are described in Luckow et al., *Bio/Technology* (1988) 6:47–55, Miller et al., *Generic Engineering* (1986) 8:277–279, and Maeda et al., *Nature* (1985) 315:592–594.

Mammalian Cells. Mammalian expression is accomplished as described in Dijkema et al., *EMBO J.* (1985) 4:761, Gorman et al., *Proc. Natl. Acad. Sci.* (*USA*) (1982) 79:6777, Boshart et al., *Cell* (1985) 41:521 and U.S. Pat. No. 4,399,216. Other features of mammalian expression are facilitated as described in Ham and Wallace, *Meth. Enz.* (1979) 58:44, Barnes and Sato, *Anal. Biochem.* (1980) 102:255, U.S. Pat. Nos. 4,767,704, 4,657,866, 4,927,762, 4,560,655, WO 90/103430, WO 87/00195, and U.S. Pat. No. RE 30,985.

When any of the above host cells, or other appropriate host cells or organisms, are used to replicate and/or express the polynucleotides or nucleic acids of the invention, the resulting replicated nucleic acid, RNA, expressed protein or polypeptide, is within the scope of the invention as a product of the host cell or organism. The product is recovered by any appropriate means known in the art.

Once the gene corresponding to a selected polynucleotide is identified, its expression can be regulated in the cell to which the gene is native. For example, an endogenous gene of a cell can be regulated by an exogenous regulatory sequence inserted into the genome of the cell at location sufficient to at least enhance expressed of the gene in the cell. The regulatory sequence may be designed to integrate into the genome via homologous recombination, as disclosed in U.S. Pat. Nos. 5,641,670 and 5,733,761, the disclosures of which are herein incorporated by reference, or may be designed to integrate into the genome via non-homologous recombination, as described in WO 99/15650, the disclosure of which is herein incorporated by reference. As such, also encompassed in the subject invention is the production of the subject aggrecanase proteins without manipulation of the encoding nucleic acid itself, but instead through integration of a regulatory sequence into the genome of cell that already includes a gene encoding the desired protein, as described in the above incorporated patent documents.

Uses of the Subject HEC-GLCNAC6ST Polypeptide and Nucleic Acid Compositions

The subject polypeptide and nucleic acid compositions find use in a variety of different applications, including research, diagnostic, and therapeutic agent screening/discovery/preparation applications, as well as therapeutic compositions.

Representative Applications

The subject nucleic acid compositions find use in a variety of applications. Representative applications of interest include: the identification of HEC-GLCNAC6ST homologs; as a source of promoter elements; the identification of HEC-GLCNAC6ST expression regulatory factors; as probes and primers in hybridization applications, e.g. PCR; the identification of expression patterns in biological specimens; the preparation of cell or animal models for HEC-GLCNAC6ST function; the preparation of in vitro models for HEC-GLCNAC6ST function; etc.

Homologs of HEC-GLCNAC6ST are identified by any of a number of methods. A fragment of the provided cDNA may be used as a hybridization probe against a cDNA library from the target organism of interest, where low stringency conditions are used. The probe may be a large fragment, or one or more short degenerate primers. Nucleic acids having sequence similarity are detected by hybridization under low stringency conditions, for example, at 50° C. and 6×SSC (0.9 M sodium chloride/0.09 M sodium citrate) and remain bound when subjected to washing at 55° C. in 1×SSC (0.15 M sodium chloride/0.015 M sodium citrate). Sequence identity may be determined by hybridization under stringent conditions, for example, at 50° C. or higher and 0.1×SSC (15 mM sodium chloride/01.5 mM sodium citrate). Nucleic acids having a region of substantial identity to the provided HEC-GLCNAC6ST sequences, e.g. allelic variants, genetically altered versions of the gene, etc., bind to the provided HEC-GLCNAC6ST sequences under stringent hybridization conditions. By using probes, particularly labeled probes of DNA sequences, one can isolate homologous or related genes.

The sequence of the 5' flanking region may be utilized for promoter elements, including enhancer binding sites, that provide for developmental regulation in tissues where HEC-GLCNAC6ST is expressed. The tissue specific expression is useful for determining the pattern of expression, and for providing promoters that mimic the native pattern of expression. Naturally occurring polymorphisms in the promoter region are useful for determining natural variations in expression, particularly those that may be associated with disease.

Alternatively, mutations may be introduced into the promoter region to determine the effect of altering expression in experimentally defined systems. Methods for the identification of specific DNA motifs involved in the binding of transcriptional factors are known in the art, e.g. sequence similarity to known binding motifs, gel retardation studies, etc. For examples, see Blackwell et al. (1995), *Mol. Med.* 1:194–205; Mortlock et al. (1996), *Genome Res.* 6:327–33; and Joulin and Richard-Foy (1995), *Eur. J. Biochem.* 232:620–626.

The regulatory sequences may be used to identify cis acting sequences required for transcriptional or translational regulation of HEC-GLCNAC6ST expression, especially in different tissues or stages of development, and to identify cis acting sequences and trans-acting factors that regulate or mediate HEC-GLCNAC6ST expression. Such transcription or translational control regions may be operably linked to a HEC-GLCNAC6ST gene in order to promote expression of wild type or altered HEC-GLCNAC6ST or other proteins of interest in cultured cells, or in embryonic, fetal or adult tissues, and for gene therapy.

Small DNA fragments are useful as primers for PCR, hybridization screening probes, etc. Larger DNA fragments, i.e. greater than 100 nt are useful for production of the encoded polypeptide, as described in the previous section. For use in amplification reactions, such as PCR, a pair of primers will be used. The exact composition of the primer sequences is not critical to the invention, but for most applications the primers will hybridize to the subject sequence under stringent conditions, as known in the art. It is preferable to choose a pair of primers that will generate an amplification product of at least about 50 nt, preferably at least about 100 nt. Algorithms for the selection of primer sequences are generally known, and are available in commercial software packages. Amplification primers hybridize to complementary strands of DNA, and will prime towards each other.

The DNA may also be used to identify expression of the gene in a biological specimen. The manner in which one probes cells for the presence of particular nucleotide sequences, as genomic DNA or RNA, is well established in the literature. Briefly, DNA or mRNA is isolated from a cell sample. The mRNA may be amplified by RT-PCR, using reverse transcriptase to form a complementary DNA strand, followed by polymerase chain reaction amplification using primers specific for the subject DNA sequences. Alternatively, the mRNA sample is separated by gel electrophoresis, transferred to a suitable support, e.g. nitrocellulose, nylon, etc., and then probed with a fragment of the subject DNA as a probe. Other techniques, such as oligonucleotide ligation assays, in situ hybridizations, and hybridization to DNA probes arrayed on a solid chip may also find use. Detection of mRNA hybridizing to the subject sequence is indicative of HEC-GLCNAC6ST gene expression in the sample.

The sequence of a HEC-GLCNAC6ST gene, including flanking promoter regions and coding regions, may be mutated in various ways known in the art to generate targeted changes in promoter strength, sequence of the encoded protein, etc. The DNA sequence or protein product of such a mutation will usually be substantially similar to the sequences provided herein, i.e. will differ by at least one nucleotide or amino acid, respectively, and may differ by at least two but not more than about ten nucleotides or amino acids. The sequence changes may be substitutions, insertions, deletions, or a combination thereof. Deletions may further include larger changes, such as deletions of a domain or exon. Other modifications of interest include epitope tagging, e.g. with the FLAG system, HA, etc. For studies of subcellular localization, fusion proteins with green fluorescent proteins (GFP) may be used.

Techniques for in vitro mutagenesis of cloned genes are known. Examples of protocols for site specific mutagenesis may be found in Gustin et al. (1993), *Biotechniques* 14:22; Barany (1985), *Gene* 37:111–23; Colicelli et al. (1985), *Mol. Gen. Genet.* 199:537–9; and Prentki et al. (1984), *Gene* 29:303–13. Methods for site specific mutagenesis can be found in Sambrook et al., *Molecular Cloning: A Laboratory Manual*, CSH Press 1989, pp. 15.3–15.108; Weiner et al. (1993), *Gene* 126:35–41; Sayers et al. (1992), *Biotechniques* 13:592–6; Jones and Winistorfer (1992), *Biotechniques* 12:528–30; Barton et al. (1990), *Nucleic Acids Res* 18:7349–55; Marotti and Tomich (1989), *Gene Anal. Tech.* 6:67–70; and Zhu (1989), *Anal Biochem* 177:120–4. Such mutated genes may be used to study structure-function relationships of HEC-GLCNAC6ST, or to alter properties of the protein that affect its function or regulation.

The subject nucleic acids can be used to generate transgenic, non-human animals or site specific gene modifications in cell lines. Transgenic animals may be made through homologous recombination, where the normal HEC-GlcNAc6ST locus is altered. Alternatively, a nucleic acid construct is randomly integrated into the genome. Vectors for stable integration include plasmids, retroviruses and other animal viruses, YACs, and the like.

The modified cells or animals are useful in the study of HEC-GlcNAc6ST function and regulation. For example, a series of small deletions and/or substitutions may be made in the host's native HEC-GlcNAc6ST gene to determine the role of different exons in conditions associated with HEC-GLCNAC6ST activity, e.g. inflammation, etc. Specific constructs of interest include anti-sense HEC-GlcNAc6ST, which will block HEC-GLCNAC6ST expression, expression of dominant negative HEC-GlcNAc6ST mutations, and over-expression of HEC-GLCNAC6ST genes. Where a HEC-GlcNAc6ST sequence is introduced, the introduced sequence may be either a complete or partial sequence of a HEC-GlcNAc6ST gene native to the host, or may be a complete or partial HEC-GlcNAc6ST sequence that is exogenous to the host animal, e.g., a human HEC-GLCNAC6ST sequence. A detectable marker, such as lac Z may be introduced into the HEC-GlcNAc6ST locus, where upregulation of HEC-GlcNAc6ST expression will result in an easily detected change in phenotype.

One may also provide for expression of the HEC-GlcNAc6ST gene or variants thereof in cells or tissues where it is not normally expressed, at levels not normally present in such cells or tissues, or at abnormal times of development.

DNA constructs for homologous recombination will comprise at least a portion of the human HEC-GLCNAC6ST gene or of a HEC-GlcNAc6ST gene native to the species of the host animal, wherein the gene has the desired genetic modification(s), and includes regions of homology to the target locus. DNA constructs for random integration need not include regions of homology to mediate recombination. Conveniently, markers for positive and negative selection are included. Methods for generating cells having targeted gene modifications through homologous recombination are known in the art. For various techniques for transfecting mammalian cells, see Keown et al. (1990), *Meth. Enzymol.* 185:527–537.

For embryonic stem (ES) cells, an ES cell line may be employed, or embryonic cells may be obtained freshly from a host, e.g. mouse, rat, guinea pig, etc. Such cells are grown on an appropriate fibroblast-feeder layer or grown in the presence of leukemia inhibiting factor (LIF). When ES or embryonic cells have been transformed, they may be used to produce transgenic animals. After transformation, the cells are plated onto a feeder layer in an appropriate medium. Cells containing the construct may be detected by employing a selective medium. After sufficient time for colonies to grow, they are picked and analyzed for the occurrence of homologous recombination or integration of the construct. Those colonies that are positive may then be used for embryo manipulation and blastocyst injection. Blastocysts are obtained from 4 to 6 week old superovulated females. The ES cells are trypsinized, and the modified cells are injected into the blastocoel of the blastocyst. After injection, the blastocysts are returned to each uterine horn of pseudopregnant females. Females are then allowed to go to term and the resulting offspring screened for the construct. By providing for a different phenotype of the blastocyst and the genetically modified cells, chimeric progeny can be readily detected.

The chimeric animals are screened for the presence of the modified gene and males and females having the modification are mated to produce homozygous progeny. If the gene alterations cause lethality at some point in development, tissues or organs can be maintained as allogeneic or congenic grafts or transplants, or in in vitro culture. The transgenic animals may be any non-human mammal, such as laboratory animals, domestic animals, etc. The transgenic animals may be used in functional studies, drug screening, etc., e.g. to determine the effect of a candidate drug on HEC-GLCNAC6ST activity.

The availability of a number of components in the leukocyte trafficking mechanism, such as GlyCAM-1, L-selectin and the subject HEC-GLCNAC6ST enzyme, and the like, allows in vitro reconstruction of the mechanism, i.e. the production of an in vitro model.

Diagnostic Applications

Also provided are methods of diagnosing disease states based on observed levels of HEC-GLCNAC6ST or the expression level of the HEC-GLCNAC6ST gene in a biological sample of interest. Samples, as used herein, include biological fluids such as blood, cerebrospinal fluid, tears, saliva, lymph, dialysis fluid, and the like; organ or tissue culture derived fluids; and fluids extracted from physiological tissues. Also included in the term are derivatives and fractions of such fluids. The cells may be dissociated, in the case of solid tissues, or tissue sections may be analyzed. Alternatively a lysate of the cells may be prepared.

A number of methods are available for determining the expression level of a gene or protein in a particular sample. Diagnosis may be performed by a number of methods to determine the absence or presence or altered amounts of normal or abnormal HEC-GLCNAC6ST in a patient sample. For example, detection may utilize staining of cells or histological sections with labeled antibodies, performed in accordance with conventional methods. Cells are permeabilized to stain cytoplasmic molecules. The antibodies of interest are added to the cell sample, and incubated for a period of time sufficient to allow binding to the epitope, usually at least about 10 minutes. The antibody may be labeled with radioisotopes, enzymes, fluorescers, chemiluminescers, or other labels for direct detection. Alternatively, a second stage antibody or reagent is used to amplify the signal. Such reagents are well known in the art. For example, the primary antibody may be conjugated to biotin, with horseradish peroxidase-conjugated avidin added as a second stage reagent. Alternatively, the secondary antibody conjugated to a flourescent compound, e.g. fluorescein, rhodamine, Texas red, etc. Final detection uses a substrate that undergoes a color change in the presence of the peroxidase. The absence or presence of antibody binding may be determined by various methods, including flow cytometry of dissociated cells, microscopy, radiography, scintillation counting, etc.

Alternatively, one may focus on the expression of HEC-GLCNAC6ST. Biochemical studies may be performed to determine whether a sequence polymorphism in a HEC-GLCNAC6ST coding region or control regions is associated with disease. Disease associated polymorphisms may include deletion or truncation of the gene, mutations that alter expression level, that affect the activity of the protein, etc.

Changes in the promoter or enhancer sequence that may affect expression levels of HEC-GLCNAC6ST can be compared to expression levels of the normal allele by various methods known in the art. Methods for determining promoter or enhancer strength include quantitation of the expressed natural protein; insertion of the variant control element into a vector with a reporter gene such as β-galactosidase, luciferase, chloramphenicol acetyltransferase, etc. that provides for convenient quantitation; and the like.

A number of methods are available for analyzing nucleic acids for the presence of a specific sequence, e.g. a disease associated polymorphism. Where large amounts of DNA are available, genomic DNA is used directly. Alternatively, the region of interest is cloned into a suitable vector and grown in sufficient quantity for analysis. Cells that express HEC-GLCNAC6ST may be used as a source of mRNA, which may be assayed directly or reverse transcribed into cDNA for analysis. The nucleic acid may be amplified by conventional techniques, such as the polymerase chain reaction (PCR), to provide sufficient amounts for analysis. The use of the polymerase chain reaction is described in Saiki, et al (1985), *Science* 239:487, and a review of techniques may be found in Sambrook, et al. *Molecular Cloning: A Laboratory Manual*, CSH Press 1989, pp.14.2–14.33. Alternatively, various methods are known in the art that utilize oligonucleotide ligation as a means of detecting polymorphisms, for examples see Riley et al. (1990), *Nucl. Acids Res.* 18:2881–2890; and Delahunty et al. (1996), *Am. J. Hum. Genet.* 58:1239–1246.

A detectable label may be included in an amplification reaction. Suitable labels include fluorochromes, e.g. fluorescein isothiocyanate (FITC), rhodamine, Texas Red, phycoerythrin, allophycocyanin, 6-carboxyfluorescein (6-FAM), 2',7'-dimethoxy-4',5'-dichloro-6-carboxyfluorescein (JOE), 6-carboxy-X-rhodamine (ROX), 6-carboxy-2',4',7',4,7-hexachlorofluorescein (HEX), 5-carboxyfluorescein (5-FAM) or N,N,N',N'-tetramethyl-6-carboxyfluodamine (TAMRA), radioactive labels, e.g. $^{32}P$, $^{35}S$, $^{3}H$; etc. The label may be a two stage system, where the amplified DNA is conjugated to biotin, haptens, etc. having a high affinity binding partner, e.g. avidin, specific antibodies, etc., where the binding partner is conjugated to a detectable label. The label may be conjugated to one or both of the primers. Alternatively, the pool of nucleotides used in the amplification is labeled, so as to incorporate the label into the amplification product.

The sample nucleic acid, e.g. amplified or cloned fragment, is analyzed by one of a number of methods known in the art. The nucleic acid may be sequenced by dideoxy or other methods, and the sequence of bases compared to a wild-type HEC-GLCNAC6ST sequence. Hybridization with the variant sequence may also be used to determine its presence, by Southern blots, dot blots, etc. The hybridization pattern of a control and variant sequence to an array of oligonucleotide probes immobilized on a solid support, as described in U.S. Pat. No. 5,445,934, or in WO 95/35505, may also be used as a means of detecting the presence of variant sequences. Single strand conformational polymorphism (SSCP) analysis, denaturing gradient gel electrophoresis (DGGE), and heteroduplex analysis in gel matrices are used to detect conformational changes created by DNA sequence variation as alterations in electrophoretic mobility. Alternatively, where a polymorphism creates or destroys a recognition site for a restriction endonuclease, the sample is digested with that endonuclease, and the products size fractionated to determine whether the fragment was digested. Fractionation is performed by gel or capillary electrophoresis, particularly acrylamide or agarose gels.

Screening for mutations in HEC-GLCNAC6ST may be based on the functional or antigenic characteristics of the protein. Protein truncation assays are useful in detecting deletions that may affect the biological activity of the protein. Various immunoassays designed to detect polymorphisms in HEC-GLCNAC6ST proteins may be used in screening. Where many diverse genetic mutations lead to a particular disease phenotype, functional protein assays have proven to be effective screening tools. The activity of the encoded HEC-GLCNAC6ST protein may be determined by comparison with the wild-type protein.

Diagnostic methods of the subject invention in which the level of HEC-GLCNAC6ST expression is of interest will typically involve comparison of the HEC-GLCNAC6ST nucleic acid abundance of a sample of interest with that of a control value to determine any relative differences, where the difference may be measured qualitatively and/or quantitatively, which differences are then related to the presence or absence of an abnormal HEC-GLCNAC6ST expression pattern. A variety of different methods for determine the nucleic acid abundance in a sample are known to those of skill in the art, where particular methods of interest include those described in: Pietu et al., Genome Res. (June 1996) 6: 492–503; Zhao et al., Gene (Apr. 24, 1995) 156: 207–213; Soares, Curr. Opin. Biotechnol. (October 1997) 8: 542–546; Raval, J. Pharmacol Toxicol Methods (November 1994) 32: 125–127; Chalifour et al., Anal. Biochem (Feb. 1, 1994) 216: 299–304; Stolz & Tuan, Mol. Biotechnol. (December 19960 6: 225–230; Hong et al., Bioscience Reports (1982) 2: 907; and McGraw, Anal. Biochem. (1984) 143: 298. Also of interest are the methods disclosed in WO 97/27317, the disclosure of which is herein incorporated by reference.

Screening Assays

The subject HEC-GLCNAC6ST polypeptides (as well as the HEC-specific KSGal6ST homologues) find use in various screening assays designed to identify therapeutic agents. Thus, one can use a cell model such as a host cell, e.g. COS7 cell, which has been cotransfected with a selectin ligand cDNA, e.g. GlyCAM-1 or CD34 and a HEC-GLCNAC6ST vector. One can then label the transfectants with a labeled sulfate, e.g. $^{35}S$-labeled sulfate, and compare the amount of sulfate incorporation into GlyCAM-1 or CD34 in the presence and absence of a candidate inhibitor compound. Alternatively, in a cell-free enzyme activity assay, recombinant HEC-GLCNAC6ST polypeptide may be combined with $^{35}S$-labeled sulfate donor such as [$^{35}S$]-PAPS, candidate inhibitor compound, and an acceptor molecule, which may be a synthetic carbohydrate mimicking structures found in mature and/or immature L-selectin ligands, or a simple nucleophile capable of accepting sulfate (such as phenolic compunds, and the like). The amount of [$^{35}S$]-sulfate transferred to the receptor by the candidate agent is then determined by counting the acceptor-associated radioactivity or product quantitation with an antibody specific for the sulfated acceptor, or in a suitable scintillation proximity assay format. Alternatively, the candidate inhibitor compound may also be combined with a selectin, a non-sulfated selectin ligand precursor, HEC-GLCNAC6ST and a sulfate donor compound under physiological conditions and the resultant amount of ligand which is capable of binding to the selectin is determined. Depending on the particular method, one or more of, usually one of, the specified components may be labeled, where by labeled is meant that the components comprise a detectable moiety, e.g. a fluorescent or radioactive tag, or a member of a signal producing system, e.g. biotin for binding to an enzyme-streptavidin conjugate in which the enzyme is capable of converting a substrate to a chromogenic product.

A variety of other reagents may be included in the screening assay. These include reagents like salts, neutral proteins, e.g. albumin, detergents, etc that are used to facilitate optimal protein-protein binding and/or reduce non-specific or background interactions. Reagents that improve the efficiency of the assay, such as protease inhibitors, nuclease inhibitors, anti-microbial agents, etc. may be used.

The above screening methods may be designed a number of different ways, where a variety of assay configurations and protocols may be employed, as are known in the art. For example, one of the components may be bound to a solid support, and the remaining components contacted with the support bound component. The above components of the method may be combined at substantially the same time or at different times. Incubations are performed at any suitable temperature, typically between 4 and 40° C. Incubation periods are selected for optimum activity, but may also be optimized to facilitate rapid high-throughput screening. Typically between 0.1 and 1 hours will be sufficient: Following the contact and incubation steps, the subject methods will generally, though not necessarily, further include a washing step to remove unbound components, where such a washing step is generally employed when required to remove label that would give rise to a background signal during detection, such as radioactive or fluorescently labeled non-specifically bound components. Following the optional washing step, the presence of bound selectin-ligand complexes will then be detected.

A variety of different candidate agents may be screened by the above methods. Candidate agents encompass numerous chemical classes, though typically they are organic molecules, preferably small organic compounds having a molecular weight of more than 50 and less than about 2,500 daltons. Candidate agents comprise functional groups necessary for structural interaction with proteins, particularly hydrogen bonding, and typically include at least an amine, carbonyl, hydroxyl or carboxyl group, preferably at least two of the functional chemical groups. The candidate agents often comprise cyclical carbon or heterocyclic structures and/or aromatic or polyaromatic structures substituted with one or more of the above functional groups. Candidate agents are also found among biomolecules including peptides, saccharides, fatty acids, steroids, purines, pyrimidines, derivatives, structural analogs or combinations thereof.

Candidate agents are obtained from a wide variety of sources including libraries of synthetic or natural compounds. For example, numerous means are available for random and directed synthesis of a wide variety of organic compounds and biomolecules, including expression of randomized oligonucleotides and oligopeptides. Alternatively, libraries of natural compounds in the form of bacterial, fungal, plant and animal extracts are available or readily produced. Additionally, natural or synthetically produced libraries and compounds are readily modified through conventional chemical, physical and biochemical means, and may be used to produce combinatorial libraries. Known pharmacological agents may be subjected to directed or random chemical modifications, such as acylation, alkylation, esterification, amidification, etc. to produce structural analogs.

HEC-GLCNAC6ST Nucleic Acid and Polypeptide Therapeutic Compositions

The nucleic acid compositions of the subject invention also find use as therapeutic agents in situations where one wishes to enhance HEC-GLCNAC6ST activity in a host. The HEC-GLCNAC6ST genes, gene fragments, or the encoded HEC-GLCNAC6ST protein or protein fragments are useful in gene therapy to treat disorders associated with HEC-GLCNAC6ST defects. Expression vectors may be used to introduce the HEC-GLCNAC6ST gene into a cell. Such vectors generally have convenient restriction sites located near the promoter sequence to provide for the insertion of nucleic acid sequences. Transcription cassettes may be prepared comprising a transcription initiation region, the target gene or fragment thereof, and a transcriptional termination region. The transcription cassettes may be introduced into a variety of vectors, e.g. plasmid; retrovirus, e.g. lentivirus; adenovirus; and the like, where the vectors are able to transiently or stably be maintained in the cells, usually for a period of at least about one day, more usually for a period of at least about several days to several weeks.

The gene or HEC-GLCNAC6ST protein may be introduced into tissues or host cells by any number of routes, including viral infection, microinjection, or fusion of vesicles. Jet injection may also be used for intramuscular administration, as described by Furth et al. (1992), *Anal Biochem* 205:365–368. The DNA may be coated onto gold microparticles, and delivered intradermally by a particle bombardment device, or "gene gun" as described in the literature (see, for example, Tang et al. (1992), *Nature* 356:152–154), where gold microprojectiles are coated with the DNA, then bombarded into skin cells.

Methods of Modulating Selectin Mediated Binding Events

Also provided are methods of regulating, including modulating and inhibiting, selectin mediated binding events. The selectin receptor of the selectin mediated binding event will generally be a receptor which binds to a sulfated ligand under physiological conditions and is a member of the selectin family of receptors that have an amino terminal C-type lectin domain followed by an EFG-like domain, a variable number of short consensus repeats known as SCR, CRP or sushi domains, and share greater than 50% homology in their lectin and EFG domains. Of interest is the modulation of selectin binding events in which the selectin is L-, P-, or E-selectin. Of particular interest are L-selectin mediated binding events.

Where the selectin mediated binding event occurs in vivo in a host, in one embodiment an effective amount of active agent that modulates the activity, usually reduces the activity, of HEC-GLCNAC6ST in vivo, is administered to the host. In another embodiment, the modulating agent is targeted to KSGal6ST, or an HEC-specific homologue thereof. In yet another embodiment, one or more agents are administered that effectively modulate both the KSGal6ST or related activity and the HEC-GLCNAC6ST activity. The active agent may be a variety of different compounds, including a naturally occurring or synthetic small molecule compound, an antibody, fragment or derivative thereof, an antisense composition, and the like.

Naturally occurring or synthetic small molecule compounds of interest include numerous chemical classes, though typically they are organic molecules, preferably small organic compounds having a molecular weight of more than 50 and less than about 2,500 daltons. Candidate agents comprise functional groups necessary for structural interaction with proteins, particularly hydrogen bonding, and typically include at least an amine, carbonyl, hydroxyl or carboxyl group, preferably at least two of the functional chemical groups. The candidate agents often comprise cyclical carbon or heterocyclic structures and/or aromatic or polyaromatic structures substituted with one or more of the above functional groups. Candidate agents are also found among biomolecules including peptides, saccharides, fatty acids, steroids, purines, pyrimidines, derivatives, structural analogs or combinations thereof.

Also of interest as active agent are antibodies that at least reduce, if not inhibit, the target activity in the host (e.g. the HEC-GLCNAC6ST activity and/or the KSGal6ST activity). Suitable antibodies are obtained by immunizing a host animal with peptides comprising all or a portion of the target protein. Suitable host animals include mouse, rat sheep, goat, hamster, rabbit, etc. The origin of the protein immunogen may be mouse, human, rat, monkey etc. The host animal will generally be a different species than the immunogen, e.g. human HEC-GLCNAC6ST used to immunize mice, etc.

The immunogen may comprise the complete protein, or fragments and derivatives thereof. Preferred immunogens comprise all or a part of HEC-GLCNAC6ST, where these residues contain the post-translation modifications, such as glycosylation, found on the native target protein. Immunogens comprising the extracellular domain are produced in a variety of ways known in the art, e.g. expression of cloned genes using conventional recombinant methods, isolation from HEC, etc.

For preparation of polyclonal antibodies, the first step is immunization of the host animal with the target protein, where the target protein will preferably be in substantially pure form, comprising less than about 1% contaminant. The immunogen may comprise the complete target protein, fragments or derivatives thereof. To increase the immune response of the host animal, the target protein may be combined with an adjuvant, where suitable adjuvants include alum, dextran, sulfate, large polymeric anions, oil& water emulsions, e.g. Freund's adjuvant, Freund's complete adjuvant, and the like. The target protein may also be conjugated to synthetic carrier proteins or synthetic antigens. A variety of hosts may be immunized to produce the polyclonal antibodies. Such hosts include rabbits, guinea pigs, rodents, e.g. mice, rats, sheep, goats, and the like. The target protein is administered to the host, usually intradermally, with an initial dosage followed by one or more, usually at least two, additional booster dosages. Following immunization, the blood from the host will be collected, followed by separation of the serum from the blood cells. The Ig present in the resultant antiserum may be further fractionated using known methods, such as ammonium salt fractionation, DEAE chromatography, and the like.

Monoclonal antibodies are produced by conventional techniques. Generally, the spleen and/or lymph nodes of an immunized host animal provide a source of plasma cells. The plasma cells are immortalized by fusion with myeloma cells to produce hybridoma cells. Culture supernatant from individual hybridomas is screened using standard techniques to identify those producing antibodies with the desired specificity. Suitable animals for production of monoclonal antibodies to the human protein include mouse, rat, hamster, etc. To raise antibodies against the mouse protein, the animal will generally be a hamster, guinea pig, rabbit, etc. The antibody may be purified from the hybridoma cell supernatants or ascites fluid by conventional techniques, e.g. affinity chromatography using HEC-GLCNAC6ST bound to an insoluble support, protein A sepharose, etc.

The antibody may be produced as a single chain, instead of the normal multimeric structure. Single chain antibodies are described in Jost et al. (1994) *J.B.C.* 269:26267–73, and others. DNA sequences encoding the variable region of the heavy chain and the variable region of the light chain are ligated to a spacer encoding at least about 4 amino acids of small neutral amino acids, including glycine and/or serine. The protein encoded by this fusion allows assembly of a functional variable region that retains the specificity and affinity of the original antibody.

For in vivo use, particularly for injection into humans, it is desirable to decrease the antigenicity of the antibody. An immune response of a recipient against the blocking agent will potentially decrease the period of time that the therapy is effective. Methods of humanizing antibodies are known in the art. The humanized antibody may be the product of an animal having transgenic human immunoglobulin constant region genes (see for example International Patent Applications WO 90/10077 and WO 90/04036). Alternatively, the antibody of interest may be engineered by recombinant DNA techniques to substitute the CH1, CH2, CH3, hinge domains, and/or the framework domain with the corresponding human sequence (see WO 92/02190).

The use of Ig cDNA for construction of chimeric immunoglobulin genes is known in the art (Liu et al. (1987) *P.N.A.S.* 84:3439 and (1987) *J. Immunol.* 139:3521). mRNA is isolated from a hybridoma or other cell producing the antibody and used to produce cDNA. The cDNA of interest may be amplified by the polymerase chain reaction using specific primers (U.S. Pat. Nos. 4,683,195 and 4,683,202). Alternatively, a library is made and screened to isolate the sequence of interest. The DNA sequence encoding the variable region of the antibody is then fused to human constant region sequences. The sequences of human constant regions genes may be found in Kabat et al. (1991) *Sequences of Proteins of Immunological Interest*, N.I.H. publication no. 91-3242. Human C region genes are readily available from known clones. The choice of isotype will be guided by the desired effector functions, such as complement fixation, or activity in antibody-dependent cellular cytotoxicity. Preferred isotypes are IgG1, IgG3 and IgG4. Either of the human light chain constant regions, kappa or lambda, may be used. The chimeric, humanized antibody is then expressed by conventional methods.

Antibody fragments, such as Fv, F(ab')$_2$ and Fab may be prepared by cleavage of the intact protein, e.g. by protease or chemical cleavage. Alternatively, a truncated gene is designed. For example, a chimeric gene encoding a portion of the F(ab')$_2$ fragment would include DNA sequences encoding the CH1 domain and hinge region of the H chain, followed by a translational stop codon to yield the truncated molecule.

Consensus sequences of H and L J regions may be used to design oligonucleotides for use as primers to introduce useful restriction sites into the J region for subsequent linkage of V region segments to human C region segments. C region cDNA can be modified by site directed mutagenesis to place a restriction site at the analogous position in the human sequence.

Expression vectors include plasmids, retroviruses, YACs, EBV derived episomes, and the like. A convenient vector is one that encodes a functionally complete human CH or CL immunoglobulin sequence, with appropriate restriction sites engineered so that any VH or VL sequence can be easily inserted and expressed. In such vectors, splicing usually occurs between the splice donor site in the inserted J region and the splice acceptor site preceding the human C region, and also at the splice regions that occur within the human CH exons. Polyadenylation and transcription termination occur at native chromosomal sites downstream of the coding regions. The resulting chimeric antibody may be joined to any strong promoter, including retroviral LTRs, e.g. SV-40 early promoter, (Okayama et al. (1983) *Mol. Cell. Bio.* 3:280), Rous sarcoma virus LTR (Gorman et al. (1982) *P.N.A.S.* 79:6777), and moloney murine leukemia virus LTR (Grosschedl et al. (1985) *Cell* 41:885); native Ig promoters, etc.

In yet other embodiments of the invention, the active agent is an agent that modulates, and generally decreases or down regulates, the expression of the gene encoding the target protein in the host. For example, antisense molecules can be used to down-regulate expression of HEC-GLCNAC6ST in cells. The anti-sense reagent may be antisense oligonucleotides (ODN), particularly synthetic ODN having chemical modifications from native nucleic acids, or nucleic acid constructs that express such anti-sense molecules as RNA. The antisense sequence is complementary to the mRNA of the targeted gene, and inhibits expression of the targeted gene products. Antisense molecules inhibit gene expression through various mechanisms, e.g. by reducing the amount of mRNA available for translation, through activation of RNAse H, or steric hindrance. One or a combination of antisense molecules may be administered, where a combination may comprise multiple different sequences.

Antisense molecules may be produced by expression of all or a part of the target gene sequence in an appropriate vector, where the transcriptional initiation is oriented such that an antisense strand is produced as an RNA molecule. Alternatively, the antisense molecule is a synthetic oligonucleotide. Antisense oligonucleotides will generally be at least about 7, usually at least about 12, more usually at least about 20 nucleotides in length, and not more than about 500, usually not more than about 50, more usually not more than about 35 nucleotides in length, where the length is governed by efficiency of inhibition, specificity, including absence of cross-reactivity, and the like. It has been found that short oligonucleotides, of from 7 to 8 bases in length, can be strong and selective inhibitors of gene expression (see Wagner et al. (1996), *Nature Biotechnol.* 14:840–844).

A specific region or regions of the endogenous sense strand mRNA sequence is chosen to be complemented by the antisense sequence. Selection of a specific sequence for the oligonucleotide may use an empirical method, where several candidate sequences are assayed for inhibition of expression of the target gene in an in vitro or animal model. A combination of sequences may also be used, where several regions of the mRNA sequence are selected for antisense complementation.

Antisense oligonucleotides may be chemically synthesized by methods known in the art (see Wagner et al. (1993), supra, and Milligan et al., supra.) Preferred oligonucleotides are chemically modified from the native phosphodiester structure, in order to increase their intracellular stability and binding affinity. A number of such modifications have been described in the literature, which alter the chemistry of the backbone, sugars or heterocyclic bases.

Among useful changes in the backbone chemistry are phosphorothioates; phosphorodithioates, where both of the non-bridging oxygens are substituted with sulfur; phosphoroamidites; alkyl phosphotriesters and boranophosphates. Achiral phosphate derivatives include 3'-O'-5'-S-phosphorothioate, 3'-S-5'-O-phosphorothioate, 3'-CH2-5'-O-phosphonate and 3'-NH-5'-O-phosphoroamidate. Peptide nucleic acids replace the entire ribose phosphodiester backbone with a peptide linkage. Sugar modifications are also used to enhance stability and affinity. The α-anomer of deoxyribose may be used, where the base is inverted with respect to the natural β-anomer. The 2'-OH of the ribose sugar may be altered to form 2'-O-methyl or 2'-O-allyl sugars, which provides resistance to degradation without comprising affinity. Modification of the heterocyclic bases must maintain proper base pairing. Some useful substitutions include deoxyuridine for deoxythymidine; 5-methyl-2'-deoxycytidine and 5-bromo-2'-deoxycytidine for deoxycytidine. 5-propynyl-2'-deoxyuridine and 5-propynyl-2'-deoxycytidine have been shown to increase affinity and biological activity when substituted for deoxythymidine and deoxycytidine, respectively.

As an alternative to anti-sense inhibitors, catalytic nucleic acid compounds, e.g. ribozymes, anti-sense conjugates, etc. may be used to inhibit gene expression. Ribozymes may be synthesized in vitro and administered to the patient, or may be encoded on an expression vector, from which the ribozyme is synthesized in the targeted cell (for example, see International patent application WO 9523225, and Beigelman et al. (1995), *Nucl. Acids Res.* 23:4434–42). Examples of oligonucleotides with catalytic activity are described in WO 9506764. Conjugates of anti-sense ODN with a metal complex, e.g. terpyridylCu(II), capable of mediating mRNA hydrolysis are described in Bashkin et al. (1995), *Appl. Biochem. Biotechnol.* 54:43–56.

As mentioned above, an effective amount of the active agent is administered to the host, where "effective amount" means a dosage sufficient to produce a desired result. Generally, the desired result is at least a reduction in the amount of selectin binding as compared to a control.

In the subject methods, the active agent(s) may be administered to the host using any convenient means capable of resulting in the desired inhibition of selectin binding. Thus, the agent can be incorporated into a variety of formulations for therapeutic administration. More particularly, the agents of the present invention can be formulated into pharmaceutical compositions by combination with appropriate, pharmaceutically acceptable carriers or diluents, and may be formulated into preparations in solid, semi-solid, liquid or gaseous forms, such as tablets, capsules, powders, granules, ointments, solutions, suppositories, injections, inhalants and aerosols.

As such, administration of the agents can be achieved in various ways, including oral, buccal, rectal, parenteral, intraperitoneal, intradermal, transdermal, intracheal, etc., administration.

In pharmaceutical dosage forms, the agents may be administered in the form of their pharmaceutically acceptable salts, or they may also be used alone or in appropriate association, as well as in combination, with other pharmaceutically active compounds. The following methods and excipients are merely exemplary and are in no way limiting.

For oral preparations, the agents can be used alone or in combination with appropriate additives to make tablets, powders, granules or capsules, for example, with conventional additives, such as lactose, mannitol, corn starch or potato starch; with binders, such as crystalline cellulose, cellulose derivatives, acacia, corn starch or gelatins; with disintegrators, such as corn starch, potato starch or sodium carboxymethylcellulose; with lubricants, such as talc or magnesium stearate; and if desired, with diluents, buffering agents, moistening agents, preservatives and flavoring agents.

The agents can be formulated into preparations for injection by dissolving, suspending or emulsifying them in an aqueous or nonaqueous solvent, such as vegetable or other similar oils, synthetic aliphatic acid glycerides, esters of higher aliphatic acids or propylene glycol; and if desired, with conventional additives such as solubilizers, isotonic agents, suspending agents, emulsifying agents, stabilizers and preservatives.

The agents can be utilized in aerosol formulation to be administered via inhalation. The compounds of the present invention can be formulated into pressurized acceptable propellants such as dichlorodifluoromethane, propane, nitrogen and the like.

Furthermore, the agents can be made into suppositories by mixing with a variety of bases such as emulsifying bases or water-soluble bases. The compounds of the present invention can be administered rectally via a suppository. The suppository can include vehicles such as cocoa butter, carbowaxes and polyethylene glycols, which melt at body temperature, yet are solidified at room temperature.

Unit dosage forms for oral or rectal administration such as syrups, elixirs, and suspensions may be provided wherein each dosage unit, for example, teaspoonful, tablespoonful, tablet or suppository, contains a predetermined amount of the composition containing one or more inhibitors. Similarly, unit dosage forms for injection or intravenous administration may comprise the inhibitor(s) in a composition as a solution in sterile water, normal saline or another pharmaceutically acceptable carrier.

The term "unit dosage form," as used herein, refers to physically discrete units suitable as unitary dosages for human and animal subjects, each unit containing a predetermined quantity of compounds of the present invention calculated in an amount sufficient to produce the desired effect in association with a pharmaceutically acceptable diluent, carrier or vehicle. The specifications for the unit dosage forms of the present invention depend on the particular compound employed and the effect to be achieved, and the pharmacodynamics associated with each compound in the host.

The pharmaceutically acceptable excipients, such as vehicles, adjuvants, carriers or diluents, are readily available to the public. Moreover, pharmaceutically acceptable auxiliary substances, such as pH adjusting and buffering agents, tonicity adjusting agents, stabilizers, wetting agents and the like, are readily available to the public.

Where the agent is a polypeptide, polynucleotide, analog or mimetic thereof, e.g. antisense composition, it may be introduced into tissues or host cells by any number of routes, including viral infection, microinjection, or fusion of vesicles. Jet injection may also be used for intramuscular administration, as described by Furth et al. (1992), Anal Biochem 205:365–368. The DNA may be coated onto gold microparticles, and delivered intradermally by a particle bombardment device, or "gene gun" as described in the literature (see, for example, Tang et al. (1992), Nature 356:152–154), where gold microprojectiles are coated with the therapeutic DNA, then bombarded into skin cells.

Those of skill in the art will readily appreciate that dose levels can vary as a function of the specific compound, the severity of the symptoms and the susceptibility of the subject to side effects. Preferred dosages for a given compound are readily determinable by those of skill in the art by a variety of means.

The subject methods find use in the treatment of a variety of different disease conditions involving selectin binding interactions, particularly L-, E- or P-selectin, and more particularly L-selectin mediated binding events. Such disease conditions include those disease conditions associated with or resulting from the homing of leukocytes to sites of inflammation, the normal homing of lymphocytes to secondary lymph organs; and the like. Accordingly, specific disease conditions that may be treated with the subject methods include: acute or chronic inflammation; autoimmune and related disorders, e.g. systemic lupus erythematosus, rheumatoid arthritis, polyarteritis nodosa, polymyositis and dermatomyositis, progressive systemic sclerosis (diffuse scleroderma), glomerulonephritis, myasthenia gravis, Sjogren's syndrome, Hashimoto's disease and Graves' disease, adrenalitis, hypoparathyroidism, and associated diseases; pernicious anemia; diabetes; multiple sclerosis and related demyelinating diseases; uveitis pemphigus and pemphigoid; cirrhosis and other diseases of the liver; ulcerative colitis; myocarditis; regional enteritis; adult respiratory distress syndrome; local manifestations of drug reactions (dermatitis, etc.); inflammation-associated or allergic reaction patterns of the skin; atopic dermatitis and infantile eczema; contact dermatitis, psoriasis lichen planus; allergic enteropathies; atopic diseases, e.g. allergic rhinitis and bronchial asthma; transplant rejection (heart, kidney, lung, liver, pancreatic islet cell, others); hypersensitivity or destructive responses to infectious agents; poststreptococcal diseases e.g. cardiac manifestations of rheumatic fever, etc.; tissue rejection during transplantation; and the like.

By treatment is meant at least an amelioration of the symptoms associated with the pathological condition afflicting the host, where amelioration is used in a broad sense to refer to at least a reduction in the magnitude of a parameter, e.g. symptom, associated with the pathological condition being treated, such as inflammation and pain associated therewith. As such, treatment also includes situations where the pathological condition, or at least symptoms associated therewith, are completely inhibited, e.g. prevented from happening, or stopped, e.g. terminated, such that the host no longer suffers from the pathological condition, or at least the symptoms that characterize the pathological condition.

A variety of hosts are treatable according to the subject methods. Generally such hosts are "mammals" or "mammalian," where these terms are used broadly to describe organisms which are within the class mammalia, including the orders carnivore (e.g., dogs and cats), rodentia (e.g., mice, guinea pigs, and rats), and primates (e.g., humans, chimpanzees, and monkeys). In many embodiments, the hosts will be humans.

Kits with unit doses of the active agent, usually in oral or injectable doses, are provided. In such kits, in addition to the containers containing the unit doses will be an informational package insert describing the use and attendant benefits of the drugs in treating pathological condition of interest. Preferred compounds and unit doses are those described herein above.

The following examples are offered primarily for purposes of illustration. It will be readily apparent to those skilled in the art that the formulations, dosages, methods of administration, and other parameters of this invention may be further modified or substituted in various ways without departing from the spirit and scope of the invention.

EXPERIMENTAL

I. Identification of GST-1 & GST-2

Human ESTs that are related to the C6ST/KSST at the protein level were searched by using TBLASTN which compares a protein query sequence against a nucleotide sequence database translated in all 6 reading frames. See Karlin, Samuel and Stephen F. Altschul (1990), Methods for assessing the statistical significance of molecular sequence features by using general scoring schemes, Proc. Natl. Acad. Sci. USA 87:2264–68; and Karlin, Samuel and Stephen F. Altschul (1993), Applications and statistics for multiple high-scoring segments in molecular sequences, Proc. Natl. Acad. Sci. USA 90:5873–7. As shown in Table 1, several ESTs, ranging from 228 to 861 bases, resulted in high scores. When compared over their entire length with the C6ST/KSST, the predicted amino acid identities ranged from 27% to 57%.

TABLE 1

Human ESTs related to the chick chondroitin 6/keratan sulfate sulfotransferase

| No. | mRNA source | Covering AA of C6ST/KSST | Identity of AA Sequences (%) | Contig Assignment |
|---|---|---|---|---|
| 1 | infant brain | 347–451 | 42 | 1 |
| 2 | infant brain | 140–216 | 57 | 1 |
| 3 | adult heart | 405–451 | 42 | 1 |

TABLE 1-continued

Human ESTs related to the chick chondroitin 6/keratan sulfate sulfotransferase

| No. | mRNA source | Covering AA of C6ST/KSST | Identity of AA Sequences (%) | Contig Assignment |
|---|---|---|---|---|
| 4 | fetal lung | 89–375 | 30 | 2 |
| 5 | fetal liver/spleen | 332–403 | 27 | 2 |
| 6 | teratocarcinoma | 100–165 | 31 | 2 |

The cDNA clones corresponding to each EST were obtained from the ATCC and Research Genetics, Inc.,(Huntsville, Ala.) and sequenced in full to obtain further 3' information. Sequence alignment analysis revealed the presence of two distinct sequences ("contigs"), covering 74% (contig 1, starting at amino acid 137) and 78% (contig 2, starting at amino acid 100). Contig sequences 1 and 2 are apparently both complete at the 3' end, since both contain poly A tracts at the end of their 3' untranslated regions (UTR).

Expression of transcripts corresponding to the two contigs was examined in a number of human tissues by Northern analysis. Blots of poly $A^+$ RNA (Clontech, Palo Alto, Calif.) were probed at high stringency with probes derived from the EST clones. A 3.1 kb band corresponding to contig 1 was detected in multiple human organs (heart, placenta, lung, liver, skeletal muscle, kidney, pancreas, spleen, lymph nodes, thymus) but most strongly in brain. Contig 2 was also broadly expressed in various organs (3.3 kb band), including lymph node and brain.

Full-length cDNAs containing the two contigs and predicting CS6T/KSST homologs were obtained by screening a human fetal brain λZAP cDNA library (Stratagene, La Jolla, Calif.) with labeled 700–800 bp restriction fragments (from EST 2 for contig 1 and from EST 5 for contig 2). Briefly, $10^6$ plaque-forming units were used to infect E. coli, which were then distributed on 20 plates. Duplicate filter lifts were performed. The probes were labeled with $^{32}P$ by random priming (Amersham), and hybridization was performed at 60° C. with high stringency washing. In both screens, multiple positive spots were obtained in the first round. Single positive clones were obtained after either the second or third round of screening. Multiple clones were sequenced for each gene and the presence of the ESTs was confirmed. As will be described below, the cDNAs contain open reading frames that encode predicted proteins of high homology to CS6T/KSST. The proteins encoded by these cDNAs were designated as GST 1 and GST 2, where "GST" denotes "glycosylsulfotransferase." GST 1 has been independently cloned and assigned the name "KSGal6ST" by Fukuta et al., J. Biol. Chem. (1997) 272: 32321–8.

II. Identification of HEC-GLCNAC6ST

ESTs potentially coding for human glycosyl sulfotransferases other than GST-1 & 2 were identified through a secondary homology screen, in which the peptide sequences of GST-1 and GST-2 were used as template in two parallel TBLASTN searches against a public (dbest) and a private genomic database (Lifeseq, Incyte Pharmaceuticals, Palo Alto, Calif.). Only matches that produced alignments with smallest sum probabilities $P(N)<10^{-5}$ were selected from the output of the search, imported into a contig assembler (Sequencher 3.0, Gene Codes Corporation, Ann Arbor, Mich.) and assembled using the default settings of the program. The vast majority of these matches assembled into two contigs defined by GST-1 and GST-2. However, four particular ESTs found only in the private Lifeseq database did not assemble into either contig or with each other. These were termed HEC-GLCNAC6ST through GST-6.

III. HEC-GLCNAC6ST is Expressed in High Endothelial Venules

In order to investigate if any of the above putative human glycosyl sulfotransferases or similar genes were expressed in high endothelial venules, an HEV-derived cDNA pool for use as template in homology polymerase chain reaction (PCR) was prepared. In order to clone HEV genes, an expression library from the aforementioned HEV-derived cDNA was also generated. Briefly, total RNA (45 µg) was isolated from $10^7$ HEC. Since the amount of poly $A^+$ RNA was too limited for preparation of a cDNA library by conventional procedures, the Capfinder (SMART™) cDNA technology (CLONTECH) was used. In this technique, the reverse transcription reaction is primed by a modified oligo (dT) primer (containing a Not I site) and a "SMART" oligonucleotide which anneals to an oligo dC stretch added by reverse transcriptase (RT) at the 3' end of the first strand cDNA. The annealed oligonucleotide serves as a "switch" template for RT, resulting in the generation of single stranded cDNAs which are enriched for full length sequences and contain universal primer sites for subsequent long distance PCR amplification. This technology therefore makes it possible to generate high quality double stranded cDNA (from limiting amounts of RNA), which is sufficient to construct a library. According to the published test results for this technology, Capfinder cDNA is comparable to conventionally prepared cDNA in gene representation and is significantly enriched for full length cDNAs. The HEC cDNA generated by the Capfinder technology was evaluated by PCR for the presence of the following genes, which are known or suspected to be expressed in HEC: CD34 (Baurrhueter et al., Science (1993) 262: 436–438), hevin (Girard & Springer, Immunity (1995) 2:113–123), fucosyltransferase VII (Maly et al., Cell (1996) 86: 643–653); β-1,6-N-acetylglucosaminyl-transferase (C2GnT) (Bierhuizen & Fukuda., Proc. Natl. Acad. Sci. USA (1992) 89: 9326–9330), and fractalkine (Schall, Immunology Today (1997) 18:147). By this analysis, all of these cDNAs were detected in the HEC cDNA, and at least two of them (CD34 and C2GnT) were full length. With this validation of the HEC cDNA, a library was generated as follows: the double-stranded cDNA was ligated to Eco RI adapters, digested with Not I and cloned into the Not I and Eco RI sites of pCDNA1.1 (Invitrogen, Inc, Carlsbad, Calif.), which is a modified version of the eucaryotic expression vector pCDM8 (Aruffo et al., Proc. Natl. Acad. Sci. USA (1987) 84: 8753–8577). The resulting libary has a complexity of 500, 000 independent clones and an average insert size of 1.1 kb, according to the characterization performed by CLONTECH.

HEV-derived Capfinder cDNA was used as a template for homology PCR with degenerate primers. In-frame translations of GST-1 and GST-2 were aligned with other known sulfotransferase protein sequences retrieved from the public databases. Three putative consensus regions were identified, and the following degenerate primers were synthesized to encode within these consensus regions a maximal number of possible permutations at the amino-acid level in order to cover a maximal number of sulfotransferases that may fall into these patterns.

These primers were (I=inosine):

A+: 5' TWYTWYCTITWYGARCCICTITGGCAYST 3'
B+: 5' CTIAAICTISTICWRCTISTIMGIRAYCC 3'
B–: 5' GGRTYICKIASIAGYWGIASIAGITTIAG 3'
C–: 5' AGRTCYTCRTAICKIAGIAGIAKRTA 3'

In the first round PCR each reaction contained in a total volume of 50 µl 100 mM Tris-Cl (pH 8.3), 0.5 M KCl, 15 mM MgCl₂, forward and reverse primer (0.5 µM each), dATP, dCTP, dGTP, and dTTP (100 µM each), 0.25 units *Thermus aquaticus* DNA polymerase (Boehringer Mannheim #1647679), and 0.5 µl of HEV-message derived Cap-finder cDNA preparation (generated by Clontech Inc., cf. above). In "no template" control samples the cDNA was omitted.

Each reaction was cycled as follows: hold 4 min @ 94° C., then 35 cycles of [30 sec @ 94° C. followed by 30 sec @ 40° C. followed by 1 min @ 72° C.], then hold 6 min @ 72° C. Following completion of PCR a 20 µl aliqout of each reaction was analysed by standard horizontal agarose (1%) gel electrophoresis. No discemable band pattern was observed (data not shown)

Therefore the unfractionated products of the first round PCR were used as template in a second round PCR. Here each reaction contained in a total volume of 50 µl 100 mM Tris-Cl (pH 8.3), 0.5 M KCl, 15 mM MgCl₂, forward and reverse primer (0.5 µM each), dATP, dCTP, dGTP, and dTTP (100 µM each), 0.25 units *Thermus aquaticus* DNA polymerase (Boehringer Mannheim #1647679), and 1 µl of total PCR reaction from round 1 (cf. above).

Each reaction was cycled as follows: hold 4 min @ 94° C., then 35 cycles of [30 sec @ 94° C. followed by 30 sec @ 45° C. followed by 1 min @ 72° C.], then hold 6 min @ 72° C. The entire reactions were then fractionated by standard horizontal agarose (1%) gel electrophoresis. Three bands appearing at positions 2.1, 2.2 and 2.3, were excised and DNA eluted from the gel using the QIAquick PCR purification kit (Qiagen Inc. #28104). Eluted DNA was then subcloned into the TA cloning vector pCR-II (stratagene) and *E-coli* transformed with recombinant plasmids. For each band eight colonies were expanded, and plasmid DNAs isolated and sequenced using standard dideoxynucleotide chain termination methodology with fluorimetric detection. In order to map the amplicons generated by the above homology PCR, public (dbest) and private (Incyte Inc.) EST databases were screened with by the TBLASTX algorithm (Karlin & Altschul, 1990 & 1993; cf. above) using the sequences of these amplicons as query sequences. Four sequences amplified from from HEV-cDNA with primers B+and C− aligned with >95% overall identity to Incyte EST #2620445 defined perviously as HEC-GLCNAC6ST (cf. above). All other query sequences did not pick up statistically significant matches in the specified databases.

IV. HEC-GLCNAC6ST is Expressed in HEC

From the extended DNA sequence of Lifeseq clone #2620445=HEC-GLCNAC6ST we designed a nondegenerate primer pair located within the incomplete open reading frame encoded by this EST.
Forward:5'AAACTCAAGAAGGAGGACCAACCCTA CTATGTGATGC 3' (SEQ ID NO:05)
Reverse:5'ATAAAGCTTGTGGATTTGTTCAGGGACA TTCCAGGTAGACAGAAGAT 3' (SEQ ID NO:6)
Using RT-PCR, a PCR product of appropriate length (500 bp) was amplified from HEC cDNA with this primer pair. This product could not be amplified from cDNAs prepared from tonsillar lymphocytes or primary cultured human umbilical vein endothelial cells (HUVEC). Control primers for hypoxanthine phosphoribosyl transferase (HPRT, a ubiquitously expressed cellular "housekeeping enzyme") were used in parallel to establish that similar amounts of template were used in each set of PCR reactions and that none of the template DNAs were substantially degraded. These RT-PCR results confirm that the gene corresponding to the PCR product is expressed in HEC but not in lymphocytes or HUVEC. Northern analysis has failed to detect mRNA for the new gene in a variety of human tissues and organs (but did detect a signal in liver, pancrease, lymph node and HEC, establishing that the expression of this gene is highly restricted. Also, by in situ hybridization, transcripts for mouse HEC-GLCNAC6ST were selectively found in lymph node HEV.

V. HEC-GLCNAC6ST Cloning

A full length cDNA from the HEC library described in the previous section was cloned as follows. The pool selection procedure described in Bakker et al., J. Biol. Chem. (1997) 272:29942–6) was used to quickly isolate the cDNA. It was first established that the relevant template was contained within the library by successfully amplifying the above described PCR product from the library stock comprising the entire library. An aliquot of this bacterial stock was then divided into 200 pools of 2000–3000 colonies each. Each pool was plated out on LB plates and the colonies were allowed to grow to a healthy size. The colonies were harvested in LB and allowed to grow further at 37° C., at which time glycerol stocks were prepared from each pool. By PCR analysis of the pools, nine positives were identified in this first round of screening. The corresponding bacterial stock for one of these pools was then titered and plated at 100 colony forming units (cfu) per plate in 40 plates. Plates were grown, harvested, preserved and analyzed as in the first round, resulting in the identification of three positive subpools. At this stage, one of the three positive pools was plated at a density (300 cfu) so that individual colonies could be analyzed by PCR. One cDNA clone was obtained by this approach. It contains a complete open reading frame which encodes a 386 amino acid protein, termed HEC-GLCNAC6ST. This full length cDNA sequence was then used as template in a BLASTN search of the public (dbest) and Lifeseq EST databases. In this manner, two so far unrecognized ESTs #2617407 (from Lifeseq; derived from a human gall bladder cDNA library) and g2262929 (from the mouse EST collection included in the dbest database, derived from a murine mammary gland cDNA library) were identified. The former EST included the 5' end of HEC-GLCNAC6ST open reading frame. Since this EST was generated with an oligo dT-primer, it therefore contains the entire open reading frame plus all 3' untranslated sequence of the human HEC-GLCNAC6ST cDNA. This EST was retrieved from Incyte in the form of a plasmid-transformed *E.coli* culture, expanded into Luria Bertoni Medium (with 0.1 mg/ml Ampicillin). The plasmid was isolated from a 500 ml culture and sequenced using standard dideoxynucleotide chain termination methodology with fluorimetric detection. Since no PCR-step was used in generating the full length HEC-GLCNAC6ST Lifeseq EST Incyte #2167407 (in contrast to the Cap-finder methodology employed in generation of our HEV-library), the HEC-GLCNAC6ST sequence obtained from Incyte #2617407 is free of PCR errors. The sequence is provided in SEQ ID NO:01 and shown in FIG. 1.

VI. Characterization of HEC-GLCNAC6ST

A. Three cDNA clones which encode three different human homologs for C6ST/KSST have been obtained. The predicted GST proteins are type 2 membrane proteins 411, 484, and 386 amino acids in length, respectively. Each has a relatively short transmembrane domain and a short aminoterminal cytoplasmic tail. Table 2 demontrates the high homologies among the 3 human proteins and the chick CS6T/KSST. Overall homologies at the amino acid level ranged from 28% to 40% identity. Strikingly, there are three regions of 16 to 29 amino acids in which identity among the three GSTs ranged from 50–59% and similarity ranged from 65–94%. All four of the sulfotransferases are type II transmembrane proteins with short cytoplasmic tails. There are three regions (region A, B and C) in which identities among the human GSTs range from 50–59% and similarities range from 65 to 94%. The amino acid sequence for the regions are:

A: (T/S)XRSGSSF(V/F)G(Q/E)LFXQX(P/L)(D/E)VF(F/Y)L(F/Y/M)EP(L/V/A)(W/Y)HV (SEQ ID NO: 33)
B: L(N/D)L(K/H)(V/I)(I/V)XLVRDPR(A/G)(V/I)(LAF) (SEQ ID NO: 34)
C: PXXL(Q/K)XXY(L/M)(L/V)VRYEDL(A/V)XXP (SEQ ID NO: 35)

TABLE 2

Percent amino acid identities for the predicted coding sequences

|       | GST 1 | GST 2 | GST 3 | CS6T/KSST |
|-------|-------|-------|-------|-----------|
| GST 1 | —     | 31    | 32    | 40        |
| GST 2 | —     | —     | 35    | 28        |
| GST 3 | —     | —     | —     | 31        |

B. GST-1 is the same as the sulfotransferase reported by Fukuta et al. supra (1997) and named KSGal6ST. HEC-GLCNAC6ST (HEC-GlcNAc6ST), is a GlcNAc-6sulfotransferase. These two sulfotransferases, together with the chicken C6/KSST (Fukuta et al., 1995, supra) and the recently reported human chondroitin-6-sulfotransferase (C6ST, specificity for C-6 of GalNAc, Fukuta, et al., Biophys. Acta. (1998)1399:57–61) and GlcNAc-6-sulfotransferase (GlcNAc6ST) (Uchimura et al., J. Biochem (Tokyo) (1998b)124:670–678) (which corresponds to GST-2) constitute a family of highly conserved enzymes. Overall amino acid identities within the family range from 27 to 42%. These enzymes are type II transmembrane proteins with short cytoplasmic tails, features which are typical of glycosyltransferases and carbohydrate sulfotransferases, with the exception of the heparan sulfate D-glucosamino-3-O-sulfotransferase (Shworak et al., 1997).

Within this new family of carbohydrate sulfotransferases, there are three regions of amino acid sequence in which amino acid identity ranges from 45–54% and similarity from 80–90%. Regions one and two contain elements that conform to the recently described consensus binding motifs for the high energy phosphate donor, 3'-phosphoadenosine-5'-phosphosulfate. These elements are found in all sulfotransferases characterized to date (Kakuta et al., Trends Biochem. Sci. (1998)23:129–130). In addition, regions one and three contain two stretches of sequence of 11 amino acids each (corresponding to amino acids 124–134 and 328–339, respectively, in the HEC-GlcNAc6ST sequence) that are highly conserved (>90% similarity). This suggests that these two elements contribute to a binding pocket that interacts with the 6-hydroxyl group of an appropriate oligosaccharide acceptor (Gal, GalNAc, or GlcNAc) to bring it into apposition with the donor phosphosulfate group.

VII. Characterization of HEC-GLCNAC6ST (HEC-GLCNAC6STT) and KSGAL6ST

A. HEC-GLCNAC6ST Sulfates GlyCAM-1

In expression experiments, the sulfotransferase activity of the HEC-GLCNAC6ST protein by transient expression of its cDNA into COS cells has been investigated. Since the HEC library yielding the GST 3 cDNA was in the pcDNA1.1 expression vector, there was no need to subclone the GST 3 insert prior to transfection. Co-transfection of the GST 3 cDNA with a cDNA encoding a GlyCAM-1/human IgG1 Fc chimera resulted in a >10 fold enhanced incorporation of $^{35}S$-$SO_4$ relative to transfection with the GlyCAM-1 chimera alone. Co-transfection with vector cDNA had no effect. By SDS-PAGE analysis, incorporation of $^{35}S$-$SO_4$ counts into the GlyCAM-1 chimera was confirmed. The results indicated that HEC-GLCNAC6ST encodes a sulfotransferase that can utilize GlyCAM-1 as an acceptor.

Figure 7:
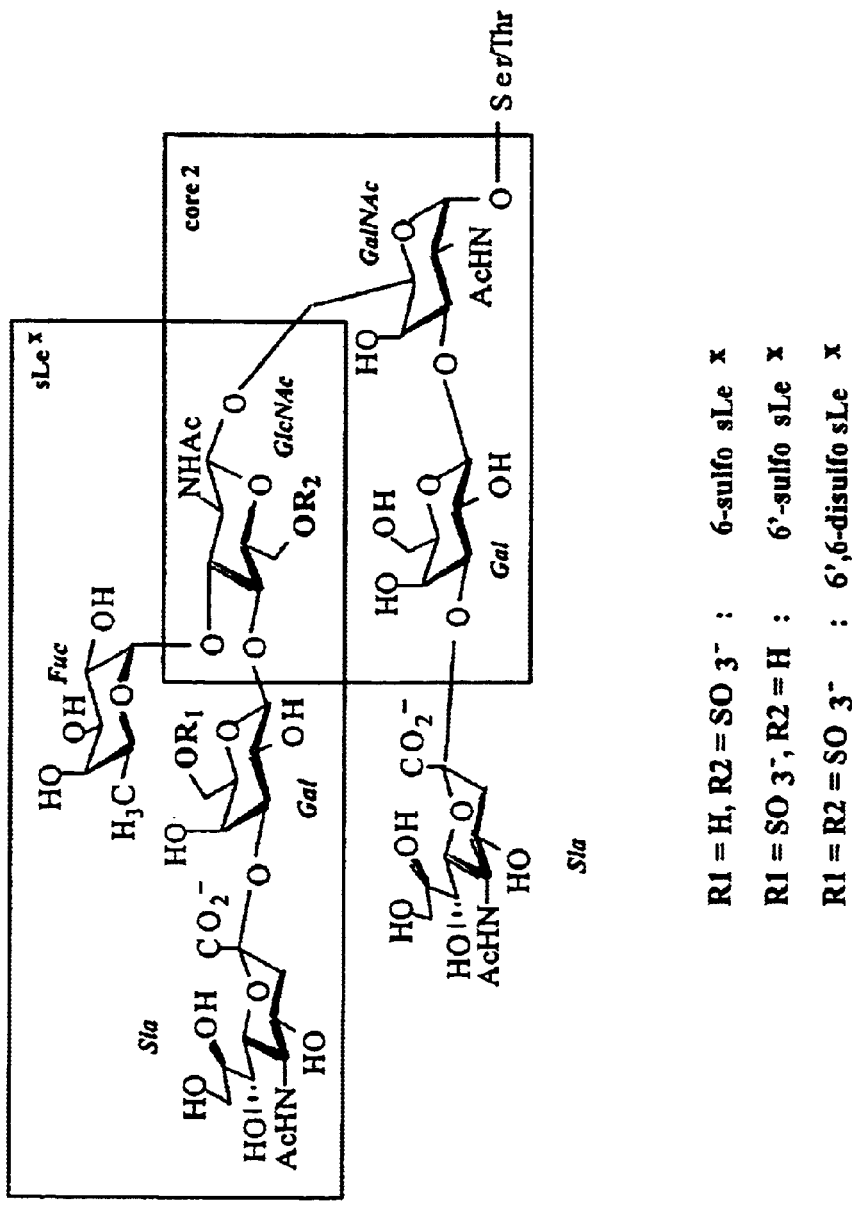
FIG. 7 provides the sulfated O-linked carbohydrate chains of GlyCAM-1. Oligosaccharides bearing the 6-sulfo sialyl Lewis x (sLe$^x$) and the 6'-sulfo sLe$^x$ motif, which extend from the core 2 structure are shown. The presence of the 6',6-disulfo sLe$^x$ motif is strongly suspected. Structures of the more complex O-linked chains of GlyCAM-1 remain to be determined.

B. Specificity of HEC-GLCNAC6ST (HEC-GlcNAc6ST) Defined with Synthetic Acceptors To define the activity of the protein encoded by the cDNA described above, the cDNA was expressed in COS cells and cellular extracts were tested for their ability to transfer $^{35}S$-sulfate from $^{35}S$-[3' phosphoadenosine 5' phosphosulfate] (PAPS) to synthetic oligosaccharide acceptors using the assay described in Bowman et al., Chem. and Biology (1998) 5:447–460. The disaccharide and trisaccharide acceptors (Table 3) were based on core structures of GlyCAM-1 chains (FIG. 7) with the substitution of Gal for GalNAc at the reducing termini.

TABLE 3

Nomenclature and Structure of Oligosaccharides and Substituents

| Name | Structure |
|------|-----------|
| sLe$^x$ (sialyl Lewis x) | Siaα2→3Galβ1→4[Fucα1→3]GlcNAc |
| 6'-sulfo sLe$^x$ | Siaα2→3[$SO_3$→6]Galβ1→4[Fucα1→3]GlcNAc |
| 6-sulfo sLe$^x$ | Siaα2→3Galβ1→4[Fucα1→3][$SO_3$→6]GlcNAc |
| 6',6-disulfo sLe$^x$ | Siaα2→3[$SO_3$→6]Galβ1→4[Fucα1→3][$SO_3$→6]GlcNAc |
| core 2 | Galβ1→3[GlcNAcβ1→6]GalNAc |
| disaccharide acceptor | GlcNAcβ1→6Galα1-R |
| trisaccharide acceptor | Galβ1→4GlcNAcβ1→6Galα1-R |
| R | C-$CH_2$—$CH_2$—$CONH_2$—($CH_2$)$_7$—$CH_3$ |

Substantial radioactivity was transferred to the disaccharide acceptor GlcNAcβ1→6Galα-R, but the activity towards the trisaccharide acceptor Galβ1→4GlcNAcβ1→6Galα-R was barely above the control generated by an extract from mock-transfected cells. The position and regiochemistry of sulfation was established by HPAEC analysis using a previously described protocol (Bowman et al., 1998, supra). Label was associated exclusively with GlcNAc-6-sulfate. This analysis establishes that this cDNA encodes a GlcNAc-6-sulfotransferase, providing the basis for the designation HEC-GlcNAc6ST. Furthermore, the enzyme requires a terminal GlcNAc residue for recognition, mirroring the profile of activity observed previously in extracts of isolated HEC (Bowman et al., 1998, supra).

C. Sulfation of GlyCAM-1 by KSGal6ST (GST-1) and HEC-GlcNAc6ST (HEC-GLCNAC6ST)

To test whether KSGal6ST and HEC-GlcNAc6ST were capable of sulfating a bonafide L-selectin ligand in cells, COS cells were transfected with a cDNA encoding a GlyCAM-1/IgG chimera and a cDNA encoding one or the other sulfotransferase. The transfected cells were cultured in the presence of $^{35}S$-sulfate and radiolabeled GlyCAM-1/Ig was purified from the conditioned medium on protein A-agarose. It was found that substantial incorporation of counts occurred when GlyCAM-1/IgG (66 kDa) was cotransfected with either KSGal6ST or HEC-GlcNAc6ST cDNA but not with the empty vector.

In order to establish the regiochemistry of sulfation on radiolabeted GlyCAM-1/IgG, samples resulting from the two sulfotransferase transfections were subjected to hydrolysis and analysis by HPAEC, using a Dionex HPLC system according to the previously established procedures (Hemmerich et al., Biochem. (1994)33:4820–4829). The retention times of the released sulfated mono- and disaccharides corresponded to those of authentic standards for [SO$_3$→6]Gal and [SO$_3$→6]Galβ1→4GlcNAc for the KSGal6ST transfectants and to [SO$_3$→6]GlcNAc and Galβ1→4[SO$_3$→6]GlcNAc for the HEC-GlcNAc6ST transfectants. Thus, the specificities of KSGal6ST and HEC-GlcNAc6ST for oligosaccharides of GlyCAM-1 reflected those observed with the model acceptors (Fukuta et al., 1997).

D. Contribution of KSGal6ST and HEC-GlcNAc6ST to the Generation of L-selectin Ligand Activity In order to test whether KSGal6ST and HEC-GlcNAc6ST can contribute to the generation of L-selectin ligand activity, the binding of an L-selectin/IgM chimera to CHO cells which were transiently transfected with cDNAs for the sulfotransferases and a cDNA encoding CD34 was examined. The recipient CHO cells, termed CHO/FTVII/C2GnT, were stably transfected with 1) fucosyltransferase VII (FucTVII), which is known to be involved in the biosynthesis of L-selectin ligands (Maly et al., Cell (1996) 643–653); and 2) core 2 β1→6 N-acetylglucosaminyltransferase (C2GnT) (Bierhuizen and Fukuda, Proc. Nat'l Acad. Sci. USA (1992)89:9326–9330). This latter enzyme provides a core structure for O-linked glycans upon which extended chains with sLe$^x$ capping groups are elaborated (Li et al., J. Biol.Chem (1996) 271:3255–3264). Binding was measured by flow cytometry. No L-selectin/IgM staining above background was observed in the CHO cell transfectants in the absence of sulfotransferase cDNA. Strong L-selectin/IgM binding was observed in a significant population of the cells when both HEC-GlcNAc6ST and KSGal6ST cDNAs were included in the transfection. The binding of the L-selectin/IgM chimera was specific as indicated by its calcium dependence (data not shown) and the inhibition of its binding by a function-blocking anti-L-selectin mAb (MEL-14). The binding of L-selectin/IgM was dependent on the presence of the CD34 protein scaffold, as indicated by the nearly complete loss of staining when the CD34 cDNA was omitted from the transfection. To determine the individual contribution of the two sulfotransferases to L-selectin binding, the CHO cells were cotransfected with cDNAs for 1) CD34 and 2) the sulfotransferases, alone or in combination. Transfection with either HEC-GlcNAc6ST or KSGal6ST cDNA conferred binding of the L-selectin/IgM chimera. KSGal6ST appeared to exert the greater effect, both in terms of the proportion of positive cells and their mean fluorescence intensity. However, the combination of KSGal6ST and HEC-GlcNAc6ST cDNAs strongly enhanced the binding of L-selectin/IgM relative to the the single sulfotransferase transfectants. Moreover, the signal resulting from the combination clearly exceeded the sum of the signals from the individual transfections, indicating that the two sulfotransferases synergized to generate ligand activity. This synergistic effect was evident over a range of cDNA concentrations in the transfection mixtures (Table 4).

TABLE 4

L-Selectin/IgM Staining of CHO Cells Transfected with Combinations of Sulfotransferase cDNAs

| μg cDNA transfected | | MFI |
|---|---|---|
| KSGal6ST | HEC-GlcNAc6ST | L-sel-IgM Staining |
| 1.0 | 0 | 364 |
| 1.5 | 0 | 391 |
| 0 | 1 | 114 |
| 0 | 1.5 | 163 |
| 0.5 | 0.5 | 935 |
| 1 | 0.5 | 917 |
| 0.5 | 1.0 | 830 |

CHO/FTVII/C2GnT cells were cotransfected with plasmids encoding CD34 (2 μg) and each sulfotransferase alone or in combination in the indicated amounts. Data are expressed as the mean fluorescence intensity (MFI) of L-selectin/IgM staining in the L-sel-IgM$^+$/CD34$^+$ population with background signal (from transfectants with CD34 cDNA alone, value 139) subtracted.

VIII. Rolling Data in a Parallel Plate Flow Chamber

A. Methods

1. Transient Transfection of COS-7 Cells

For generation of recombinant GlyCAM-1/IG fusion protein, COS-7 cells were grown to 80% confluency in 10 cm culture dishes (Nunc) and transfected with plasmids encoding core 2 β-1,6-N-acetylglucosminyltransferase (C2Gnt) (1 μg), fucosyltransferase VII (FT-VII) (1 μg), GlyCAM-1/IgG (2 μg) and 0.5, 1 or 2 μg of either KSGaL6ST, huGlcNAc6ST, HEC-GlcNAc6ST, or irrelevant control plasmid (mock control), using Lipofectamine (Life Technologies) in Opti-MEM (Life Technologies) according to the manufacturer's protocol. Cells were grown for seven days in Opti-MEM/penicillin/streptavidin. Recombinant GlyCAM-1/IgG fusion protein was isolated from the conditioned medium (CM) by affinity chromatography on protein A-agarose and transferred to PBS on a Centricon 30 concentrator (Amicon, Beverly, Mass.).

2. Laminar Flow Assays

The GlyCAM-1/IgG constructs were coated at similar site densities onto polystyrene dishes (Corning, San Mateo, Calif.) as determined by ELISA using 96 well polystyrene plates (Costar, Corning, N.Y.). Proteins were coated in Tris-buffered saline (TBS), pH 9.0 overnight at 4° C., washed and blocked with 3% BSA. The immobilized GlyCAM-1/IG constructs were detected by ELISA with biotinylated CAMO-5 or biotinylated anti human IgG (Fc specific) and streptavidin conjugated alkaline phosphatase. For flow experiments the substrate-coated dishes were incorporated as the lower wall of a parallel plate flow chamber (Lawrence et al., Cell (1991) 65:859–873) and mounted on the stage of an inverted phase-contrast microscope microscope (Diaphot TMD; Nikon Inc., Garden City, N.Y.). Jurkat cells were perfused through the flow chamber at 1–2×10$^6$ cells/ml in HBSS with Ca$^+$ or Mg$^+$ supplemented with 0.2% BSA. For inhibition studies, cells were treated with 5 μg/ml DREG56 (anti L-selectin mAb), 10 μg/ml Fucoidin (a carbohydrate inhibitor of L-selectin) for 10 min at room temperature prior to injection into the flow chamber or perfused in 5 mM EDTA/HBSS/0.2% BSA. In some cases, substrates were incubated with 5 mU/ml Vibrio cholera sialidase (Oxford Glycosystems, Rosedale, N.Y.) for 30 min in 50 mM sodium acetate, 4 mM CaCl$_2$, 0.1% BSA, pH 5.5 or as a control with buffer alone.

Experiments were videotaped using a 4x objective (field of view—1.91 mm²) and data were analyzed on a computer using NIH Image 1.61. For tethering, cells were perfused through the chamber at different shear stresses covering a range from 3 dynes/cm² to 0.2 dynes/cm². The fraction of cells that came into close proximity with the substrate and tethered stably (cells that continued to roll for >1s on the substrate after the initial attachment) was determined. For rolling velocities, cells were infused for 2 min at 1 dyne/cm² after which shear stress was increased in 1.5 to twofold increments up to 35 dynes/cm² in intervals of 5 s (detachment assay). Cell displacement was followed for 1–3 seconds to determine rolling velocities at each shear stress. In detachment assays the number of rolling cells at each shear stress was determined. The maximum number of adherent cells was set to 100%, and the number of rolling cells at higher shear stresses was expressed relative to this peak accumulation value. In all experiments the observation field was located at the upstream edge of the spot of adsorbed protein to minimize contribution of cells rolling into the fields from upstream fields.

B. Results

1. Jurkat Cells Roll on Fucosylated and Sulfated GlyCAM-1/IgG in Shear Flow

The binding of L-selectin to its HEV-ligands requires sialylation, fucosylation (Maly et al., 1996) and sulfation. Maly et al. established that FucT-VII is the relevant fucosyltransferase for the elaboration of functional L-selectin ligands in HEC. Our previous structural analysis indicated that Gal-6-sulfate and GlcNAc-6-sulfate are equally present in native GlyCAM-1 oligosaccharides and that both reside within the sLe$^x$-based capping structures (6'-sulfo sLe$^x$ and 6-sulfo s sLe$^x$, respectively). In order to test how these sulfation modifications contribute to the generation of L-selectin ligand activity the rolling of Jurkat cells on immobilized, fucosylated, and sulfated rGlyCAM-1/IgG fusion proteins under shear flow conditions was examined. COS cells, which have endogenous sialyl transferase activity, were cotransfected with cDNAs for C2GnT, FucT-VII, GlyCAM-1/IgG and either KSGal6ST, huGlcNAc6ST, HEC-GLCNAC6ST or control plasmid. Recombinant GlyCAM-1/IgG fusion proteins were purified from the conditioned medium on protein A-agarose.

For flow assays the recombinant proteins were coated at equal site densities as determined by ELISA (data not shown). Detection of the immobilized GlyCAM-1/IgG substrates with the anti-GlyCAM-1 antibody CAMO-5 or an anti-human IgG (Fc specific) mAb demonstrated the same level of binding of the various chimeras. Rolling of Jurkat cells on the substrates at a shear stress of 1 dyne/cm² required the fucosylation of GlyCAM-1/IgG, as no rolling interactions were observed on GlyCAM-1/IgG or sulfated, non-fucosylated GlyCAM-1/IgG (Table 5). Sulfation of C-6 of either Gal or GlcNAc yielded an increase in the number of rolling cells, however the effect was more pronounced for the Gal-6-sulfated substrate. An anti-L-selectin mAb abrogated the interaction with the substrate as did fucoidin, an anionic polysaccharide that blocks L-selectin-dependent binding. Treatment of the substrates with sialidase from Vibrio cholera completely prevented Jurkat cell tethering as previously seen for lymphocyte tethering onto PNAd and CD34 (Puri et al., 1995) or HEV (Rosen et al., 1985) (Table 5).

TABLE 5

Characteristics of the interaction of Jurkat cells with rGlyCAM-1/IgG fusion proteins

| substrate | Rolling[1] | EDTA[2] | anti L-selectin mAb[2] | Fucoidin[2] | sialidase[3] |
|---|---|---|---|---|---|
| rGlyCAM-1/IgG | 0 | | | | |
| rGlyCAM-1/IgG FT | 12.2 ± 5 | 0 | 0 | 0 | 0 |
| rGlyCAM-1/IgG KSGal6ST | 0 | | | | |
| rGlyCAM-1/IgG huGlcNAc6ST | 0 | | | | |
| rGlyCAM-1/IgG HEC-GlcNAc6ST | 0 | | | | |
| rGlyCAM-1/IgG FT KSGal6ST | 107.0 ± 16.7 | — | — | — | — |
| rGlyCAM-1/IgG FT huGlcNAc6ST | 36.1 ± 15.3 | — | — | — | — |
| rGlyCAM-1/IgG FT HEC-GlcNAc6ST | 36.6 ± 9.5 | — | — | — | — |

[1]Jurkat cells were perfused through the flow chamber at 1 dyne/cm² at 1–2 × 10⁶ cells/ml and the number of rolling cells was evaluated at 2 min of flow.
[2]Cells were treated with 5 μg/ml DREG56, 10 μg/ml Fucoidin for 10 min at room temperature prior to injection into the flow chamber or perfused in 5 mM EDTA/HBSS/0.2% BSA to inhibit L-selectin mediated rolling.
[3]Immobilized GlyCAM-1/Ig fusion proteins were treated with 5 mU/ml Vibrio cholera sialidase as describes in Methods.
[4]'0' indicates that no rolling of cells was detected.

2. Sulfation of Fucosylated rGlyCAM-1 Enhances L-selectin Mediated Interactions in Shear Flow To determine the contribution of sulfation to tethering under laminar flow conditions, Jurkat cells were perfused through a parallel wall flow chamber in which fucosylated GlyCAM-1/IgG constructs with or without sulfate modifications were coated at the same site densities. Jurkat cells showed the tethering profile characteristic for L-selectin with a shear threshold below which no or little tethering occurred. While a maximum tethering rate of 9% was found for the interaction of cells with non-sulfated GlyCAM-1/IgG (FT), the fraction of tethered cells was doubled upon sulfation on C-6 of GlcNAc (FT, huGlcNAc6ST; FT, HEC-GlcNac6ST) and increased sixfold upon sulfation C-6 of Gal (FT, KSGal6ST). Furthermore, the latter modification resulted also in a shift of the tethering threshold towards lower shear stresses.

Sulfation of C-6 of GlcNAc reduced the velocity of rolling cells consistently relative to the velocities observed on non-sulfated GlyCAM-1/IG. The reduction in velocity was more pronounced on the Gal-6 sulfated substrate than on the substrates with GlcNAc-6 modifications. Gal-6 sulfation resulted in cells that were more resistant to detachment at increased shear stresses indicating an increase in binding strength. Small increases in binding strength were observed on GlcNAc-6 modified substrates.

IX. Identification and Characterization of Mouse HEC-GLCNAC6ST

A. Identification of EST

This peptide sequence for hu HEC-GLCNAC6ST (FIG. 2; SEQ ID NO:02) was used as template to screen the murine sequences contained within the public EST database (deEST) using the tBLASTn algorithm (reference to be found in original patent application). This screen identified a mouse EST (accession #AA522181) that mapped to huGST3 with 75% identity on the amino acid level. This mouse EST however contained only the last 20% of the total open reading frame based on comparison to the human sequence.

B. Expression Pattern

In order to obtain information on the expression pattern of the mouse gene, the above EST was retrieved and used in the following a in situ hybridization assay. Paraffin sections (5 µm) from C57BL6 mice were deparaffinized, fixed in 4% paraformaldehyde and treated with proteinase K. After washing in 0.5×SSC, the sections were covered with hybridization solution (50% formamide, 300 mM NaCl, 20 mM Tris, pH 8.0, 5 mM EDTA, 1× Denhardt's, 10% Dextran sulfate, 10 mM DTT), prehybridized for 1–3 hr at 55° C., and hybridized overnight with sense or antisense $^{35}$S-labeled riboprobe transcribed from the IMAGE consortium clone 851801 (GenBank accession no. AA522184) (Research Genetics, Inc., Huntsville Ala.) which had been modified by digestion with Sac I followed by religation. After hybridization, sections were washed at high stringency, dehydrated, dipped in photographic emulsion NTB2 (Eastman Kodak Company, Rochester, N.Y.), stored at 4° C. for 2–8 weeks, developed and counterstained with hematoxylin and eosin.

Strikingly, murine HEC-GlcNAc6ST transcripts were detected only in the HEV of lymph node. No hybridizing signal was found in other cell types of the lymph node, or in several other organs, including spleen, thymus, liver, skeletal muscle, pancreas, stomach, and kidney. A weak signal was detected in gut intestinal epithelium. The sense control did not yield signal in any tissue.

C. Cloning of Mouse HEC-GlcNAc6ST

Fucosyltransferases and N-acetylgalactosminyl transferases are enzymes topologically related to glycosyl sulfotransferases. Since the genes encoding the former group of enzymes are often intron-less, it was assumed that mouse glycosyl sulfotransferase 3 may be intronless as well. A 240 bp cDNA fragment located within the partial open reading frame contained within EST AA522184 was amplified. The probe was used to identify a BAC clone from C56Bl/6 mouse. This BAC was retrieved, amplified, and sequenced directly, starting with primers derived from EST AA522184. The sequence of the cDNA is provided in FIG. 3, where the open reading frame (ORF) is identified in capital letters. The open reading frame encodes a protein having the sequence shown in FIG. 4. Comparison of the human and the mouse HEC-GLCNAC6ST at the protein level using the GAP program (GCG package) showed 79.221% similarity and 72.468% identity.

X. Further Characterization of HEC-GlcNAc6ST-Knockout Mice Studies

A. Methods and Materials

1. Generation of HEC-GlcNAc6ST Deficient Mice

An approximately 4.9 kb genomic fragment including the protein coding region of the HEC-GlcNAc6ST gene was isolated from a mouse genomic library and subcloned into the BamH1 site of the pBluescript II SK(−) vector. A 98 bp fragment corresponding to a segment of the protein-coding region was replaced by an IRES-lacZ reporter and neomycin resistance cassette (IRES-lacZ-neo). This mutation was designed to produce a loss of function mutation by deletion of amino acids 46–78 as well as insertion of the 6.5 kb IRES-lacZ-neo cassette. The IRES-lacZ-neo cassette was flanked by 0.9 kb of mouse genomic DNA at its 5' aspect and by 4.0 kb of mouse genomic DNA at its 3' aspect. The targeting vector was linearized and electroporated into mouse embryonic stem cells. ES cells were selected for G418 resistance and colonies carrying homologous integration events were identified by PCR amplification with a neo specific primer and a primer specific for a sequence outside of the targeting vector homology region. Colonies that gave rise to the correct size PCR products on agarose gel electrophoresis were confirmed by Southern blot analysis using genomic probes adjacent to the 5' and 3' regions of homology. The presence of a single IRES-lacZ-neo cassette was confirmed by Southern blot analysis using a neomycin gene fragment as a probe. Male chimeric mice were produced by injection of the targeted ES cells into C57Bl/6 blastocysts. Chimeric mice were bred with C57Bl/6 mice to produce F1 heterozygotes. Germline transmission was confirmed by PCR and Southern analysis. F1 heterozygous males and females were mated to produce F2 wild-type, heterozygous, and homozygous mutant animals.

For the Southern analysis of the F2 mice, genomic DNA was purified from the liver of HEC-GlcNAc6ST +/+, +/− and −/− mice. 30 µg of DNA from each sample was digested with EcoRV, transferred to a nitrocellulose membrane, and hybridized using end-labeled overlapping 3' external genomic probes:

5' CAAGAGTGTTTTCTAAATACAGTATTGTAGAAA GTAATTGCCAATAGCATGAGTCTGGA-3' and
5' TAAACCTATGGAATGAATAAAGGCATGCTTGA CAAAAAGTCATATCCAGACTCATGCTA-3' (SEQ ID NOS: 08 & 09).

For the RT-PCR analysis of the F2 mice, total RNA was purified from peripheral lymph nodes and mesenteric lymph nodes of HEC-GlcNAc6ST +/+ and −/− mouse by lysis and extraction with RNAZol (Tet-Test Inc, Friendwood, Tex.). cDNA was synthesized from the total RNA using random hexamers for priming and AMV reverse transcriptase. PCR reactions were carried with the cDNAs and the following primers pairs:

KSGal6ST:
5' primer: 5'-AGTCATGTGGCCATCAAGACTGTGCGGGTG
3' Primer: 5'-GGGAGATAAGGCAACAGTTAAAGACGGCCC (SEQ ID NOS: 10 & 11)

HEC-GlcNAc6ST:
5' primer: 5'-CATGGGTCAGCATGCCTTCCATACTAACGCCA
3' primer: 5'-CTCTGCTTGGGGCTGAGGAGAAAGGGGCACTC (SEQ ID NOS: 12 & 13)

GlcNAc6ST:
5' primer: 5'-GCCTACCGCAAGGAGGTCGTCGGACTGGTGG AC
3' primer: 5'-ACTGTTAACCCGCTCATAGCCCAGCACGGCCAT (SEQ ID NOS: 14 & 15)

HPRT:
5' primer: 5'-CCTGCTGGATTACATCAAAGCACTG
3' primer: 5'-TCCAACACTTCGTGGGGTCCT (SEQ ID NOS: 16 & 17).

The PCR products from two-fold serial dilutions of cDNAs were analyzed by agarose electrophoresis and ethidium bromide staining.

2. Statistical Analyses

Figure 9C:
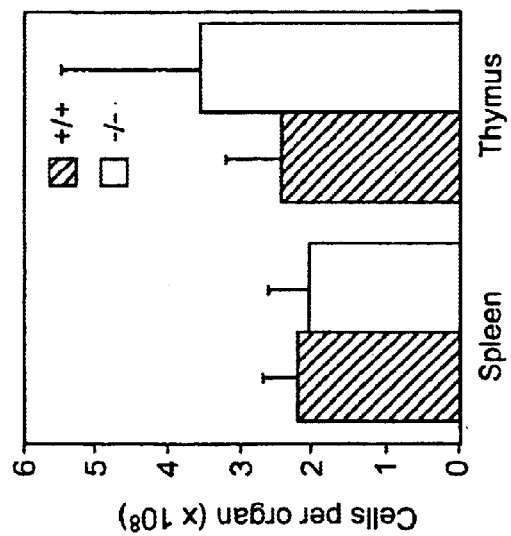
FIGS. 9A to 9C. Leukocyte Distribution in Blood and Lymphoid Organs of HEC-GlcNAc6ST Null Mice. (9A) Leukocytes were counted in the blood of wild-type (+/+) and HEC-GlcNAc6ST null mice. WBC, PMN, L, and M indicate total white blood cell, neutrophil, lymphocyte, and monocyte counts, respectively. 8 +/+ and 8 –/– mice were compared. (9B, 9C). Lymphocyte counts were determined in mechanically dissociated lymphoid organs from 6 +/+ and 6 –/– mice. In 9A, 9B, and 9C error bars indicate SEM values. In A, none of the +/+ vs. –/– differences were statistically significant (p>0.05). In 9B and 9C, the difference in the number of lymphocytes in PN between +/+ and –/– mice was significant (p value of 0.02)
Figure 9B:
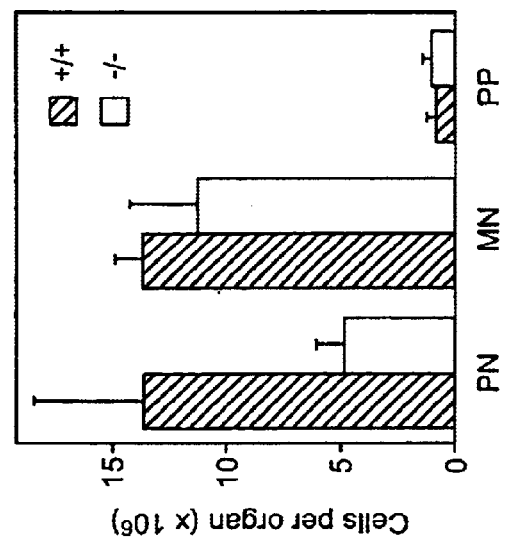
Figure 9A:
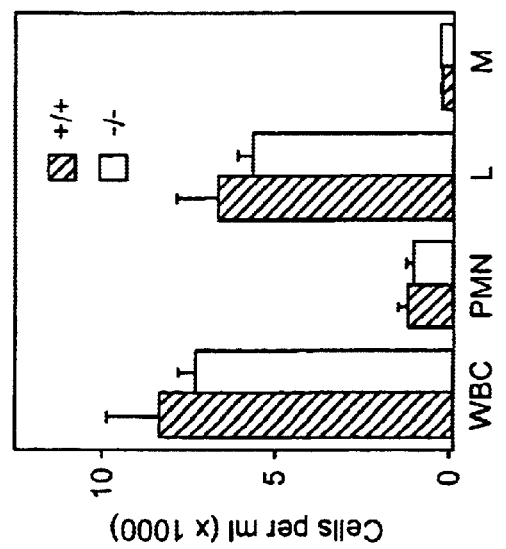
Figure 10:
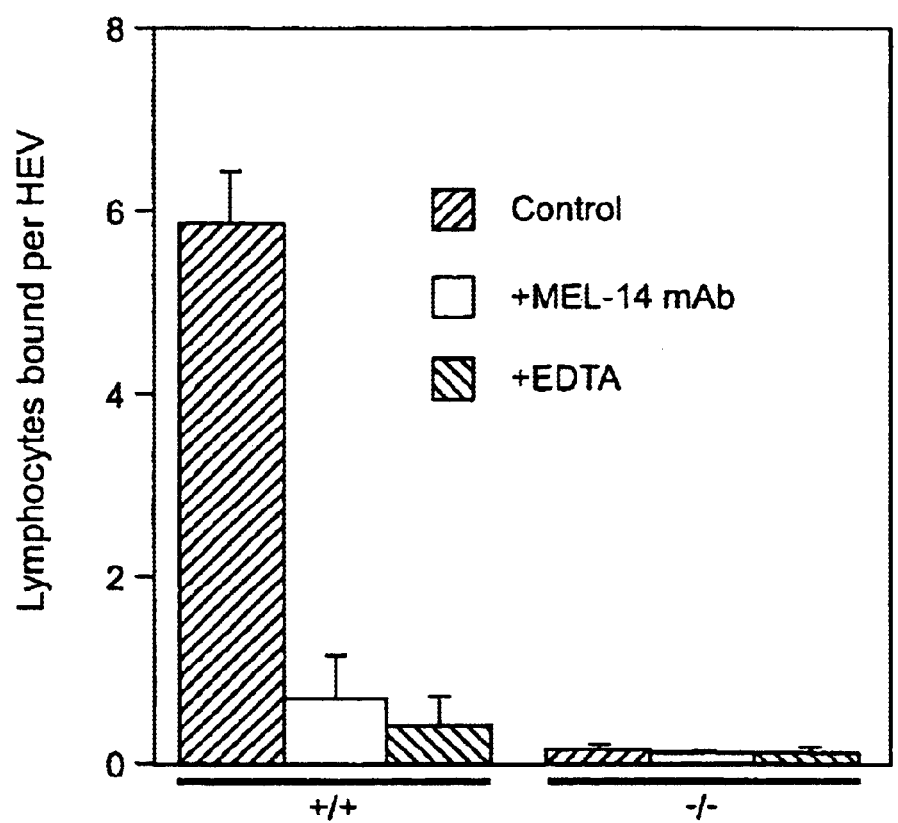
FIG. 10. In Vitro Adherence of Lymphocytes to HEV. Sections of peripheral lymph nodes from +/+ and HEC-GlcNAc6ST null mice (–/–) were used in the Stamper-Woodruff in vitro adherence assay. EDTA or anti-L-selectin mAb (MEL-14) were included to determine the contribution of L-selectin to adherence. 4 independent sections were used for each condition. Exogenous lymphocytes that had attached to HEV profiles in the sections were enumerated and the mean number of bound lymphocytes per HEV profile was determined. Error bars denote SEMs derived from the analysis of 4 independent sections per treatment. The difference in the number of lymphocytes that attached to +/+ vs. –/– sections was significant (p value of 0.029). The effects of MEL-14 and EDTA on lymphocyte attachment to +/+ sections were also significant at the same levels.
Figure 11:
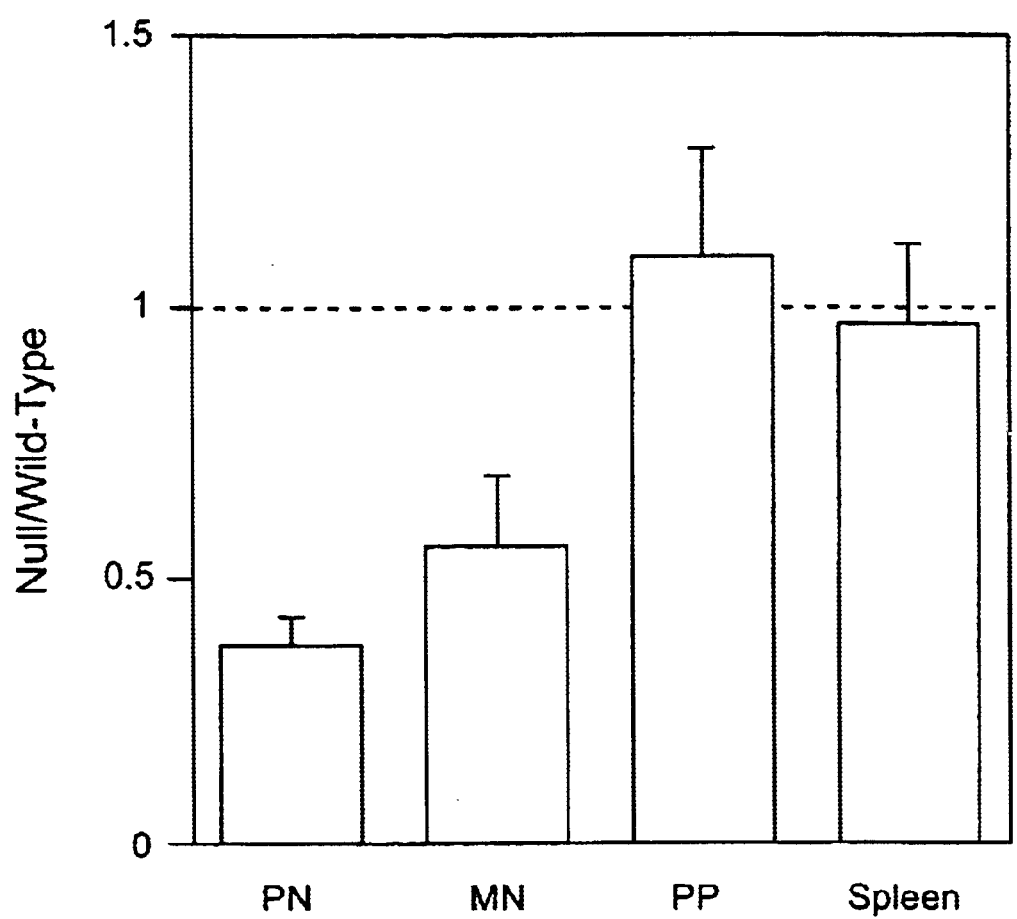
FIG. 11. Homing of Lymphocytes. Fluorescently-labeled lymphocytes were injected intravenously into +/+ and HEC-GlcNAc6ST null mice (–/–). After 1 hr, peripheral lymph nodes (PN), mesenteric lymph nodes (MN), Peyer's patches (PP), and spleen were isolated and dissociated into single cell suspensions. The number of fluorescent was determined by flow cytometry as a percentage of unlabeled lymphocytes. Homing in the null animals (–/–) is shown as a fraction of that observed in the wild-type animals, which is set at 1. Data were pooled from 3 separate experiments in which a total of 8 +/+ and 10 –/– animals were used. Error bars denote SEMs. The –/– mice showed significantly reduced homing to both PN and MN relative to that in the +/+ mice (p values of 0.0004 and 0.016, respectively). Homing to PP and spleen were not significantly different between –/– and +/+ mice.

The statistical comparisons performed in FIGS. 9, 10, and 11 were calculated with the two-tailed Mann-Whitney test. The choice of this nonparametric test, instead of the Student t-test, was dictated by the fact that the variances between comparison groups were not equivalent.

3. Analysis of Blood and Lymphoid Organs

Blood was obtained from mice (5–10 week old) by cardiac puncture and placed in Microtainer tubes containing EDTA (Beckton Dickenson, Franklin Lakes, N.J.) and stored at 4° C. until analysis. A complete hematological profile was obtained using a Hemavet 850 automated hematological analyzer (CDC Technologies Inc., Oxford, Conn.). Freshly isolated lymphoid organs (5–7 week old mice) were weighed directly. The peripheral lymph nodes consisted of pooled axillary and brachial nodes. For cell counts, the lymphoid organs were placed in cold PBS and teased with two 23-G needles to create a uniform single-cell suspension. The resulting suspension was rinsed with PBS through a 100 $\mu$m nylon cell strainer (Falcon, Franklin Lakes, N.J.). Viable nucleated cells (the vast majority of which were lymphocytes) were counted by hemocytometer using the criterion of trypan blue exclusion.

4. Histology Procedures

Conventional Histology: 10 week old mice were sacrificed, peripheral lymph nodes (axillary and brachial) were removed and fixed in 4% paraformaldehyde in 0.1 M sodium cacodylate, pH 7.3 at room temperature for 5 hours and then overnight at 4° C. After alcohol dehydration, the tissue was embedded in paraffin and 2 $\mu$m sections cut and stained with hematoxylin and eosin.

L- and E-selectin/IgM Chimera Staining of Peripheral Lymph Nodes: Axillary and brachial lymph nodes from 10-week old HEC-GlcNAC6ST −/− and +/+ mice were dissected, embedded in O.C.T.(Tissue Tek/Fisher Scientific; Pittsburgh, Pa.), and frozen in 2-methylbutane cooled in liquid nitrogen. 10 $\mu$m sections were cut, picked up onto Superfrost Plus slides (Fisher Scientific), air dried for 10 minutes, and fixed in 1% paraformaldehyde in 0.1 M sodium cacodylate, pH 7.3 for 20 minutes on ice. After washing with PBS the tissue was incubated with 5% normal goat serum in PBS (block) for 10 minutes at 4° C. L-selectin/IgM, secreted into OptiMEM (Gibco/BRL; Grand Island, N.Y.) after transfection of COS7 cells with the plasmid, was concentrated 6-fold and then diluted 1/4 in block. E-selectin/IgM, a gift from Dr. Lloyd Stoolman (University of Michigan) was diluted 1/16 in block. Both selectin chimeras were incubated with the tissue for 30 minutes at 4° C. After washing in PBS, the tissue was incubated with a 1/500 dilution of biotinylated goat anti-human IgM (Caltag Laboratories; S. San Francisco, Calif.) in block for 30 minutes at RT. After washing in PBS, the tissue was incubated with a 1/500 dilution of streptavidin-HRP (Caltag) in PBS for 30 minutes at RT. Chromagen development was with NovaRed (Vector Laboratories; Burlingame, Calif.).

Antibody Staining of Lymph Nodes and Peyer's Patches: same procedure as except primary antibody incubation was for 1 hour at RT. All antibodies were diluted in block. MECA-367 (rat IgG2a; gift from Dr. Eugene Butcher, Stanford University) was used at 5 $\mu$g/ml; MECA-79 (rat IgM; ascites, Caltag) was used at 1 $\mu$g/ml; anti-CD31 (rat IgG2a, BD Pharmingen; San Diego, Calif.) were used at 1 $\mu$g/ml. Control rat IgM (Caltag) and rat IgG2a (BD Pharmingen) were used at the equivalent experimental concentrations. After washing in PBS, 1/500 dilution in block of biotinylated goat anti-rat IgG (Caltag) was added to the wells with rat IgG2a; 1/500 dilution in block of biotinylated mouse anti-rat IgM (Caltag) to the wells with rat IgM and incubated for 30 minutes at RT. After washing with PBS, streptavidin-HRP addition and chromagen development were performed as above.

5. In Vitro Adherence Assay

Axillary and brachial lymph nodes from 10-week old GST3 −/− and +/+ mice were dissected in O.C.T., and frozen in 2-methylbutane cooled in liquid nitrogen. The assay was performed as we have previously described (Rosen, et al., J. Immunol. (1989) 142, 1895–1902.). Briefly, 10 $\mu$m sections were cut, picked up on 3-well epoxy-coated slides (Carlson Scientific; Peotone, Ill.), air dried for 10 minutes, and fixed in 1% paraformaldehyde in 0.1 M sodium cacodylate, pH 7.3 for 20 minutes on ice. Sections were overlaid with 100 $\mu$l/well of a lymphocyte suspension ($6\times10^6$/ml), in Dulbecco's PBS (PBS) containing 1% BSA, prepared from mesenteric lymph nodes of 10 week old CD1 mice (Charles River Laboratories; Wilmington, Mass.). The shear was provided by a gyratory shaker.

6. In Vivo Homing

Lymphocyte homing in vivo was determined by a variation of published procedures (Maly et al., Cell (1996) 86:643–653; Berlin-Rufenach et al., J. Exp. Med. (1999) 189, 1467–1478). Briefly, mouse mesenteric lymphocytes were labeled with 5 $\mu$M 5-chloromethylfluorscein diacetate (CMFDA, Cell-Tracker; Molecular Probes, Eugene, Oreg.) and injected ($1.7\times10^7$ cells in 200 $\mu$l PBS) into tail veins of recipient mice (8–14 weeks of age). One hour after injection, mice were sacrificed and peripheral lymph nodes (axillary and brachial lymph nodes), mesenteric lymph nodes, Peyer's patches, and spleen were dissected out. Lymphocyte suspensions prepared from these organs were subjected to flow cytometric analysis (FACScan, Becton-Dickinson) (500,000 cells per organ per mouse) to determine the fractional content of fluorescent cells. The data were normalized for each animal (fractional value of CMFDA positive cells divided by the mean of the fractional values for all of the +/+ mice within the experiment). This normalization procedure allowed pooling of the animals for three separate experiments.

B. Results

1. Gene Targeting of HEC-GlcNAc6ST

Figure 8:
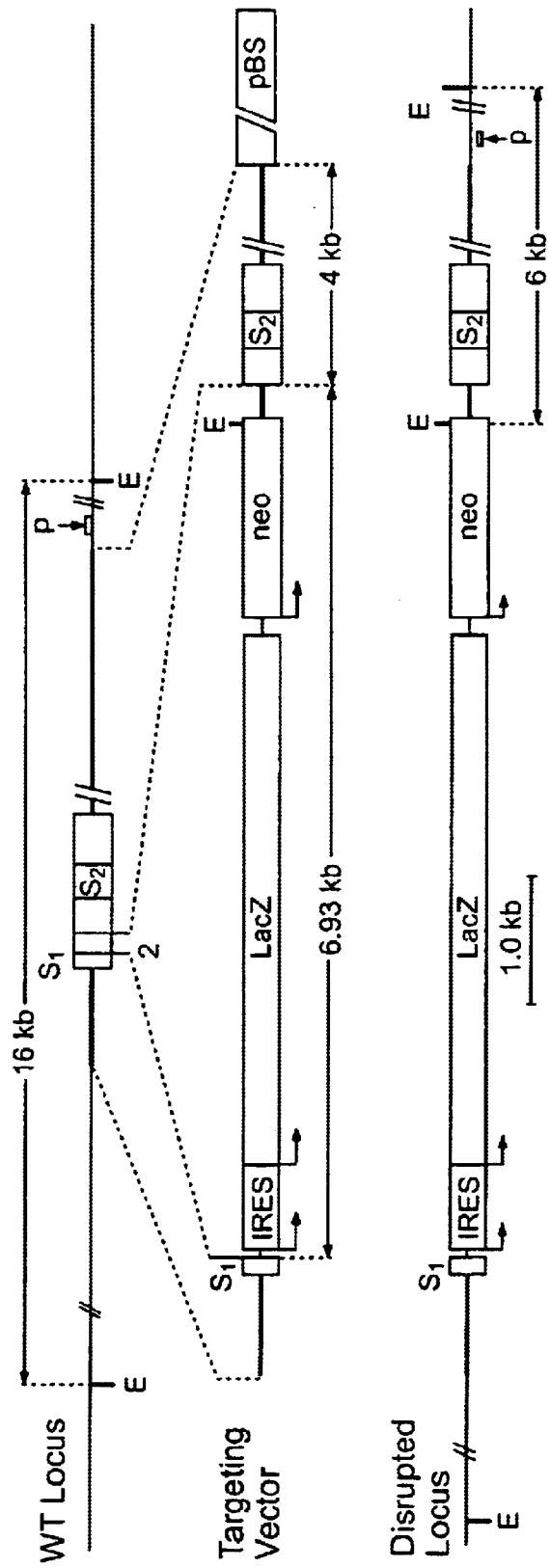
FIGS. 8. Structure of wild-type and mutant HEC-GlcNAc6ST loci. Thicker solid lines denote genomic sequence contained within the targeting construct. A 98 bp region ( ) of the HEC-GlcNAc6ST coding sequence corresponding to the putative PAPS 5'-phosphate binding site of the enzyme was replaced by a 6.93 kb IRES-lacZ reporter and neomycin resistance cassette (IRES-lacZ-neo). S1 denotes HEC-GlcNAc6ST coding sequence upstream of the deleted segment while S2 denotes HEC-GlcNAc6ST coding sequence downstream of. E indicates restriction sites for EcoRV, the restriction enzyme used for the Southern analysis. The blots were bybridizated with with a mixture of two probes, indicated by p. pBS denotes Bluescript vector sequence.

The gene encoding HEC-GlcNAc6ST was incorporated into a targeting vector mutated by deletion of a 98 bp region and insertion of a IRES-lacZ reporter and neomycin resistance cassette within the coding region (nt 136–233)(FIG. 8). The deleted region is predicted to encode the PAPS 5'-phosphate binding site. An appropriately targeted ES clone was injected into C57BL/6 blastocysts to produce chimeric mice. Germline transmission was confirmed in F1 crosses of chimeric mice. Southern analysis and RT-PCR performed on the resulting F2 generation allowed identification of HEC-GlcNAc6ST wild-type (+/+), heterozygous (+/−), and gene-deleted (−/−) mice. The intercrosses between heterozygotes resulted in normal sized litters. Of 80 mice born, 28% were HEC-GlcNAc6ST(−/−) (9 females and 13 males), indicating that the absence of this enzyme did not result in embryonic lethality. The −/− mice were healthy and vigorous with no evidence of propensity to infection. An RT-PCR analysis performed with RNA isolated from lymph nodes established that HEC-GlcNAc6ST mRNA was undetectable in −/− mice whereas mRNAs corresponding to two other carbohydrate sulfotransferases (KSGal6ST and GlcNAc6ST) were approximately equivalent between −/− and +/+ mice.

2. Leukocyte Distribution and Lymphoid Organ Histology in HEC-GlcNAc6ST Null Mice Previous studies have shown that L-selectin null mice exhibit abnormalities in the size and lymphocyte composition of certain secondary lymphoid organs. As was observed for the L-selectin null mice (Arbonés et al., Immunity (1994) 1, 247–260), we found that leukocytes levels in the blood (total leukocytes, lymphocytes, neutrophils and monocytes) were the same between HEC-GlcNAc6ST −/− and +/+ mice (FIG. 9A). In the case of peripheral lymph nodes (PN, pooled axillary and brachial), there was a marked reduction (65%) in lymphocyte cell number in −/− mice (FIG. 9B), comparable to the 70% reduction observed in L-selectin −/− mice (Arbonés et al., 1994). However, mesenteric lymph nodes (MN), Peyer's patches (PP), spleen, and thymus showed no significant differences in lymphocyte numbers between −/− and +/+ mice (FIGS. 9B and 9C), again in correspondence to the findings in the L-selectin null mice. The diminished lymphocyte count in peripheral lymph nodes was reflected in a comparable reduction in their weight whereas spleen weights were equivalent (not shown). Although we did not systematically compare the dimensions of lymph nodes, our impression was that the size of PN in −/− was smaller than those in +/+ mice. Histologically, PN from −/− mice showed an architecture that was generally the same as those from +/+ mice. Primary follicles were evident in the null mice, although generally smaller. HEV were also present in paracortical regions (see below). Immunohistochemical analysis confirmed that B and T-cells were concentrated in follicles and paracortical areas, as they are in lymph nodes of wild-type mice (data not shown). There were no obvious histological abnormalities in the other lymphoid organs (spleen, mesenteric nodes, Peyer's patches, and thymus).

3. Deficient Expression of L-Selectin Ligands and MECA 79 Epitopes in HEV of HEC-GlcNAc6ST Null Mice HEV with distinctive high-walled endothelial cells were evident in lymph nodes and Peyer's patches of HEC-GlcNAc6ST null mice. Staining with soluble L-selectin chimera molecules has been widely used as a direct measurement of L-selectin ligand activity within HEV. We employed an IgM chimera of L-selectin as our histochemical probe. Strikingly, lymph nodes from HEC-GlcNAc6ST null mice showed a complete absence of staining on the luminal and lateral aspects of the HEC. However, a distinct adluminal layer of staining was clearly present. In contrast, lymph nodes from wild-type mice exhibited staining on all aspects of the HEC. To verify that the adluminal staining represented true ligand activity, we determined the effect of preincubating the chimeric L-selectin with EDTA. This treatment inactivates the C-type lectin domain of L-selectin and prevents its interactions with carbohydrate-based HEV-ligands. The EDTA treatment completely eliminated the residual adluminal staining present in the HEV of −/− mice as well as the HEV staining in the +/+ mice. Sialidase treatment, another treatment known to inactivate L-selectin ligands on HEV, eliminated the adluminal ligands associated with the HEV of −/− mice and the pericellular staining of HEC in +/+ mice (data not shown).

To further characterize HEV in HEC-GlcNAc6ST null mice, we stained lymph node sections with an E-selectin IgM chimera. Previous work indicates that this selectin is capable of interacting with L-selectin ligands on HEV but does not require sulfation for this interaction. When the E-selectin chimera was applied to sections from wild-type mice, the HEV were stained in a pattern identical to that observed with the L-selectin/IgM chimera. However, whereas the L-selectin/IgM staining became adluminal in HEC-GlcNAc6ST null mice, the pericellular pattern of E-selectin/IgM staining was retained.

The MECA 79 antibody has been widely used as a probe for L-selectin ligands on HEV in secondary lymphoid organs. Experiments with chlorate have established that this antibody recognizes a sulfate-dependent epitope. Interestingly, unlike L-selectin, MECA 79 does not require sialylation or fucosylation for its binding to HEV-ligands, suggesting that this antibody recognizes a subregion of the relevant oligosaccharide structures. GlcNAc-6-sulfate appears to be the pertinent sulfation modification, as discerned from studies in which the epitope has been generated on transfected cells or in synthetic carbohydrate structures. The HEC-GlcNAc6ST null mice provided us with the opportunity to determine whether this particular GlcNAc-6-O-sulfotransferase is responsible for the expression of the MECA 79 epitope in HEV. MECA 79 staining was dramatically reduced in lymph node HEV of −/− mice. As was the case with the L-selectin IgM chimera, the only discernable staining in HEV of null mice was an adluminal layer. In contrast, HEV of +/+ mice exhibited staining around the entire HEC. The original characterization of the MECA 79 by Streeter et al. (Streeter et al., J. Cell. Biol. (1988) 107, 1853–1862) reported that staining in Peyer's patch HEV was adluminal. We confirmed this pattern in the +/+ mice. In the HEC-GlcNAc6ST null, this adluminal pattern was unaltered. To verify that other adhesion molecules were not altered in the lymph nodes of HEC-GlcNAc6ST null mice, we stained with antibodies to MAdCAM-1 and CD31. The patterns of staining on HEV for these two proteins were unaltered in the −/− mice.

4. Deficiencies in the Ability of HEV from HEC-GlcNAc6ST Null Mice to Support Interactions with Lymphocytes Exogenous lymphocytes can bind to HEV in cryostat-cut sections under shear conditions. When applied to lymph nodes, the interaction is completely dependent on the presence of both L-selectin and its ligands on HEV. We wanted to determine whether the deficiency in L-selectin ligands demonstrated above with soluble probes could be confirmed in a cell binding assay. Indeed, lymphocyte adherence to HEV from lymph nodes of HEC-GlcNAc6ST was virtually eliminated (FIG. 10). In the same experiment, we demonstrated substantial binding to HEV of +/+ lymph nodes, and we verified that the interaction was completely dependent on L-selectin, using a function-blocking antibody (i.e., MEL-14) and EDTA.

Since interactions between L-selectin and its HEV ligands are essential for lymphocyte homing to lymph nodes, we next asked whether HEC-GlcNAc6ST null mice would exhibit reduced migration to lymph nodes in vivo. Following established procedures, we labeled wild-type lymphocytes with an intravital fluorescent dye and injected them into the tail veins of either wild-type (+/+) or HEC-GlcNAc6ST null mice. After 1 hr, the number of labeled cells that had accumulated in various lymphoid organs was determined by performing flow cytometry (see section X. A, above). As shown in FIG. 11, lymphocyte homing in the −/− mice was significantly reduced to both peripheral lymph nodes and mesenteric lymph nodes (37% and 55% of +/+, respectively). Homing to Peyer's patches and spleen were at normal levels in the −/− mice. The residual homing to peripheral lymph nodes seen in the HEC-GlcNAc6T null mice may reflect retention of the α4β7-MAdCAM-1 homing system which is normally extinguished during postnatal development.

C. Discussion

The HEC-GlcNAc6ST null mice showed a very clear phenotype with respect to lymphocyte homing. Lymph nodes of −/− mice were clearly smaller and contained fewer lymphocytes. Lymphocyte homing to lymph nodes was markedly reduced, in particular in peripheral lymph nodes. That the homing defect was due to a deficiency in L-selectin ligands was demonstrated by in vitro adherence assays and by staining experiments with an L-selectin/IgM chimera and the MECA 79 antibody. MECA 79 binding to L-selectin ligands does not depend on their fucosylation or sialylation (see above), so its failure to stain the apical aspects of HEV in the null mice can be taken as indication that the GlcNAc-6-$SO_4$ modification was not present at this site.

Altered carbohydrate sulfation following from the deletion of HEC-GlcNAc6ST could result in changes of sialylation and fucosylation of HEV glycoproteins. Thus, the elimination of L-selectin ligand activity could conceivably be an indirect effect resulting from the absence of the GlcNAc-6-O-$SO_4$ modification. Our staining results with the E-selectin/IgM chimera argue against this possibility. We found that the E-selectin chimera stained lymph node HEV of +/+ mice in a pattern indistinguishable from that seen with the L-selectin chimera. This finding is consistent with the observations of those who have reported that a E-selectin/IgG chimera can block L-selectin ligand activity in lymph node HEV. Our analysis showed that while the L-selectin staining pattern was markedly altered in the null mice, the E-selectin staining pattern was basically retained. E-selectin binding to its physiologic ligands (e.g. PSGL-1) on leukocytes requires sialylation and fucosylation, and we inferred that similar requirements existed for its staining of HEV. In fact, we demonstrated above that sialidase treatment of sections eliminated E-selectin staining of HEV. With respect to sulfation, the GlcNAc-6-$SO_4$ modification imparted to recombinant GlyCAM-1 by HEC-GlcNAc6ST does not affect its binding to E-selectin. Thus, the above results indicate that that E-selectin binds to the $sLe^x$-like structures within L-selectin ligands independently of their sulfation, in a fashion analogous to certain $sLe^x$-specific mAbs. Based on these arguments, the unaltered E-selectin chimera staining of lymph node HEV in HEC-GlcNAc6T null mice implies that the sialylation and fucosylation of the relevant glycoproteins were not aberrant in the gene-targeted mice.

Taken together, the present results establish the importance of the GlcNAc-6-$SO_4$ modification in the function of L-selectin ligands and implicate the HEC-GlcNAc6T in the elaboration of these ligands within lymph node HEV.

A number of interesting parallels and differences are evident in comparing the present results with those obtained in studies of other gene targeting mice. The Fuc-TVII and L-selectin deficient mice exhibit homing deficiencies to Peyer's patches as well as lymph nodes in contrast to the HEC-GlcNAc6T null mice which show an effect only on lymph nodes. As in lymph nodes, L-selectin involvement in Peyer's patch homing is at the level of the initial tethering and rolling of lymphocytes along the HEV. Thus, our findings indicate that that the apically disposed ligands on Peyer's patch HEV do not require HEC-GlcNAc6T for their activity. In fact, we have failed to detect the expression of this sulfotransferase in Peyer's patch HEV by in situ hybridization techniques. It is conceivable that other sulfotransferases may be involved in ligand biosynthesis in this lymphoid organ. Alternatively, the apical ligands in Peyer's patch HEV may be sulfate-independent.

Fuc-TVII deficient mice exhibit a very pronounced leukocytosis unlike the HEC-GlcNAc6T and L-selectin null mice in which normal leukocyte levels are found in the blood. This difference is mostly likely attributable to the fact that Fuc-TVII makes an essential contribution to the physiological ligands for all three selectins whereas the action of HEC-GlcNAc6T may be restricted to endothelial ligands for L-selectin and very likely a subset of them (see above).

An unexpected finding of the present study was that L-selectin ligand activity, as detected by both the L-selectin/IgM chimera and MECA 79, were detected adluminally in lymph node HEV. These ligands are present in the HEV of wild-type mice but were previously unappreciated since apical and lateral staining by these reagents is very prominent. With the loss of apical and lateral staining in lymph nodes of HEC-GlcNAc6T null mice, the adluminal staining was obvious. Interestingly, Streeter et al. (Streeter et al., 1988) reported that the only MECA staining seen in Peyer's patch HEV was adluminal. We confirmed this adluminal pattern in the wild-type mice in our study and further showed that deletion of HEC-GlcNAc6T did not eliminate this staining. Thus, MECA 79 epitopes presumably due to the action of a GlcNAc-6-O-sulfotransferase (but not HEC-GlcNAc6ST) are associated with adluminal aspect of HEV in lymph nodes and Peyer's patches. GlcNAc6ST (Uchimura et al., 1998 J. Biol. Chem. 273, 22577–22583) and I-GlcNAc6ST (Lee et al., 1999 Biochem. Biophys. Res. Commun. 263, 543-549.) are candidates for this enzyme. Whether these adluminal ligands for L-selectin are involved in the migration of extravasated lymphocytes within the lymph node proper is a subject for future study.

It is apparent from the above results and discussion that a human glycosyl sulfotransferase, as well as polypeptides related thereto and nucleic acid compositions encoding the same are provided by the subject invention. These polypeptide and nucleic acid compositions find use in a variety of diverse applications, including research, diagnostic, screening and therapeutic applications. Also provided are improved methods of treating diseases associated with selectin-sulfated ligand mediated binding events, since agents that selectively reduce or inhibit the activity of the subject enzyme are employed, so that other sulfotransferases whose activity is beneficial are not adversely affected.

All publications and patent applications cited in this specification are herein incorporated by reference as if each individual publication or patent application were specifically and individually indicated to be incorporated by reference. The citation of any publication is for its disclosure prior to the filing date and should not be construed as an admission that the present invention is not entitled to antedate such publication by virtue of prior invention.

Although the foregoing invention has been described in some detail by way of illustration and example for purposes of clarity of understanding, it is readily apparent to those of ordinary skill in the art in light of the teachings of this invention that certain changes and modifications may be made thereto without departing from the spirit or scope of the appended claims.

What is claimed is:

1. A glycosyl sulfotransferase-3 (GST-3) polypeptide present in other than its natural environment, wherein said GST-3 polypeptide comprises an amino acid sequence having at least about 60% amino acid sequence identity to the amino acid sequence set forth in SEQ ID NO:02.

2. The GST-3 polypeptide of claim 1, wherein said polypeptide comprises the amino acid sequence set forth in SEQ ID NO:02.

3. The GST-3 polypeptide of claim 1, wherein said polypeptide catalyzes the transfer of a sulfate group from a donor compound to a selectin ligand.

4. A glycosyl sulfotransferase-3 (GST-3) polypeptide present in other than its natural environment, wherein said GST-3 polypeptide is encoded by a nucleic acid comprising a nucleotide sequence having at least about 75% identity to SEQ ID NO:01.

5. The GST-3 polypeptide of claim 4, wherein said polypeptide is encoded by a nucleic acid comprising a nucleotide sequence having at least about 90% identity to SEQ ID NO:01.

6. The GST-3 polypeptide of claim 4, wherein said polypeptide is encoded by a nucleic acid comprising a nucleotide sequence having at least about 95% identity to SEQ ID NO:01.

7. The GST-3 polypeptide of claim 4, wherein said polypeptide comprises the amino acid sequence set forth in SEQ ID NO:02.

8. The GST-3 polypeptide of claim 4, wherein said polypeptide catalyzes the transfer of a sulfate group from a donor compound to a selectin ligand.

9. The GST-3 polypeptide of claim 8 or claim 3, wherein the selectin ligand is an E-selectin ligand.

10. The GST-3 polypeptide of claim 8 or claim 3, wherein the selectin ligand is a P-selectin ligand.

11. The GST-3 polypeptide of claim 8 or claim 3, wherein the selectin ligand is an L-selectin ligand.

12. The GST-3 polypeptide of claim 11, wherein the L-selectin ligand is selected from GlyCAM-1, CD34, MAdCAM-1, Sgp200, and podocalyxin.

13. A composition comprising a polypeptide according to claim 4 or claim 1.

* * * * *